United States Patent [19]
Eisenbach-Schwartz et al.

[11] Patent Number: 5,962,404
[45] Date of Patent: Oct. 5, 1999

[54] ENZYMATICALLY-PRODUCED OLIGODENDROCYTE CYTOTOXIC DIMERIC IL-2 FACTOR

[75] Inventors: Michal Eisenbach-Schwartz, Rehovot; Shoshana Eitan, Tel-Aviv, both of Israel

[73] Assignee: Yeda Research & Development Co., Ltd., Rehovot, Israel

[21] Appl. No.: 08/795,007

[22] Filed: Feb. 5, 1997

Related U.S. Application Data

[63] Continuation-in-part of application No. 08/467,202, Jun. 7, 1995, abandoned, and application No. 08/483,836, Jun. 15, 1995, which is a continuation of application No. 08/106,970, Aug. 16, 1993, abandoned, which is a continuation of application No. 07/840,783, Feb. 24, 1992, abandoned, which is a continuation-in-part of application No. 07/573,580, Aug. 27, 1990, abandoned, said application No. 08/467,202, is a division of application No. 08/099,759, Jul. 30, 1993, Pat. No. 5,514,565.

[30] Foreign Application Priority Data

| Aug. 28, 1989 | [IL] | Israel | 91459 |
|---|---|---|---|
| Feb. 27, 1991 | [IL] | Israel | 97365 |
| Jul. 30, 1992 | [IL] | Israel | 102686 |
| Oct. 20, 1992 | [IL] | Israel | 103469 |
| May 19, 1993 | [IL] | Israel | 105752 |

[51] Int. Cl.⁶ ............................................. A61K 38/20
[52] U.S. Cl. .......................... 514/2; 514/21; 530/399; 530/324; 435/68.1
[58] Field of Search ............................... 530/399, 324; 514/2, 21; 435/68.1

[56] References Cited

PUBLICATIONS

Kovarova et al., SBornik Vedeckych Praci Lekarske Fakulty Karlovy Univerzity V Hradci Kralove. Supplementum. 32(4): 397–411 (1989). Abstract., 1989.

*Primary Examiner*—Jean C. Witz
*Attorney, Agent, or Firm*—Evenson, McKeown, Edwards & Lenahan, P.L.L.C.

[57] ABSTRACT

An enzymatically-producible dimeric IL-2 such as mammalian, more particularly, human dimeric IL-2, having oligodendrocyte cytotoxic activity, is useful as active ingredient of pharmaceutical compositions for inducing and facilitating regeneration of injured nerves of the central nervous system in mammals, including humans.

5 Claims, 25 Drawing Sheets

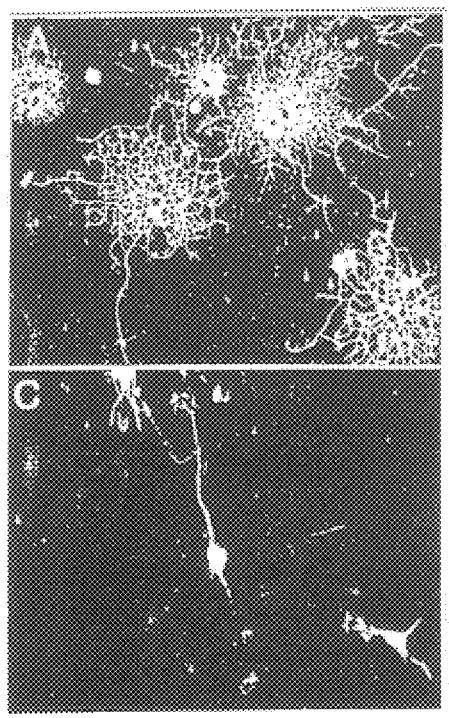
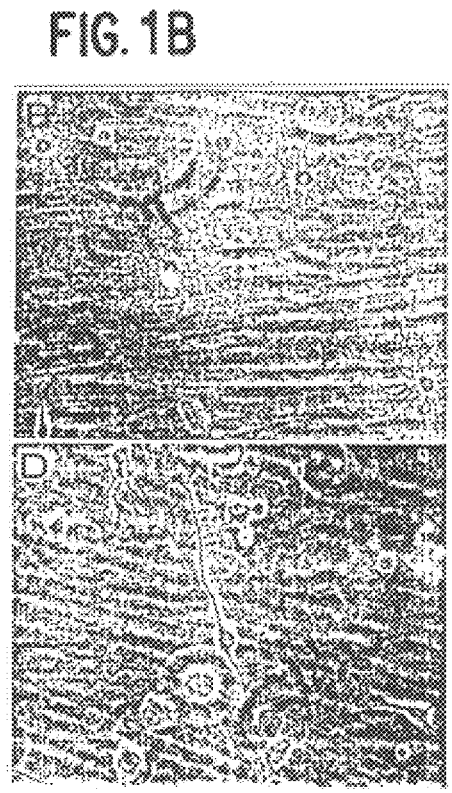
FIG.1A
FIG.1C
FIG.1B
FIG.1D
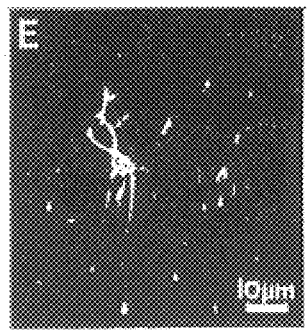
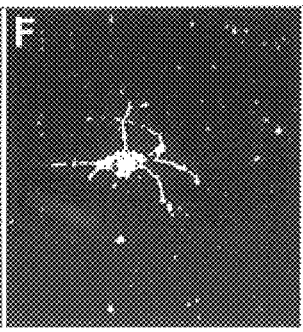
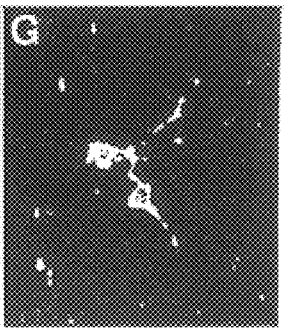
FIG.1E
FIG.1F
FIG.1G

 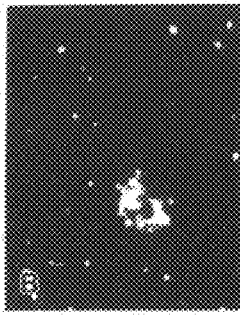 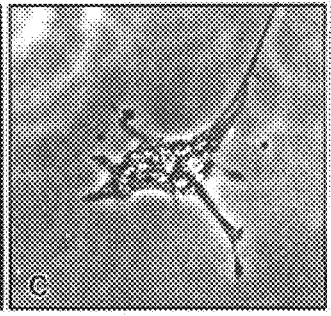 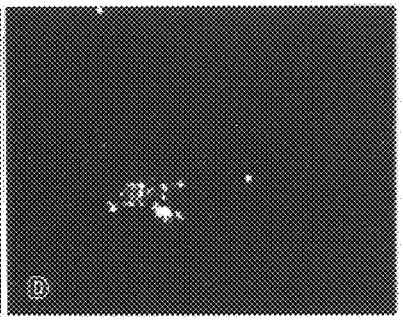
FIG. 9A  FIG. 9B  FIG. 9C  FIG. 9D
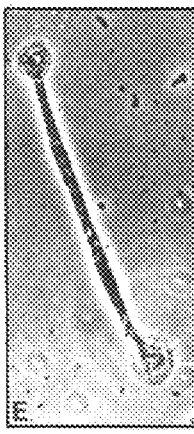 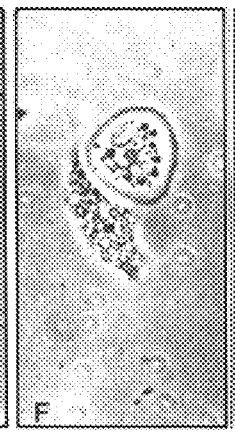   
FIG. 9E  FIG. 9F  FIG. 9G  FIG. 9H  FIG. 9I

REACTION A

1. LEFT PRIMER

SEQUENCE: 5'-CTCGAGAAGCTTACAGTAACCTCAACTCCTGC-3'  5' extension: CTCGAGAAGCTT

LENGTH: 32    Bp-pos: 24

2. RIGHT PRIMER

SEQUENCE: 5'-CTCGAGCTCGAGAGTTAGTGTTGAGATGATGC-3'  5' extension: CTCGAGCTCGAG

LENGTH: 32    Bp-pos: 506

REACTION B

1. LEFT PRIMER

SEQUENCE: 5'-CTCGAGCTCGAGATGTACAGGATGCAACTCCT-3'  5' extension: CTCGAGCTCGAG

LENGTH: 32    Bp-pos: 48

2. RIGHT PRIMER

SEQUENCE: 5'-CTCGAGCTGCAGAATAGAAGGCCTGATATGTT-3'  5' extension: CTCGAGCTGCAG

LENGTH: 32    Bp-pos: 551

ENZYMATICALLY-PRODUCED OLIGODENDROCYTE CYTOTOXIC DIMERIC IL-2 FACTOR

RELATED APPLICATIONS

The present patent application is a continuation-in part of both U.S. Ser. No. 08/467,202, filed Jun. 7, 1995 now abandoned, and U.S. Ser. No. 08/483,836, filed Jun. 15, 1995; U.S. Ser. No. 08/467,202 was a divisional application of U.S. Ser. No. 08/099,759, filed Jul. 30, 1993, now U.S. Pat. No. 5,514,565; U.S. Ser. No. 08/483,836 is a continuation application of U.S. Ser. No. 08/106,970 filed Aug. 16, 1993, now abandoned, which was a continuation application of U.S. Ser. No. 07/840,783, filed Feb. 24, 1992, now abandoned, which was a continuation-in-part application of U.S. Ser. No. 07/573,580 filed Aug. 27, 1990, now abandoned, all said patents/patent applications being herein incorporated by reference in their entirety.

FIELD OF THE INVENTION

The present invention relates to a novel oligodendrocyte cytotoxic factor herein identified as being dimeric IL-2 which is obtainable by incubation of IL-2 with a nerve-derived transglutaminase. The new factor is useful for inducing and facilitating regeneration of injured nerves of the central nervous system (CNS) in mammals, including humans.

BACKGROUND OF THE INVENTION

Adult nerves of the mammalian central nervous system (CNS) show poor regenerative ability after axonal injury. Spontaneous growth of injured axons does occur, but ceases after a few hundred microns without traversing the site of the injury and elongating in the distal stump. The failure to regenerate has been attributed to the inhospitable nature of the nerve's environmental milieu, including the inability of astrocytes (the scar forming cells) to support growth, the paucity of macrophages and/or their products, and the formation of mature oligodendrocytes which inhibit axonal growth.

The non-neuronal cells contribute to the CNS environment and they have been implicated in the failure of CNS regeneration in mammals. These cells include astrocytes, which hypertrophy to form fibrous scars in response to lesion and oligodendroglia, which are inhibitory to axonal growth. The astrocytic scar is largely composed of type-1 astrocytes and has been considered to prevent growth by forming a physical barrier. The time course of scar formation is long, however, and it seems unlikely that a barrier formed by the scar would prevent regenerative axonal growth in the immediate post traumatic period. Type-1 astrocytes in rat optic nerve have been shown to express laminin, a molecule implicated in support of axonal outgrowth, prenatally, during the development of the optic nerve. Mammalian adult brain type-1 astrocytes normally do not express laminin, except only transiently following an injury to the brain. In contrast, laminin is continuously expressed in regenerative fish optic nerve. In in vitro preparations, axons grow in close contact with type-1 astrocytes. Mature oligodendrocytes are now believed to be non permissive for axonal growth. Growing axons will avoid contacting mature oligodendrocytes, in vitro. During development, most axonal growth in the optic nerve takes place before birth, before any oligodendrocytes have differentiated. It seems, therefore, that axonal regeneration in mammals is hindered by both the presence of mature oligodendrocytes, which are non permissive to axonal growth, and the type-1 reactive astrocytes, which are lacking the supportive element(s), in contrast to the fish optic nerve.

Prior work of the present inventors and others has shown that the CNS of lower vertebrates, specifically regenerating fish optic nerve, is a source of factors which, when applied at the appropriate time and in appropriate amounts to injured mammalian adult optic nerves, can support regenerative axonal growth (Schwartz et al., 1985; Hadani et al., 1984; Lavie et al., 1987; Cohen et al., 1989; Lavie et al., 1990; and European Patent No. 172987). An activity cytotoxic to oligodendrocytes was attributed to substances within these preparations, which presumably enable the fish optic nerve to overcome the inhibitory activity associated with oligodendrocytes (Sivron et al., 1990 and 1991). The cytotoxicity in vitro was shown to be not only to fish oligodendrocytes, but also to rat oligodendrocytes (Published European Application EP No. 415,321, Sivron, T. et al., 1990 and Cohen et al., 1990). These substances are associated, directly or indirectly, with macrophages or other blood derived cells.

Interleukin-2 (IL-2) is a lymphokine known to be synthesized and secreted by T cells after activation with antigen or mitogen in the presence of IL-1 (Smith, 1988). IL-2 in the immune system has been considered to be an important cytokine, responsible for either inhibition or progression of many immune responses (Liang et al., 1989). In contrast, very little is known about the role of IL-2 in the brain. In the nervous system, some of the observations related to the effects of IL-2 on oligodendrocytes appear to be contradictory. Recent studies have attributed an inhibitory effect on oligodendrocytes to the cytokine IL-2 (Saneto et al., 1986 and 1987), while other studies have shown a proliferative effect of IL-2 on oligodendrocytes (Benveniste and Merril, 1986). IL-2 in mammals has been shown to be a product of lymphocytes (Smith, 1988) and some reports have indicated that fish lymphocytes may have IL-2-like activity (Capsi and Avtalion, 1984).

An association between IL-2 and injury in the CNS in general, and in the brain in particular, has also been pointed out. Nieto-Sampedro et al., 1987, found IL-2 activity after brain injury. Similarly, Liang et al., 1989, found IL-2 in brain lesions created by MPP+(1-methyl-4-phenyl pyrimidine). In addition, up-regulation of IL-2 binding sites was observed by Araujo et al., 1989, in rat hippocampus as a result of injury. Nevertheless, no association between IL-2 and CNS regeneration has yet been suggested.

Other recent studies have suggested that regeneration might be prompted by treatments that circumvent growth hindrance by oligodendrocytes, e.g., applications of factor cytotoxic to oligodendrocytes such as tumor necrosis factor (TNF) (U.S. Pat. No. 5,580,555, and Schwartz et al., 1991) or of antibodies directed against the oligodendrocyte-associated inhibitors (Schnell et al., 1990).

Robbins et al., 1987, have reported that stimulation of rat astrocytes in vitro resulted in the generation of a cytotoxic factor that is functionally similar to TNF. They also reported that recombinant human TNF (rhTNF) has cytotoxic activity directed against rat oligodendrocytes. Selmaj et al., 1988, reported on the testing of rhTNF for its effect on myelinated cultures of mouse spinal cord tissue. They found that rhTNF induced delayed-onset oligodendrocyte necrosis and a type of myelin dilatation.

Despite substantial research efforts worldwide, no safe and effective means for causing regenerative growth of CNS axons in mammals, and particularly humans, has yet been developed. Such a means, and particularly a pharmaceutical which can be injected at the site of desired regeneration would be very desirable in order to help alleviate post-traumatic paraplegia or quadriplegia, blindness, deafness, surgically associated axotomy, etc.

SUMMARY OF THE INVENTION

The present invention relates to an oligodendrocyte cytotoxic factor initially found to be present in the conditioned medium of regenerating injured nerves of lower vertebrates, such as fish, and designated OCF, and now identified according to the invention as being dimeric IL-2 which is obtainable by incubation of IL-2 with a nerve-derived transglutaminase.

Throughout the specification the terms "OCF", "dimeric IL-2" or "OCF/dimeric IL-2" will be used when referring to the factor, although OCF will be used more specifically when referring to the factor identified initially in the conditioned medium of regenerating fish optic nerves.

The OCF/dimeric IL-2 of the invention is selectively toxic to cells of the oligodendrocyte lineage but not to other cells such as type-1 astrocytes and fibroblast cells. The factor inhibits differentiation of progenitors of the oligodendrocyte lineage to mature oligodendrocytes, and also reduces the number of mature oligodendrocytes in cultures of injured nerves.

The dimeric IL-2 of the invention having oligodendrocyte cytotoxic activity is produced by the method claimed in related U.S. Pat. No. 5,514,565, which comprises incubating monomeric IL-2 with a transglutaminase enzyme obtainable from injured fish optic nerve which dimerizes monomeric IL-2 into dimeric IL-2 having said cytotoxic activity. The monomeric IL-2 may be from lower vertebrates, e.g. fish, or a mammalian IL-2 such as murine or human IL-2. Preferably, it is recombinant human IL-2. The purified nerve-derived transglutaminase enzyme is the subject of related U.S. application Ser. No. 08/467,202.

The dimeric IL-2 factor of the invention induces and facilitates regenerative growth of the axons of injured nerves of the mammalian central nervous system. The invention also relates to pharmaceutical compositions for inducing and facilitating regeneration of injured nerves of the CNS in mammals, including humans, comprising an effective amount of the dimeric IL-2 of the invention, and also relates to methods of using the dimeric IL-2 to facilitate regenerative axonal growth comprising administering to the site of injury an effective amount of the dimeric IL-2 of the invention.

The compositions comprising the dimeric IL-2 of the invention enable injured nerves to be treated in vivo by selective elimination of oligodendrocytes, normally an obstacle to regeneration in mammalian CNS, thereby facilitating the growth of axons in their own environment.

BRIEF DESCRIPTION OF THE DRAWINGS

FIG. 1A shows the effect of fish conditioned medium of regenerating fish nerves ("CM-R") on adult 04 positive cells in cultures of injured adult rat optic nerves. Fluorescent micrographs of the control cells in defined medium without any treatment are shown. Cells were prepared from adult rat optic nerves that were crushed three days before excision and were seeded on poly-L-lysine coated coverslips in defined medium. Cultures were stained for 04 immunoreactivity at 96 h in vitro, by an indirect immunofluorescent method, which was carried out as follows: Cells were first incubated with mouse anti-04 antibodies for 30 min, followed by 30 min incubation with fluorescein conjugated goat anti-mouse IgM. At the end of the second incubation, the cells were washed and fixed with cold methanol($-20°$ C.) for 10 min. Pictures were taken from one experiment, the results of which were reproduced in two additional experiments; FIG. 1B shows phase micrographs of the control cells in defined medium without any treatment according to the protocol in FIG. 1A;

FIG. 1C shows 04 positive cells in cultures which were treated with CM-R (12 $\mu$g protein/ml) for 48 h prior to staining as fluorescent micrographs;

FIG. 1D shows 04 positive cells of FIG. 1C in cultures which were treated with CM-R (12 $\mu$g protein/ml) for 48 h prior to staining as phase micrographs;

FIG. 1E shows 04 positive cells which were treated with CM-R (12 $\mu$g protein/ml) for 48 h prior to staining;

FIG. 1F shows 04 positive cells which were treated with CM-R (12 $\mu$g protein/ml) for 48 h prior to staining;

FIG. 1G shows 04 positive cells which were treated with CM-R (12 $\mu$g protein/ml) for 48 h prior to staining;

FIG. 2 shows also that the inhibitory effect was also reproducible when the number of Galc positive cells was monitored by ELISA, rather than by immunofluorescence. Also shown in FIG. 2, is a dose dependency curve of the inhibitory activity as a function of the amount of applied CM-R;

Each bar represents an average (±SD) of 3 wells.

FIG. 4A shows a comparison between PDGF and CM-R effects on newborn rat brain oligodendrocytes. Cultures of oligodendrocytes from neonatal rat brains were obtained as in FIG. 2. In all cultures, an identical number of cells was seeded. At 48 h in vitro, cultures were stained for either Galc or A2B5 positive cells. In treated cultures, either PDGF (5 ng/ml, Sigma) or CM-R (12 μg protein/ml) were added at the time of seeding. As control, we used cultures kept in defined medium which were not treated. Fluorescent micrographs show cells stained with mouse A2B5 monoclonal antibodies in cultures treated with PDGF.

FIG. 4B shows fluorescent micrographs showing cells stained with mouse A2B5 monoclonal antibodies in control cultures according to the protocol in FIG. 4A;

FIG. 4D shows fluorescent micrographs showing cells stained with mouse A2B5 monoclonal antibodies in cultures treated with CM-R according to the protocol in FIG. 4A;

FIG. 9A shows resident macrophages in cultures of fish optic nerves which were organ cultured before dissociation. The figure shows different morphologies of the resident macrophages, these being round. The micrograph is phase contrast. The micrograph is 500×;

FIG. 9B shows morphologies of the resident macrophages according to FIG. 9A, which in this case are more round. The micrograph is 6D2 labeled. The micrograph is 500×;

FIG. 9C shows morphologies of the resident macrophages according to FIG. 9A, which in this case are more round. The micrograph is a phase contrast. The micrograph is 500×;

FIG. 9D shows morphologies of the resident macrophages according to FIG. 9A, which in this case are more round. The micrograph is 6D2 labeled. The micrograph is 500×;

FIG. 9E shows morphologies of the resident macrophages according to FIG. 9A, which in this case have a more fibroblast-like appearance. The micrograph is a phase contrast. The micrograph is 500×;

FIG. 9F shows morphologies of the resident macrophages according to FIG. 9A. Contact was observed between the resident macrophages and the blood-borne macrophages. The micrograph is a phase contrast. The micrograph is 500×;

FIG. 9G shows morphologies of the resident macrophages according to FIG. 9A. Contact was observed between the resident macrophages and the blood-borne macrophages. The micrograph is 6D2 labeled. The micrograph is 500×;

FIG. 9H shows morphologies of the resident macrophages according to FIG. 9A. Contact was observed between the oligodendrocytes and both types of macrophages. The nature of this contact may be engulfing. The micrograph is a phase contrast. The micrograph is 500×;

FIG. 9I shows morphologies of the resident macrophages according to FIG. 9A. Contact was observed between the oligodendrocytes and both types of macrophages. The nature of this contact may be engulfing. The micrograph is 6D2 labeled. The micrograph is 500×;

FIG. 21A depicts design and construction of human IL-2 cDNA products by PCR. The two sets of primers, including the added restriction sites (dashed boxes), used to construct the human IL-2 cDNA products (Bp-pos refers to the position of the primer on the human lymphocyte-derived IL-2 cDNA sequence)

DETAILED DESCRIPTION OF THE INVENTION

Figure 2:
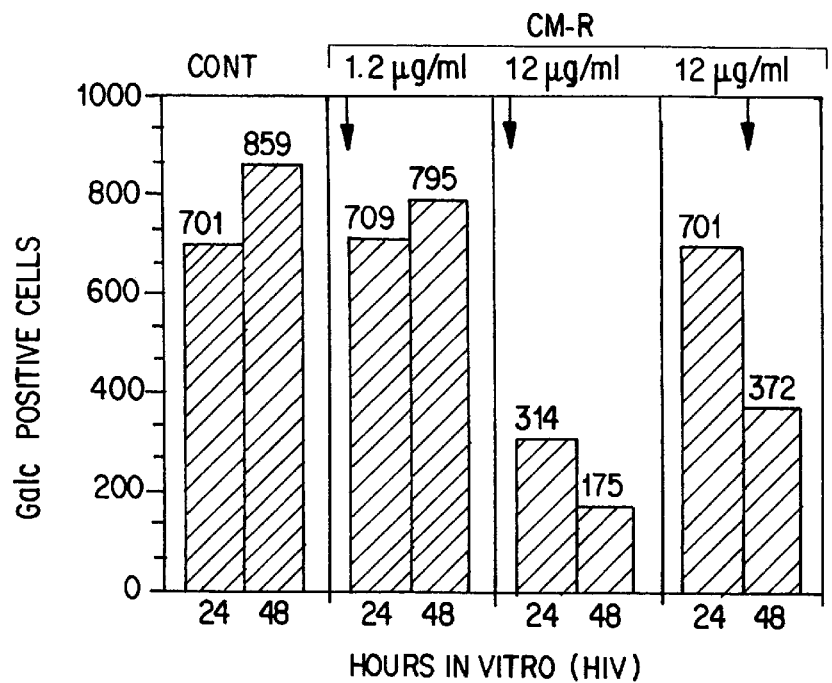
FIG. 2 shows the effect of CM-R on in vitro development of Galc positive cells from 1 day postnatal rat brain. Brains from newborn rats were dissected out and dissociated according to the procedure of McCarthy and DeVellis. After 8 days in vitro, the oligodendrocytes were shaken off and seeded on poly-L-lysine coated coverslips (104 cells/well in a microtiter plate). Cultures were stained at 24, 48 and 72 h in vitro, for Galc immunoreactivity by the direct immunofluorescence technique using fluorescein conjugated goat anti-mouse IgM. In experimental cultures, CM-R (1.2 and 12 $\mu$g protein/ml) was added at the indicated time after seeding (marked by an arrow). In each case, the concrete number of Galc positive cells on the entire coverslips was counted (numbers above the everyday graph). In the control culture, the number of Galc positive cells remained relatively constant throughout the experiment (24–72 h) and was about 700–850 cells. Note the lack of inhibitory effect on development of mature oligodendrocytes, at all periods in culture, when CM-R at a concentration of 1.2 $\mu$g protein/ml was added to the culture medium at the time of seeding. A marked (more than 50%) inhibitory effect was observed when CM-R at 12 $\mu$g protein/ml was added at the time of seeding. When CM-R was added at 24 h in vitro after seeding there was almost 50% inhibition of oligodendrocyte maturation after additional 24 h in vitro, however, this effect seemed to be transient. This experiment was repeated twice and gave qualitatively the same results (N.D.-not done).

The novel dimeric IL-2 of the invention is an oligodendrocyte cytotoxic factor (OCF) that was originally found in regenerating injured nerves of lower vertebrates, such as fish. It is present in the conditioned medium of regenerating fish optic nerves and of macrophages.

The term "conditioned medium" (CM), as used throughout the present specification, refers to a medium conditioned by regenerating fish optic nerves prepared by incubating segments of fish optic nerves, removed 8 days after crush, in a serum-free medium for 1.5–3 h at room temperature, collected and filtered. The CM obtained is free of any tissue. Examples of serum-free media that can be used are Dulbecco's modified Eagle's medium (DMEM; 4 optic nerves per 300 µl medium), L-15 Leibowitz medium, etc. When comparison is made between conditioned medium of regenerating nerves and of intact nerves, then CM-R is used for CM of regenerating nerves and CM-N for CM of intact nerves.

The cytotoxic activity of the OCF/dimeric IL-2 of the invention is measured by its ability to reduce the number of mature oligodendrocytes in rat brain cultures. The number of oligodendrocytes is determined by using antibodies directed to galactocerebroside (Galc), which label mature oligodendrocytes. Reduction in the number of Galc positive cells indicates reduction in the number of mature oligodendrocytes. The assay is disclosed with more details in the Experimental Procedures and Examples herein.

The cytotoxic activity of OCF/dimeric IL-2 is specific to oligodendrocyte lineage. Thus, it inhibits differentiation of progenitors of the oligodendrocyte lineage to mature oligodendrocytes and type-2 astrocytes. It also reduces the number of mature oligodendrocytes in cultures of injured nerves. It has no cytotoxic effect on other cells, such as type-1 astrocytes or fibroblast cells.

The OCF was first found to be present in the CM of regenerating injured fish optic nerves, but not in the CM of non-injured fish optic nerves, nor in the CM of injured mammalian optic nerves. The factor was found to be water soluble and heat-sensitive, losing its activity at 56° C. after 30 minutes, and at 100° C. after 10 minutes. It is sensitive to proteases, losing activity upon digestion with trypsin.

The OCF originating from the fish optic nerves was then found, according to the present invention, to be an IL-2-like substance, as confirmed by the following: (i) it was purified by affinity chromatography of CM of regenerating fish optic nerves with anti-IL-2 antibodies; (ii) antibodies against IL-2 neutralized the oligodendrocyte cytotoxic activity of the conditioned medium derived from regenerating fish optic nerves; (iii) Western blot analysis revealed the presence of an IL-2 immunoreactive band of 28 kDa in the fish conditioned medium; and (iv) recombinant mouse IL-2 had a selective cytotoxic effect in vitro on oligodendrocytes but not on astrocytes. The apparently higher potency of the dimeric IL-2 in the fish conditioned medium than that of the recombinant mouse IL-2 strongly suggests that the specificity of the activity is determined by the tissue and not by the species, i.e., the CNS-derived fish IL-2 is probably different from the recombinant IL-2, which is immune derived, indicating that the active molecule from fish optic nerves is a modification of the immune-derived IL-2. This is further substantiated by the results, shown in FIG. 11, that the IL-2 immunoreactive substance in fish blood lymphocytes (LMP) is a polypeptide of about 14 kDa, not a 28 kDa polypeptide as is the IL-2-like substance in the nerve (CM).

Since the OCF and the IL-2-like substance were detected in media conditioned by the injured fish optic nerve, but not in media conditioned by the intact fish optic nerve, the machinery for local processing of IL-2, and its modification to the dimeric form having oligodendrocyte cytotoxic activity, was sought for in the injured fish optic nerve. It was then found, as described in the related U.S. application Ser. No. 08/467,202, that an enzyme of the transglutaminase family is obtainable from injurede fish optic nerve, and this nerve-derived transglutaminase ($TN_G$) converts mammalian IL-2 to dimeric IL-2 having oligodendrocyte cytotoxic activity.

The $TN_G$ used to produce the dimeric IL-2 according to the invention is a water-soluble enzyme, has a molecular weight of about 55 kDa as analyzed by SDS-PAGE and silver staining. It can be prepared as described in said related U.S. application Ser. No. 08/467,202 by affinity chromatography of conditioned medium of injured fish optic nerve with antibodies raised against a peptide corresponding to a well-conserved active site epitope of transglutaminases.

The process for the enzymatic production of the dimeric IL-2 having oligodendrocyte cytotoxic activity of the invention is the subject of the related U.S. Pat. No. 5,514,565, and comprises incubating monomeric IL-2 with a $TN_G$ and then recovering the dimeric IL-2 having olygodendrocyte cytotoxic activity.

The monomeric IL-2 used according to the present invention as substrate of $TG_N$ includes native and recombinant IL-2 of any species, such as fish, and preferably mammalian IL-2, most preferably human IL-2, and may be produced by any convenient technique, such as by the process of Robb et al., 1983. It is preferably obtained by recombinant DNA technologies, for example as described by Taniguchi et al., 1983, or Devos, R., 1983. Recombinant murine and human IL-2 are preferably used according to the invention.

The enzymatically-producible dimeric mammalian IL-2 of the present invention has the following characteristics:
(i) it is water-soluble;
(ii) it is a covalent dimer of IL-2;
(iii) it is selectively toxic to the oligodendrocyte lineage, but not to other cells, such as type-1 astrocytes and fibroblast cells;
(iv) its cytotoxic activity to oligodendrocytes is neutralized by antibodies directed against IL-2;
(v) it is obtainable from mammalian IL-2 by incubation with a nerve-derived transglutaminase; and
(vi) it has a molecular weight of about twice the molecular weight of the substrate mammalian IL-2 as determined by Western blot analysis.

In a preferred embodiment, the enzymatically-produced mammalian dimeric IL-2 according to the invention is human dimeric IL-2 having a molecular weight of about 30 kDa.

The enzymatically-produced dimeric IL-2 of the invention is for use in pharmaceutical compositions for inducing and facilitating regeneration of injured nerves of the CNS in mammals, including humans.

The enzymatically-produced dimeric IL-2 of the invention is preferably administered to a patient in need thereof locally to the target organ.

The dimeric IL-2 is used in a quantity and purity sufficient to induce and facilitate regeneration of axons at the site of a CNS injury in a mammal, particularly humans. It is administered in any manner which is suitable to bring the factor to the vicinity of the injured axons to be regenerated, preferably, it is injected in a pharmaceutically acceptable liquid carrier directly to the site. Alternatively, an implant bearing the dimeric IL-2 may be surgically inserted. Such an implant may consist of any material, such as nitrocellulose, which will absorb the dimeric IL-2 like a sponge and slowly release it at site of implantation. Other means of delivery will be apparent to those skilled in this art, and are contemplated within the scope of the present invention.

The amount of the dimeric IL-2 to be administered to any given patient depends on a variety of factors, such as the injury being treated, the site of injured axons it is wished to regenerate and the condition of the patient. Typically, however, it is administered as a single injection or as multiple injections around the injured site, or it is soaked onto nitrocellulose or any other absorbable carrier. Precise dosage will be empirically determined.

The dimeric IL-2 is preferably administered as soon as possible after the injury being treated. Thus, it is preferably used for acute injury rather than chronic injury. It will be more difficult to facilitate regeneration in accordance with the present invention the longer a period of degeneration has existed.

While the administration of dimeric IL-2 alone shows good results, such treatment may be combined with any type of concomitant therapy which may tend to augment its effects. For example, Irradiation of the injury site with low energy laser, preferably He-Ne laser, (5 min/day, 35 mW) can delay the post traumatic process of the degeneration and thereby delay scar formation (Assia et al., Brain Res., 476, 205–212 (1988).

The various injuries which can be treated in accordance with the present invention are myriad and will be readily apparent to those of ordinary skill in the art. Without limitation, there may be mentioned spinal cord injuries, injuries to the optical nerve or to the aural nerves, etc. Injury to CNS neurons during neurosurgery or caused by tumors may also be treated by means of the present invention.

For the purpose of the present invention, the dimeric IL-2 may be formulated with any pharmaceutically acceptable carrier or excipient. It may be presented to an aqueous solution, for example as a sterile aqueous solution. A solution or powder containing dimeric IL-2 may be stabilized by means of a stabilizing agent. It may be formulated in a unit dosage injectable form (solution, suspension, emulsion) preferably in a pharmaceutically acceptable carrier medium that is inherently non-toxic and non-therapeutic. Examples of such vehicles include saline, Ringer's solution, dextrose solution, mannitol and normal serum albumin. Non-aqueous vehicles such as fixed oils and ethyl oleate may also be used. The carrier medium may contain minor amounts of additives such as substances that enhance isotonicity, solubility and/or chemical stability, e.g., buffers, detergents and preservatives. The composition is administered to the site of the injury in a quantity effective for facilitation of the regeneration of injured axons.

The invention further comprises a method for induction and facilitation of the regeneration of injured axons of the central nervous system in a mammal, including humans, comprising administering to the site of injury an effective quantity of the enzymatically-produced dimeric IL-2 of the invention.

Up to now, the most effective approach used to circumvent the oligodendrocyte inhibitory effect has involved the use of antibodies specific to the inhibitors (Schnell and Schwab, 1990). The availability of $TG_N$ opens the way to the preparation of a factor cytotoxic to oligodendrocytes of all species, by incubation of recombinant IL-2 of any species with the enzyme $TG_N$.

It is possible that mammals are deficient not in IL-2 itself, but in the enzyme needed for its posttranslational modification. The enzymatically-produced dimeric TL-2, corresponding to the oligodendrocyte cytotoxic factor, seems to be the reactive form needed in order to eliminate oligodendrocytes from a mature nerve after injury, thereby making the nerve more conducive to axonal growth.

Thus, according to the invention, evidence is provided for a mechanism in which an active factor (IL-2) is converted into a form (enzymatically-produced IL-2 dimer) having a different type of activity. In order to check whether the structure of the dimerized protein plays a role in its conversion into an active factor, or whether any configuration of the dimer (linear, for example) would do, we constructed a defective viral vector of herpes simplex virus (HSV1) that expresses high levels of linear dimerized IL-2 protein. In contrast to the enzymatically-synthesized dimeric IL-2, in which the monomeric protein is converted into a dimeric form by posttranslational modification, the linear dimeric IL-2 protein thus constructed was designed at the transcriptional level and was thus a product of translation. Using this approach, we were able to obtain high levels of a linear dimeric IL-2 protein that was released into the medium following its synthesis, even though the defective virus itself remains in the cells and continues to express the inserted protein.

The linear IL-2 dimer has a different structure from that of the IL-2 dimer produced enzymatically and was then used to show that the cytotoxic property of the protein is a function of its structural conformation. The linear dimeric IL-2 produced by genetic engineering technique retained the biological activity of monomeric IL-2, but failed to exhibit the oligodendrocyte cytotoxic activity exerted by IL-2 dimerized enzymatically, indicating that the conversion of IL-2 into a dimeric form exhibiting a specific type of activity is structurally dependent.

The invention will now be illustrated by the following non-limiting examples.

EXAMPLES

Experimental Procedures a. Preparation of Conditioned Medium (CM) from Fish Optic Nerves For preparation of 300 $\mu$l of CM, four carp (Cyprinus carpio, 800–1200 g, Tnuva, Israel) were deeply anesthetized with 0.05% tricaine methanesulfonate (Sigma). The optic nerves were crushed intraorbitally and the animals replaced in their tank. Eight days later, the fish were reanesthetized, the crushed-regenerating nerves were dissected out, transferred into 300 $\mu$l of serum free medium (DMEM, Gibco) and incubated for 1.5 h at 25° C. The resulting medium, defined as conditioned medium, was then collected, filtered and its protein content determined by the Bradford method (Bradford M., 1976). Aliquots of 50 $\mu$l or 500 $\mu$l were stored at −70° C.

Enzymatic digestion with trypsin was carried out as follows: Trypsin-linked to agarose was equilibrated with PBS and incubated for 4 h at 37° C. with CM. The solution was centrifuged (1000×g, 5 min); at the end of the incubation, the recovered supernatant was tested in vitro in the cultures described below. CM was heat treated at 100° C. for 10 min.

b. Crush Injury of the Rat Optic Nerve

Rats (250–350 g) were anesthetized with Rompum (10 mg/kg, intraperitoneally) and Vetalar (50 mg/kg, intraperitoneally). A lateral canthotomy was performed under a binocular operating microscope and the conjunctiva was incised laterally to the cornea, after separation of the retractor bulbi muscles. The optic nerve was identified and exposed near the eyeball by blunt dissection. The dura was left intact. The nerve was crushed using a calibrated cross-action forceps, 1 mm distal to the eye for a period of 30 sec. The canthotomy was sutured and the animal allowed to recover. At the appropriate time, the animals were reanesthetized and the optic nerves were excised.

c. Preparation of Medium Conditioned by Fish Lymphocytes

Fish were anesthetized with 3-aminobenzoic acid ethyl ester (Sigma). After the carotid artery in the eye cavity was cut, blood was collected from the socket into a tube containing heparin sulphate (100 U/ml; BDH Chemicals). The blood was diluted with an equal volume of phosphate buffered saline (PBS) and allowed to stand for 5 min before being layered on top of the Ficoll or Percoll solutions. Immediately before use, a working solution of 29.4% sodium diatrizoate (Sigma) stock was mixed with 70.6% Ficoll stock, to make a density of 1.06 g/ml. When a Percoll solution was used, a stock solution of Percoll (1.06 g/ml) was made by mixing 44.6 ml Percoll (Pharmacia), 10 ml 100 mM citric acid (Merck), 10 ml 5% bovine serum albumin (BSA; Sigma), and 35.4 ml PBS. Fifteen milliliters of the solution was placed into a 50 ml sterilized Corex (Corning) centrifuge tube. Thirty milliliters of diluted blood were carefully layered on top of the solution with a small pipet. The tubes were capped and centrifuged in swinging buckets at 800×g for 30 min at 20° C.

After centrifugation, white blood cells were found in the interphase, where they could easily be removed using a Pasteur pipet. The white blood cells were collected into a 50 ml tube and washed twice with PBS. The cells were suspended in a small volume of L-15 medium containing penicillin and streptomycin (100 U/ml), and then counted. The cells were diluted to 20×107 cells/ml and 10 ml aliquots were placed into 75 cm2 flasks (Falcon). The flasks were left for 1 h at 20° C. and the nonadherent cells were removed and placed into a second flask. This was repeated, and after 1 h the nonadherent cells were placed into a third flask. The first and second flasks were washed twice with 100 ml of PBS with vigorous shaking. The first flask contained a macrophage enriched culture and the third flask contained a lymphocyte enriched culture. Ten milliliters of medium was added and all flasks were incubated for 8 h, after which time all the supernatants were collected and centrifuged at 2000×g for 5–15 min. The supernatants were then concentrated 25–100- fold in a Centricon or Amicon unit (Amicon Corp.). The samples were then stored at 4° C.

d. Preparation of Rat Brain Oligodendrocyte Cultures and Immunofluorescence Staining For the preparation of enriched oligodendrocyte cultures, neonatal rat brains (2 days old) were excised [2 brains in 2 ml of Leibowitz medium (L-15); Gibco] and chemically dissociated by 3×104 U/ml trypsin (Sigma) in DMEM ($Ca^{2+}$ and $Mg^{2+}$free) containing 1 mM ethylenediaminetetraacetic acid (EDTA). Mechanical dissociation was carried out prior to 10 min incubation at 37° C. with the trypsin solution. The cells were then transferred into 15 ml conical tubes containing 1 ml of solution of 74 U/ml DNase (Sigma), 5200 U/ml soybean trypsin (Sigma) and 3 mg BSA, incubated for 1 min at room temperature, added to 10 ml of medium, and subsequently washed 3 times in DMEM. After the last wash, the cells were suspended in 10 ml DMEM containing 5–10% fetal bovine serum (FBS; Sigma-heat inactivated at 56° C. for 30 min), passed through mesh and seeded in 85 mm2 flasks (Nunc), previously coated overnight at 37° C. with 20 µg/ml poly-L-lysine (PLL, MW 100000; Sigma). The medium was changed first twenty-four hours after cell seeding and then once every 2–3 days thereafter. On the 8th day after seeding, the cells were incubated with shaking for 4–6 h, the supernatant was removed and the remaining cells further incubated in 10 ml medium (DMEM plus 5–10% FBS) for several hours followed by an overnight shaking. The cells that were removed by the shaking were collected and centrifuged, and the pelleted cells were then resuspended in 1–2 ml of serum-free medium (Bottenstein, J. E. et al., (1979) Proc.Natl.Acad. Sci.U.S.A. 76, 514–517).

The thus obtained enriched oligodendrocyte cultures recovered cells were seeded on glass coverslips (13 mm; 3×105 cells/well) previously coated with PLL (20 µg/ml), The glass coverslips were placed in a 24-well plate (Nunc). During seeding, 50 µl of cell suspension was initially applied to each coverslip and left for 30 min at 37° C., to allow attachment. Subsequently, the cells were washed with DMEM and then 500 µl of defined medium (Raff's modification to Bottenstein's and Sato's defined medium) was added. After 48 h, the seeded cells were treated with the conditioned medium or with conditioned medium preincubated for 2 h either with rabbit anti-human IL-2 antibodies (Genzyme, Inc.) or with control antibodies (rabbit antineurofilaments). The number of mature oligodendrocytes, i.e., galactocerebroside (GalC) positive cells, was determined by immunofluorescence as follows: Cells were thoroughly washed with Hank's balanced salt solution (HBSS) containing 2% FBS, heat inactivated and incubated for 30 min at 37° C. with 50 µl of the monoclonal anti-GalC antibodies (IgG3, hybridoma supernatant diluted 1:5 in DMEM, Serotec). At the end of the incubation, the cells were washed and further incubated with 50 µl of fluorescein-conjugated goat anti-mouse IgG3 (1:50 in DMEM), and then washed and fixed in methanol for 10 min at −20° C. At a final washing the cells were coated with glycerol containing 22 mM 1,4-diazobicyclo(2,2,2)octaine. As controls, coverslips were used which underwent the same staining procedure, except for the primary antibodies which were omitted. Coverslips were placed on the glass slides, sealed with nail polish and stored at 4° C. Cells were counted over the entire coverslip.

e. Western Blot Analysis of IL-2 Immunoreactive Proteins

Samples were electrophoresed on SDS-PAGE. The gel was blotted onto nitrocellulose for 2 h at 200 mA. The nitrocellulose was incubated for 2 h at 37° C. with PBS containing 5% milk, and then washed in PBS.

The blot was incubated with rabbit anti-IL-2 antibodies for 2 h at 37° C., then washed three times, 5 min each time, in PBS containing 0.05% Tween-20. Finally, the blot was incubated for 2 h at 37° C. with [125I]-labeled goat anti-rabbit antibodies (106 cpm/ml), washed three times with PBS containing 0.05% Tween-20, dried and autoradiographed.

f. Preparation of Cultures from Injured Adult Rat Optic Nerves

To prepare the glial cell cultures, in each experiment, five adult rat optic nerves were used. The optic nerves were crushed as described above, and 3 days later they were excised, minced and incubated in Leibowitz L-15 medium (Gibco) containing 500 U/ml collagenase (Sigma). After 60 min at 37° C., an equal volume of trypsin (30000 U/ml) was added for additional 15 min. The suspension was centrifuged (500×g, 5 min), the supernatant was removed and the tissue was then resuspended and further treated for 15 min with trypsin (15000 U/ml) in a solution containing EDTA 0.25 mM in $Ca^{2+}$- and $Mg^{2+}$- free DMEM. The digestion was terminated by addition of an equal volume of solution of soybean trypsin inhibitor (5000 U/ml, Sigma), bovine pancreas DNAse 1 (74 U/ml, Sigma), bovine serum albumin (BSA, fraction V, 3 mg/ml, Sigma), followed by centrifugation. The supernatant was replaced with Raff's modification (Raff et al., 1983) of Bottenstein's and Sato's defined medium (Bottenstein and Sato, 1978), followed by trituration of the tissue. Fifty µl of the resulting cell suspension was plated onto each poly-L-lysine (PLL, 20 µg/ml) coated coverslip (cells from one optic nerve were seeded on 3 coverslips). After 30 min at 37° C., the adherent cells were rinsed and 500 µl of defined medium was added. CM from regenerating fish optic nerves (12 µm/ml) were added to experimental samples 48 h later. The cells were examined after additional 48 h, by indirect immunofluorescence labeling.

g. Cell Cultures from Newborn Rat Brain

Glial cells were prepared from cerebral cortex of newborn Sprague-Dawley rats (McCarthy and DeVellis, 1980). Cells were plated into PLL-coated flasks (85 mm2, Nunc) or onto PLL-coated coverslips (105 cells/coverslip), for analysis of mixed glial cell cultures. The cells were grown in DMEM supplemented with 5% fetal bovine serum (FBS, Sigma), that was changed every 2 days.

h. Preparation of Enriched Oligodendrocyte Cultures

After 8 days in vitro, the flask containing mixed populations of glial cells of newborn rat brains was shaken overnight, the nonadherent cells were plated onto PLL-coated coverslips at approximately 104 cells/coverslip, unless otherwise specified. The cells were allowed to adhere for 30 min and were then fed with Raff's modification of Bottenstein and Sato's defined medium, in order to encourage oligodendrocyte development. Cells were treated at different time periods after seeding and were subjected to indirect-immunofluorescence staining or ELISA, usually after 48 h, unless otherwise specified.

i. Indirect Immunofluorescence Labeling

Cultured cells were immunolabeled with the following antibodies: A2B5 mouse IgM monoclonal antibodies (hybridoma supernatant, diluted 1:1), which label mature type-2 astrocytes and perinatal progenitors of both oligodendrocyte and type-2 astrocyte (O-2A perinatal progenitors) (Eisenbarth et al., 1979; Raff et al., 1983); O4 mouse IgM monoclonal antibodies (concentrated hybridoma supernatant, diluted 1:100), which label immature oligodendrocytes (Sommer and Shachner, 1981) and O-2A adult progenitors (ffrench-Constant and Raff, 1986a); mouse antigalactocerebroside (Galc) monoclonal antibodies (hybridoma supernatant, diluted 1:10), which label mature oligodendrocytes (Raff et al., 1978); rabbit anti-glial fibrillary acidic protein (GFAP, whole sera, diluted 1:1000), which label mature type-1 and type-2 astrocytes (Bignami et al., 1972); mouse monoclonal antibodies 6D2 which label fish oligodendrocytes (Jeserich and Romen, 1989). Rhodamine- or fluorescein-conjugated second antibodies were purchased from different sources: goat anti-mouse IgM (diluted 1:50, Jackson Immunoresearch Laboratories); goat anti-mouse IgG3 (diluted 1:50, Serotec); swine anti-rabbit IgG (diluted 1:50, Dakopatts).

Immunolabeling of surface antigens (A2B5, O4 and Galc) was carried out first by incubating each of the required antibodies with the cells in 50 $\mu$l volume at 37° C. for 30 min. Cells were then washed several times with Hank's balanced salt solution containing 2% heat-inactivated FBS, and further incubated for 30 min in the appropriate rhodamine- or fluorescein-conjugated second antibodies diluted in DMEM. The cells were washed and fixed in methanol at -20° C., for 10 min. For intracellular antigens (GFAP), cells were first fixed and then immunolabeled. In some experiments, cultures were double labeled simultaneously with A2B5 and Galc antibodies, followed by anti-mouse IgM (rhodamine) and anti-mouse IgG3 (fluorescein). In all cases, after the immunolabeling, the coverslips were washed, mounted in a drop of glycerol containint 22 mM of 1,4-diazobicyclo(2,2)octaine (Sigma), to prevent fading, sealed and examined in a Zeiss Universal microscope equipped with phase contrast, epifluorescence (for rhodamine and fluorescein detection) optics and camera. The concrete number of all immunolabeled cells were counted in all coverslips.

j. ELISA on Living Cells

Cultures enriched for oligodendrocytes were prepared as described above. The cells were seeded in multiwell microtiter plates (5×103 cells/well, Nunc). After 24 h in vitro, CM derived from either regenerating nerves or intact nerves were added at the indicated concentrations. Forty-eight hours later, the cells were examined by incubating with Galc antibodies at 37° C. for 30 min, followed by horseradish peroxidase conjugated to goat anti-mouse antibodies (BioMakor, Israel), for additional 30 min at 37° C. Determination of the amount of bound antibodies was obtained by washing the cells and adding 100 $\mu$l of substrate [2,2-azino-di(3-ethylbenzthiazoline)sulphate, Sigma], supplemented with 0.003% H2O2 to each well. Absorption was recorded in a Titertech Multiskan MMC at 405 nm, with a reference wavelength of 630 nm.

k. Nonspecific Esterase Staining

Cells were stained using the $\alpha$-Naphthyl Acetate Esterase procedure, as well as the fluoride inhibition procedure using a Sigma kit. Sodium nitrate (50 $\mu$l; 0.1 M) was added to 50 $\mu$l fast-blue (15 mg/ml in 0.4 M HCl). The mixture was left for 2–3 minutes at room temperature. To this, 2 ml deionized water at 37° C. was added, followed by 250 $\mu$l Trizmal 7.6 buffer concentrate, followed by 50 $\mu$l $\alpha$-Naphthyl Acetate solution. For fluoride inhibition, 50 $\mu$l sodium fluoride (0.2 g/ml) was also added. Cells were then fixed in a citrate-acetone-formaldehyde fixative (25 ml citrate solution plus 65 ml acetone plus 8 ml of 37% formaldehyde) for 30 sec at room temperature. The cells were then washed thoroughly in water, after which they were incubated for 30 min with the $\alpha$-Naphthyl Acetate reaction solution at 37° C. After being thoroughly washed, the cells were counterstained for 2 min with Hematoxylin solution. The coverslips were then washed and mounted on microscope slides with glycerol for observation.

l. Statistical Analysis

The statistical analysis of the results was performed using the Friedman Rank Test. In this statistical test each experiment is treated as a separate block, and the significant difference of the results (control vs CM-treated) is found, according to the number of blocks.

Example 1

This example shows that media conditioned by regenerating fish optic nerves containing OCF cause reduction in process-bearing oligodendrocytes in cultures of dissociated injured adult rat optic nerves.

FIG. 1$a,b$ shows process-bearing O4 positive cells in cultures derived from adult rat optic nerves, which had been injured 3 days prior to their removal. In the presence of conditioned media (CM) derived from regenerating fish optic nerves (CM-R;12 $\mu$g protein/ml) added to these cultures 48 h after seeding, the number of O4 positive cells that appeared at 96 h in vitro (FIG. 1$c–g$) was much lower than in non-treated cultures kept in the control medium (FIG. 1$a,b$) The O4 positive cells which remained in the CM-R treated cultures had few processes and were therefore, identified as immature oligodendrocytes (FIG. 1$c–g$). The same results were obtained when the same experiment was repeated using antibodies directed to mature oligodendrocytes, such as antigalactocerebroside (Galc) rather than O4 antibodies. Accordingly, in cultures treated with CM of fish regenerating nerves (CM-R), only 42% of the cells developed into mature Galc positive cells out of the total Galc positive cells in the defined medium. These results suggest the presence of soluble factor(s) in media conditioned by regenerating fish optic nerve, which may be cytotoxic and/or may inhibit maturation of oligodendrocytes from their progenitors.

Example 2

This example shows that the media conditioned by regenerating fish optic nerves containing OCF affect maturation of Galc positive cells in newborn rat cultures of oligodendrocytes.

In order to further study the nature of this inhibitor/cytotoxic factor and its possible implication for regeneration, we first looked for a richer source of oligodendrocytes and examined the possibility of using cultures of newborn rat brains instead of injured adult rat optic nerves, as they provide a rich source and a more homogeneous population of oligodendrocytes.

Newborn rat brain oligodendrocytes and their perinatal progenitors were obtained in the following set of experiments by the method of McCarthy and DeVellis, 1980. The oligodendrocytes were seeded on poly-L-lysine coated coverslips. CM of regenerating fish optic nerves (CM-R) were added to these cultures (12 $\mu$g/ml) enriched with newborn rat brain oligodendrocytes either at the time of seeding or 24 h and 48 h later. In all cases, the same number of oligodendrocytes were seeded as in control untreated cultures. As can be seen in FIG. 2, in all CM-treated cultures 24 h subsequent to the CM application, the number of multiprocessed Galc positive cells was lower (about 50%) than in matched non-treated cultures. It appears that if the CM affects only maturation of oligodendrocytes from their progenitors, the low number of Galc positive cells observed, at least in cultures treated 24 h or 48 h after seeding, might be a reflection of spontaneous cell death under conditions in which cell renewal from progenitors is inhibited. Alternatively, the CM of the regenerating fish optic nerve might affect mature oligodendrocytes in addition to its effect on progenitors. Also shown in FIG. 2, is the dependency of the inhibitory effect on the amount of the applied CM. Thus, while 12 μg protein/ml were effective, 1.2 μm protein/ml were ineffective. As shown in Table I, 24 h after CM-R application, the number of process-bearing Galc positive cells was already lower by 40.3±6.4, relative to their number in untreated control cultures (Table I). Boiling the CM-R or treating it with trypsin resulted in a diminution of their inhibitory/cytotoxic effect (Table II), thus suggesting that the factor has a protein nature.

TABLE I

CM-R cause a reduction in the number of rat brain oligodendrocytes

| Type of* cells | Hours** of post-treatment | % of control*** (mean ± SD) | Number of experiments (n) |
| --- | --- | --- | --- |
| Oligodendrocytes | 24 | 40.3 ± 6.4 | 3 |
| Oligodendrocytes | 48 | 14.4 ± 10.4 | 12 |
| Mixed glial cells | 48 | 25.7 ± 4.7 | 4 |

*In these experiments, the number of counted oligodendrocytes (Galc positive cells) in control cultures per coverslip was between 350–1700 cells.
**CM-R at 12 μg protein/ml was added.
***The percentage of inhibition was calculated in each experiment by taking the number of counted cells in control, nontreated cultures, as 100%.

TABLE II

The inhibitory/cytotoxic effect of CM-R on oligodendrocytes is heat and trypsin labile

| Treatment | Number of Galc positive cells (mean ± SEM) |
| --- | --- |
| Control | 1427 ± 247 |
| CM-R | 361 ± 17* |
| CM-R (boiled) | 1474 ± 70** |
| CM-R (trypsin treated) | 1087 ± 10** |

In this experiment, rat brain oligodendrocytes were cultured as in FIG. 2. At 24 h after plating, CM-R (boiled or trypsin treated, 20 μg/ml) was added. Forty-eight hours after the addition of CM-R, the number of Galc positive process-bearing cells was determined by counting immunofluorescent cells. The results of one experiment, carried out in triplicate, are given. These results were reproduced in two additional experiments.
*p-value = 0.025.
**No significant differences were observed between control cultures and cultures treated with boiled or trypsinized CM-R.

Example 3

This experiment shows that the inhibitory/cytotoxic activity of OCF is associated with regeneration in the fish optic nerves.

Figure 3:
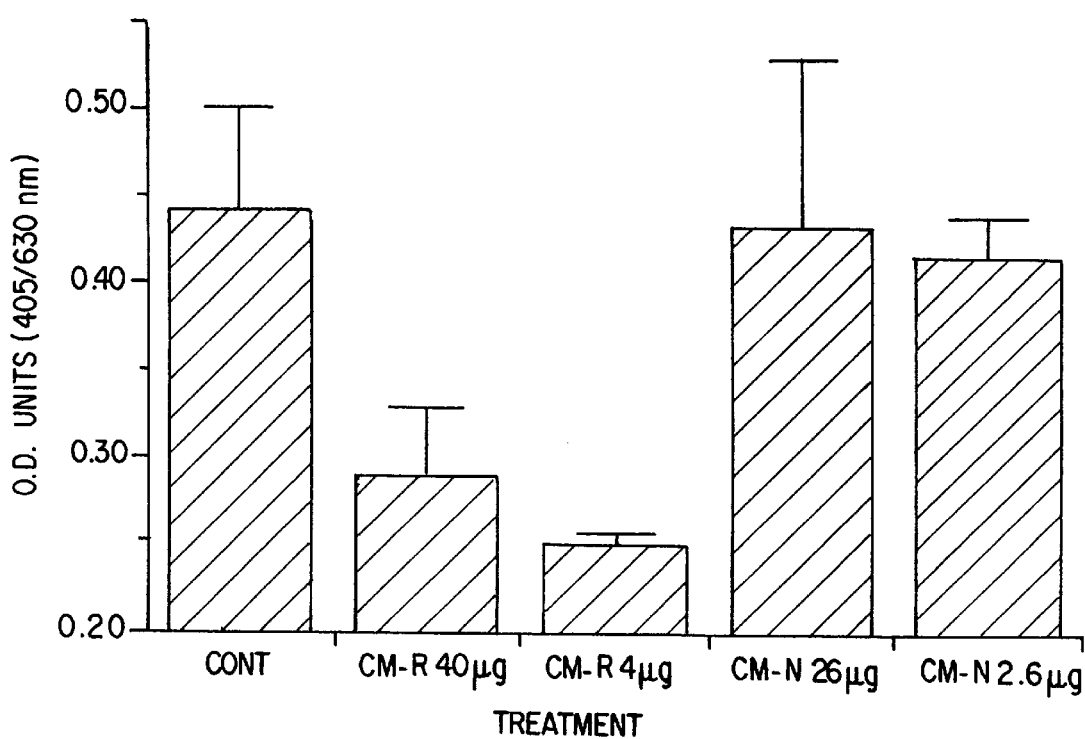
FIG. 3A shows a comparison between the effect of CM-R and CM-N on development of Galc positive cells in cultures of neonatal rat brain oligodendrocytes. Cultures of oligodendrocytes were prepared as above, and seeded in multiwell (103 cells/microtiter plate). After 24 h in vitro, CM-R or CM-N were added at the indicated concentrations. Forty-eight h later, the cells were examined by incubating first with Galc antibodies at 37° C. for 30 min, followed by horseradish peroxidase conjugated to goat anti-mouse antibodies (HRP-GaM, Bio-Makor, Israel), for additional 30 min at 37° C. Determination of the amount of bound antibodies was obtained by washing cells and adding 100 ul of substrate (2,2'-azino-di(3-ethylbenzthiazolinesulphate) (Sigma) to each well. Absorption was recorded in a Titertech Multiskan MMC at 405 nm, with a reference wavelength of 630 nm.
FIG. 3B shows results obtained by counting the number of Galc positive cells per coverslip in cultures treated with either CM-R (12 μg/ml) or CM-N (12 μg/ml) added at 24 h in vitro and examined 48 h later for comparison with FIG. 3A.
Figure 3A:
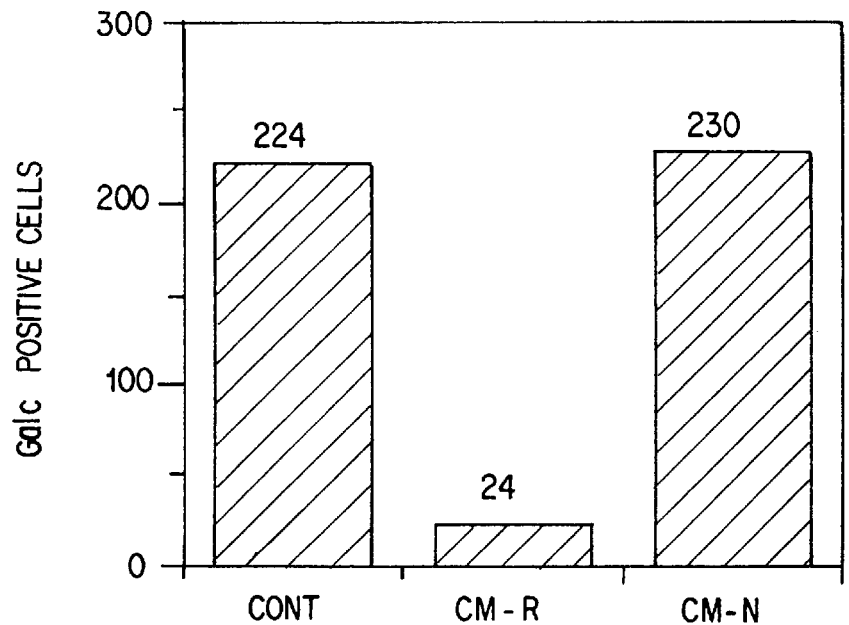

In order to find out whether the level or activity of the inhibitory/cytotoxic factor are correlated with regeneration of the fish optic nerves, we compared the effect of the CM-R with that of media conditioned by non-injured normal fish optic nerves (CM-N). CM-R or CM-N, at the same protein concentrations, were added to newborn rat brain oligodendrocytes 24 h after seeding. The resultant effect was monitored with anti-Galc antibodies, using counts of Galc positive cells labeled by indirect immunofluorescence. FIG. 3 compares the number of Galc positive cells in CM-N treated cultures relative to their number in CM-R treated culture. The effect of CM-N was lower i.e., non-injured nerves lacked inhibitory activity on maturation of oligodendrocytes.

Example 4

This experiment shows that OCF comprised in CM-R does not mimic the effect of PDGF.

Differentiation of oligodendrocytes has recently been shown to be regulated by platelet-derived growth factor (PDGF) (Noble et al., 1988, Raff et al., 1988 and Richardson et al 1988). Addition of PDGF to cultures of oligodendrocyte progenitors transiently delays their differentiation, due to its mitogen activity.

Figure 4C:
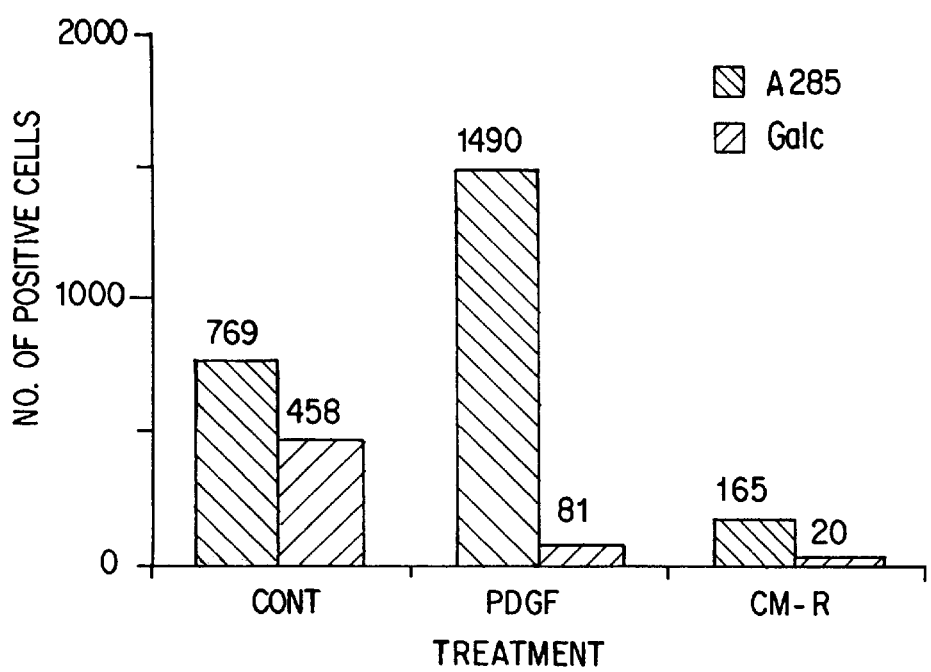
FIG. 4C shows a bar graph showing the concrete counted number of A2B5 or Galc positive cells in the coverslips of each of the protocols according to FIGS. 4A and 4B and FIG. 4D, below (space bars=μm)
Figure 3A:
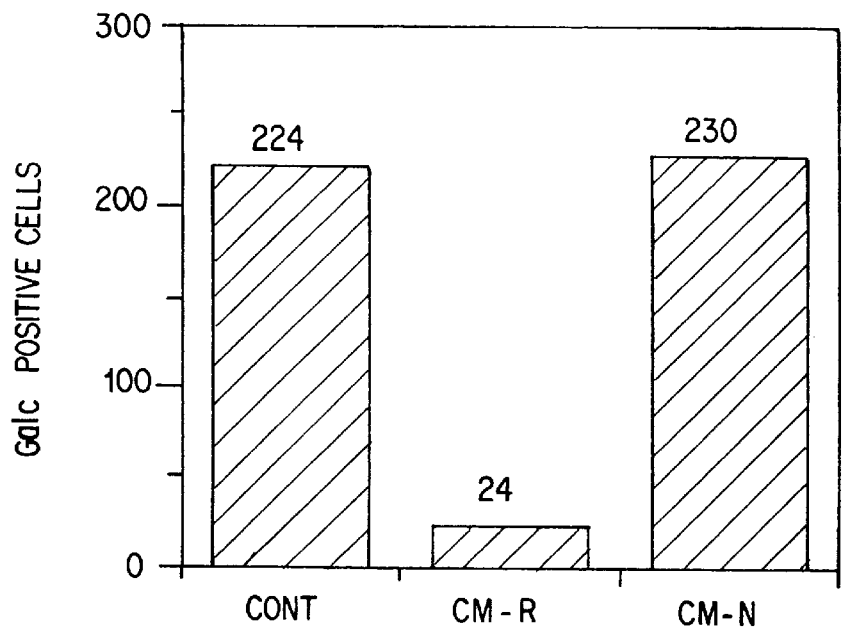
Figure 4C:
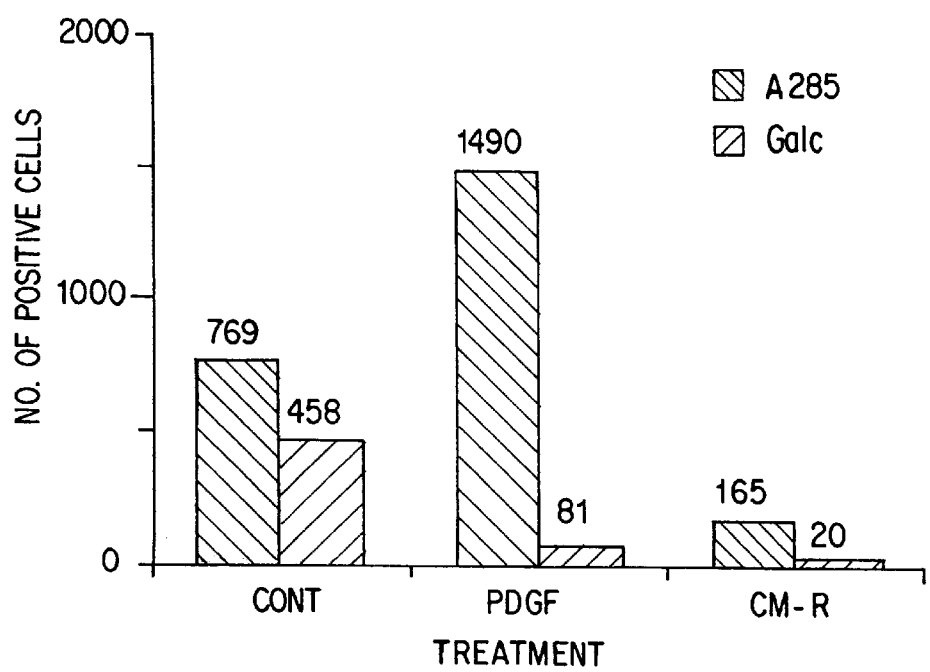
Figure 5:
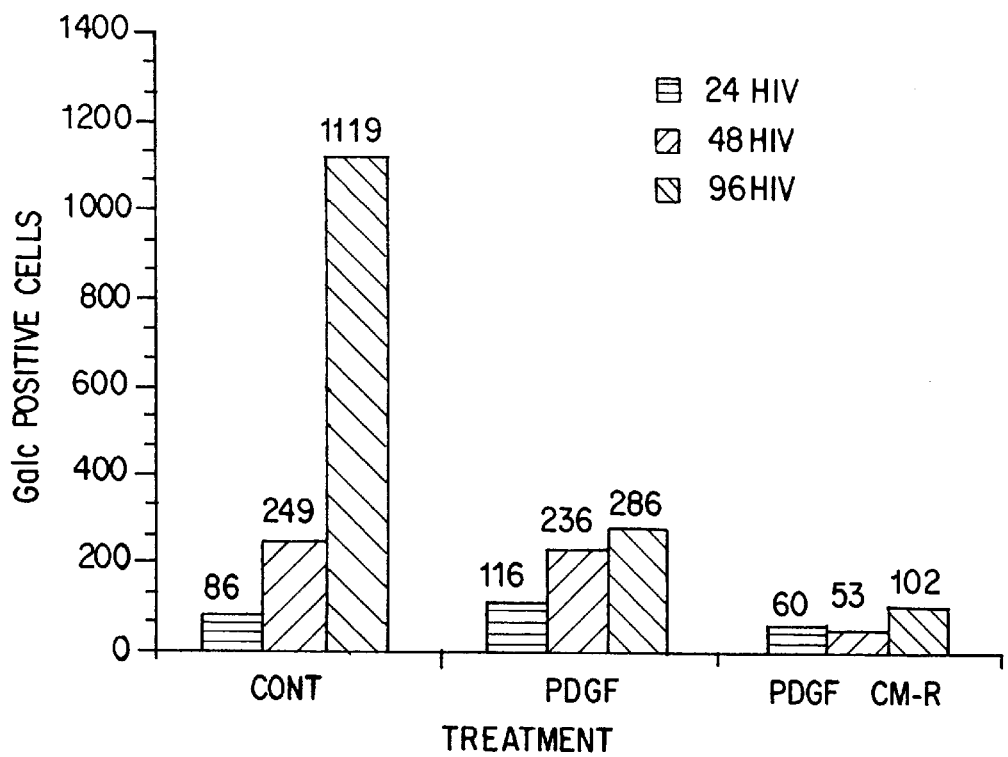
FIG. 5 shows the effect of combined application of CM-R and PDGF on development of Galc positive cells. Cultures of brain oligodendrocytes were prepared as in FIGS. 2 and 3. PDGF (5 ng/ml) or PDGF together with CM-R (5 ng/ml and 12 μg/ml, respectively were added to neonatal rat brain oligodendrocytes 24 h after seeding. At the indicated subsequent time (24, 48, 96 h), cultures were stained for Galc positive cells. The numbers represent the absolute number of Galc positive cells per coverslip. Note the reduction in the number of Galc positive cells when treated with a combination of PDGF and CM-R.
Figure 6B:
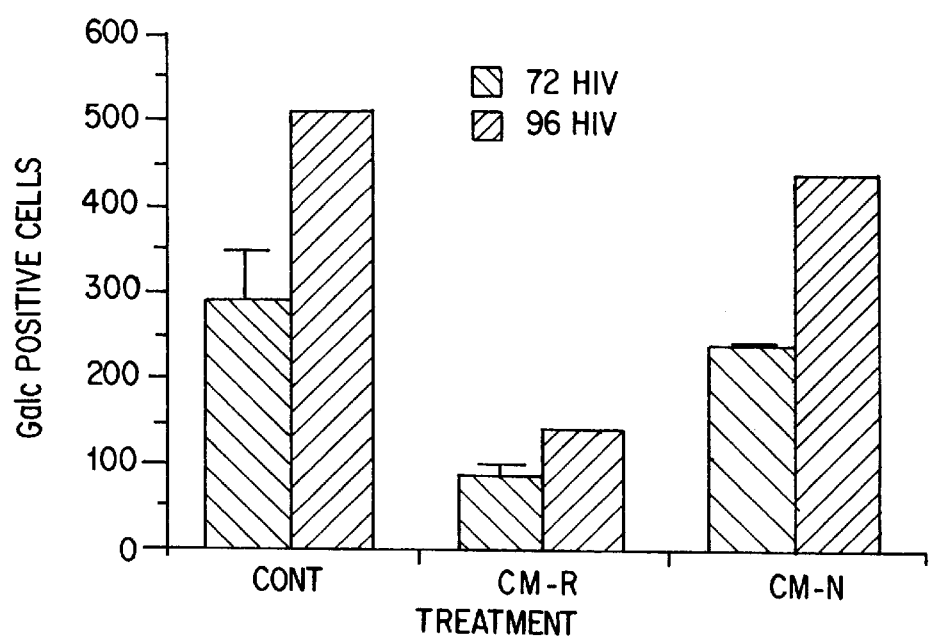
FIG. 6B shows the number of Galc positive cells in the coverslips of each treatment according to the protocol in FIG. 6A, at 72 and 96 h in vitro; The results represent mean±SD of 2 coverslips.
Figure 6A:
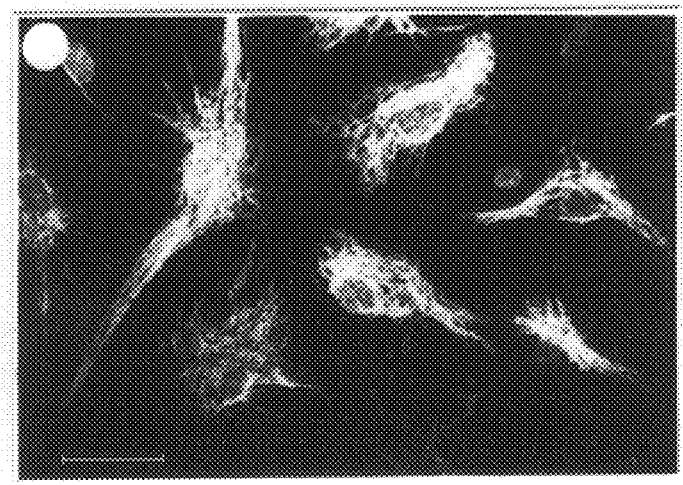
FIG. 6A shows that CM-R selectively affect oligodendrocytes in mixed newborn rat cultures of astrocytes and oligodendrocytes. Mixed glial cells were dissociated from newborn rat brains, as described in FIG. 2, and were immediately seeded on poly-L-lysine coated coverslips (104 cell/coverslip). These cells were kept for 6 days in vitro in DMEM supplemented with 5% FCS, that was changed every 2 days. At day 6, the medium was changed into defined medium and supplemented with either CM-R (10 μg/ml) or CM-N (10 μg/ml). At 72 and 96 h in vitro, the cells were double labeled with mouse monoclonal antibodies against Galc and rabbit anti-GFAP, followed by specific rhodamine conjugated goat anti-mouse IgG3 and fluorescein conjugated goat anti-rabbit, respectively. The fluorescent micrograph shows cells stained with anti-GFAP and unaffected by CM-R treatment, after 72 h in vitro.
Figure 6C:
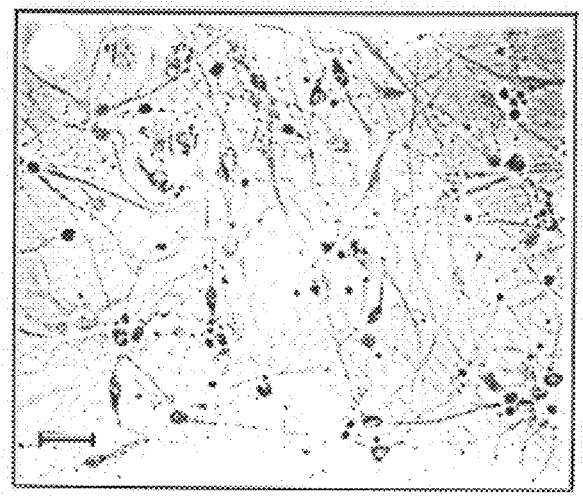
FIG. 6C is a phase micrograph of typical mixed glial cells of CM-R treated cultures according to the culture of FIG. 6A. Note that the monolayer formed by non-CM-R sensitive cells are stained with GFAP.
Figure 6D:
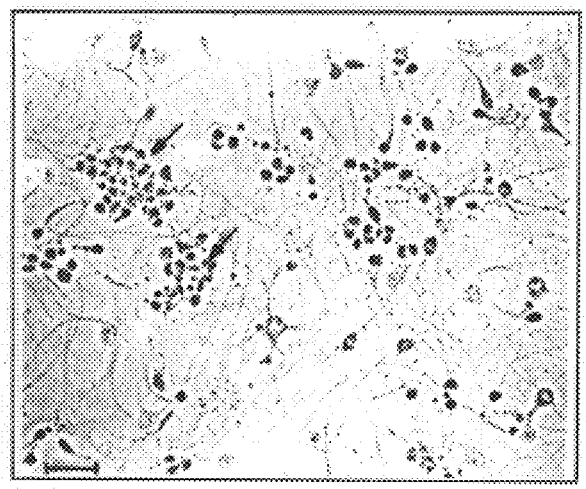
FIG. 6D is a phase micrograph of untreated cultures according to the protocol of FIG. 6A. The CM-R sensitive cells in the control form clusters, marked by arrows, and are stained with A2B5 (data not shown). These cells probably represent the 0–2A progenitors that are stimulated to proliferate by the monolayer forming type-1 astrocytes.

To get an insight as to the possible mechanism underlying the observed inhibition, at least that related to the maturation of oligodendrocytes from their progenitors, we compared activity of CM of regenerating fish optic nerves (CM-R) to that of PDGF. Addition of PDGF to brain cultures at the time of seeding, resulted in an apparent reduction in the number of Galc-positive cells at 48 h in vitro. However, the effect was markedly less as compared with that of the CM-R (FIG. 4). The apparently lower number of Galc positive cells observed in PDGF-treated cultures relative to control nontreated cells was a reflection of the proliferation of their progenitors, stained with A2B5 antibodies. This was evident from the increased number of A2B5-positive cells in PDGF-treated cultures. As can be seen in FIG. 4, in PDGF-treated cultures, as expected, there was an increase in the number of 0-2A progenitors, stained with A2B5 antibodies (FIG. 4a, b, c). In contrast, in CM-treated cultures there was a reduction in the number of A2B5 positive cells (FIG. 4c, d). These results suggest that CM-R affect not only adult oligodendrocytes, but also their progenitors. These observations rule out the possibility that the observed effect of the CM-R on the development of Galc positive cells from their progenitors is mediated by PDGF or any other mitogen. This is further supported by FIG. 5, which shows that addition of CM-R together with PDGF resulted in a reduction of Galc positive cells, as would be expected from the application of CM-R only.

Ciliary neurotrophic factor (CNTF) is another factor which has recently been shown to be effective in 0-2A cell lineage by inducing type-2 astrocyte differentiation and thereby indirectly causing a reduction in the number of mature Galc positive oligodentrocytes Lillien et al., 1988). Since the CM-R did not cause an increase in the number of cells stained with A2B5 antibodies, and thus did not increase either progenitors or type-2 astrocytes, it is unlikely that the CM-R effect is mediated via CNTF.

Example 5

This experiment shows the specificity of the inhibitory/cytotoxic effect of OCF on oligodendrocytes by media conditioned with regenerating fish optic nerves.

In order to examine whether the observed inhibitory/cytotoxic effect of the CM is unique to oligodendrocytes, we applied the CM-R to a mixed population of astrocytes and oligodendrocytes.

FIG. 6 shows that the observed inhibitory effect is not due to a non-specific toxic effect but is rather selective to oligodendrocytes. Cultures of mixed population of glial cells, dissociated from newborn rat brain, were treated with either CM of regenerating, or of intact nerves (CM-R and CM-N, respectively). Such conditions are the most favorable for differentiation of oligodendrocytes seeded onto the monolayer formed by the astrocytes. Even under these conditions, the inhibitory effect of the CM-R was pronounced, whereas the CM-N had only a marginally inhibitory activity at 72 and 96 h in vitro (FIG. 6b). In contrast to the inhibitory effect of the regenerative CM on oligodendrocytes, the survival and differentiation of non-oligodendrocyte cells, which were present in the these mixed cultures and stained with glial fibrillary acidic protein (a marker for astrocytes) were not affected by the CM-R (FIG. 6a). The apparent density of the monolayer of astrocytes formed in treated and non-treated cultures was similar (FIG. 6c vs. FIG. 6d). The observed inhibitory effect of the CM-R is therefore not due to a non specific toxic effect, but is rather selective to oligodendrocyte lineage (FIG. 6).

Example 6

These experiments show that there is an inverse relationship between the numbers of oligodendrocytes and macrophages.

In the first experiment, common goldfish were used. The conditioned media was prepared with Dulbecco's modified Eagle's medium (DMEM, 4 optic nerves per 300 μl/medium).

Comparison between the cell populations obtained after dissociation of nerves which were kept in organ culture and those of the regularly crushed nerves (i.e., OC-3 and PC-3 in rat and OC-2 and PC-2 in fish) might indicate whether the postinjury behaviour of these cells is intrinsic to the optic nerve, or whether it is affected by some external factor, such as the blood monocytes. Any such external factors would be absent in the organ cultures, since the optic nerve is taken out at the time of injury.

In cultures of dissociated fish optic nerves which were organ cultured for 2 days prior to dissociation (OC-2 cultures), a relatively high number (65 cells per coverslip) of oligodendrocytes (6D2 positive cells) was observed, but only few macrophages were seen. In contrast, in cultures of dissociated optic nerves which were excised 2 days after their lesion (PC-2 cultures), many macrophages developed, but only few oligodendrocytes. The few oligodendrocytes which were seen in cultures of crushed nerves (PC-2) were much smaller, and had much shorter processes than the oligodendrocytes in the OC-2 cultures. These results are summarized in Table III.

In parallel to the appearance of the oligodendrocytes in the dissociated cells of the organ cultured nerves, there was a complete absence of macrophages or macrophage-like cells in these cultures. Even after 7 days in culture none of these cells were seen (by this time, in PC-2 cultures these cells reach an enormous size).

TABLE III

The number of oligodendrocytes in dissociated cultures of fish optic nerves which had been crushed 2 days prior to excision and dissociation (PC-2 cultures), and in cultures of fish optic nerves which had been organ cultured for 2 days prior to dissociation (OC-2 cultures)[1]

| | No. of oligodendrocytes | | | |
|---|---|---|---|---|
| Culture | Exp. 1 | Exp. 2 | Exp. 3 | Mean ± SD |
| OC-2 | 65 (±3) | 93 (±25) | 40 (±12) | 66 (±26) |
| PC-2 | 3 (±1) | 2 (±1) | 15 (±5) | 7 (±6) |

Within each experiment, the same number of fish, of approximately equal size, was taken for the PC-2 and for the OC-2 cultures. Also, the cells were finally seeded on an equal number of coverslips. In this way, variations due to the experimental procedure were reduced to the minimum. Each experiment was carried out in triplicate. The total number of oligodendrocytes (6D2 positive cells) on the coverslips was counted, and the numbers given are the averages of three trials.

Unlike the situation in the fish, in the rat the number of mature oligodendrocytes that was observed in cultures of injured nerves and of organ cultured nerves was similar. In cultures of rat optic nerves, which were organ cultured for 3 days (OC-3 cultures), three main populations of cells were observed. Similarly to cultures of crushed rat optic nerves (FIG. 3), a large proportion of these cultures were process-bearing oligodendrocytes which were labeled by Galc after 96 h in culture, and comprised nearly 40% of the total cell number. Another large population of cells (about 40%) morphologically resembled macrophages.

In the following experiments, goldfish optic nerve cells were grown either in L-15 Leibowitz medium supplemented with 1–2% FCS, or in L-15 medium supplemented with the same additives used in Raff's modification of Bottenstein and Sato defined medium, plus 1–2% FCS. Organ culture of fish optic nerves was performed in L-15 medium supplemented with the same additives used in Raff's modification of Bottenstein and Sato defined medium, plus 1–2% FCS.

Medium conditioned by regenerating goldfish optic nerves (CM) was prepared similarly to the CM-R determined above by incubating segments of goldfish optic nerves, removed 8 days after crush, in L-15 medium (10 goldfish optic nerves per 500 μl of medium for 3 h at room temperature).

Figure 7A:
FIG. 7A shows blood-borne macrophages in the fish optic nerve cultures. These macrophages were most abundant in cultures of nerves which were injured several days prior to their excision. The cells seen here were grown in L-15 medium supplemented with 10% FCS. The Figure shows a macrophage 7 days after plating, Giesma stained, and seen in phase contrast.
Figure 7B:
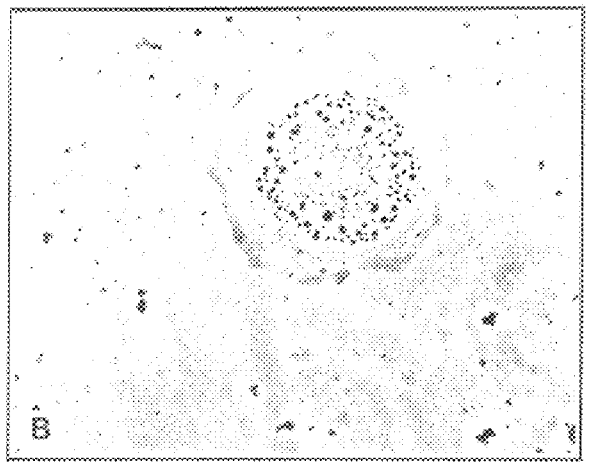
FIG. 7B shows cells 5 days after plating, according to the protocol of FIG. 7A, in phase contrast after fixation.
Figure 7C:
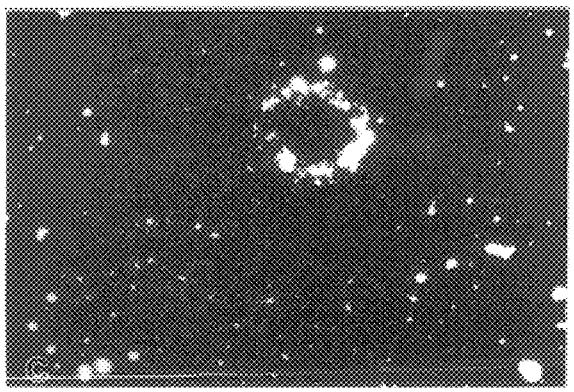
FIG. 7C shows cells 5 days after plating, according to the protocol of FIG. 7A, 6D2 labeled, after fixation. It is worth noting that the figure shows the myelin-loaded vacuoles of the macrophage. These vacuoles were also stained positively with nonspecific esterase (FIG. 8). All micrographs are 500×.
Figure 8A:
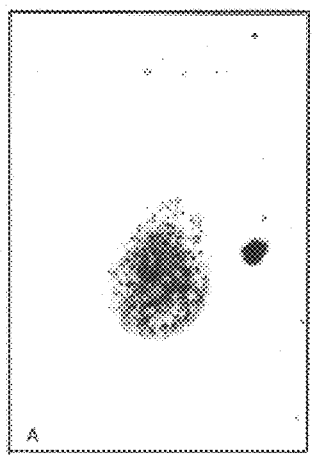
FIG. 8A shows macrophages positive for nonspecific esterase. Goldfish optic nerve cells were grown as described. The figure shows macrophages which are presumably blood-derived. These were rare in cultures of fish optic nerves which were organ cultured prior to their dissociation, but were abundant in cultures of fish optic nerves which were crushed a couple of days prior to their excision. These macrophages were typically circular in shape and their vesicles were also typically arranged in a circular fashion. These vesicles were 6D2-positive (FIGS. 7 B,C), which is indicative of the myelin phagocytosis activity of these cells.
Figure 8B:
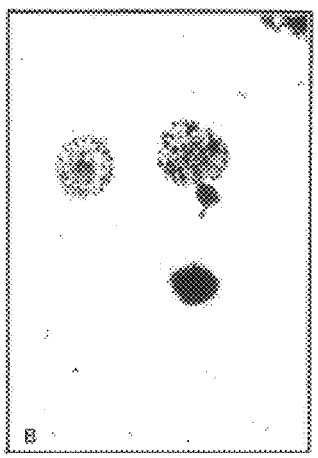
FIG. 8B shows macrophages which are presumably blood derived according to the protocol of FIG. 8A. These macrophages also show some of the characteristics of those in FIG. 8A.
Figure 8C:
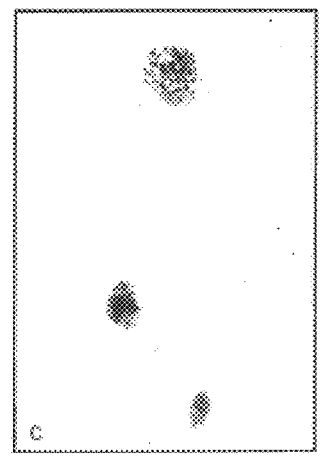
FIG. 8C shows macrophages which are presumably blood derived according to the protocol of FIG. 8A. These macrophages also show some of the characteristics of those in FIG. 8A.
Figure 8D:
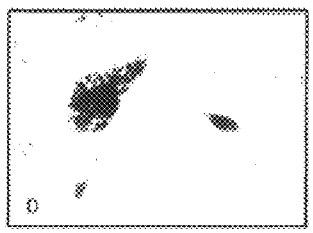
FIG. 8D shows resident macrophages from FIG. 8A. A variety of shapes was observed, ranging from long to more round in appearance. The vesicles of these cells were distributed throughout the cytoplasm, and were also 6D2-positive.
Figure 8E:
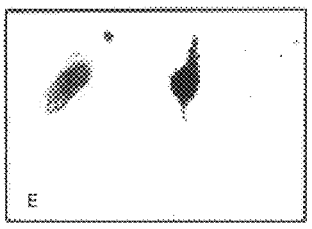
FIG. 8E shows resident macrophages from FIG. 8A. A variety of shapes was observed. The vesicles of these cells were distributed throughout the cytoplasm, and were also 6D2-positive.
Figure 8F:
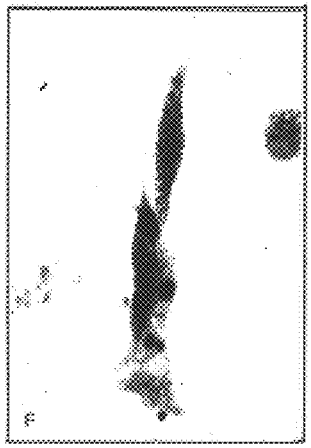
FIG. 8F shows resident macrophages from FIG. 8A. A variety of shapes was observed, ranging from long to fibroblast-like. The vesicles of these cells were distributed throughout the cytoplasm, and were also 6D2-positive.
Figure 8G:
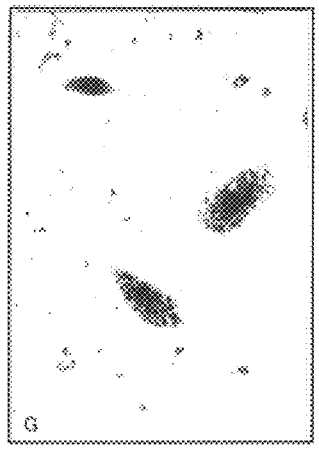
FIG. 8G shows resident macrophages from FIG. 8A. A variety of shapes was observed, ranging from long to more round in appearance. The vesicles of these cells were distributed throughout the cytoplasm, and were also 6D2-positive.

The macrophages in the fish cultures included blood-derived as well as resident macrophages. The two types of macrophages were distinguishable by morphological criteria: the blood-derived macrophages were typically circular and their vesicles were also arranged in a circular manner; the resident macrophages, on the other hand, were irregular in shape and their vesicles were distributed randomly through the cytoplasm. Moreover, cells which were reminiscent of the blood-derived macrophages (FIG. 7) were abundant in cultures of optic nerves excised several days after a crush injury, but were rare in cultures of optic nerves organ cultured after the excision. Both macrophage types actively phagocytozed myelin debris, as evidenced by the 6D2-labeled vacuoles on prefixed cells (the vacuoles did not label by any other antibody used, nor by the second antibody itself). The apparently blood-derived macrophages grew best when the medium was supplemented with 10% FCS, and after a week in culture they grew to very large dimentions, compared to the other cells in the culture (FIG. 7A). FIG. 7C shows a macrophage whose vacuoles are heavily labeled by the 6D2 antibody. These macrophages were also positively stained with nonspecific esterase (FIG. 8A–C).

The cells which were considered as resident macrophages appeared in many forms, but could be divided into two major groups: those with a straight, fibroblast-like appearance (FIG. 8F and FIG. 9E), and those which were rounder and thicker, and which sometimes possessed processes (FIG. 9A–D). Contact was observed between the blood-derived macrophages and the resident macrophages (FIG. 9F–G), and between both macrophage types and the oligodendrocytes (FIG. 9H–I). The nature of this contact seems to be cell-engulfing; oligodendrocytes seem to be engulfed by both macrophage types. These resident macrophages were also nonspecific esterase positive (FIG. 8D–G).

In view of the inverse relationship between the numbers of oligodendrocytes and macrophages, and the effect the CM has on rat oligodendrocytes, we examined whether the soluble substances derived from regenerating fish optic nerves (i.e. –CM) are responsible for the postinjury oligodendrocyte regulation. When the CM was added to cultures of dissociated optic nerves, which had been organ cultured for 2–3 days, the number of oligqdendrocytes decreased. Because of the low number of oligodendrocytes per coverslip, the experiment was repeated several times. The statistical test showed that the effect of the CM on the oligodendrocyte number is significant. These results are shown in Table IV.

TABLE IV

The effect of medium, conditioned by regenerating fish optic nerves (CM), on the number of oligodendrocytes in fish optic nerve cultures[a].

| | Number of oligodendrocytes[c] (±S.D.)[d] | |
| --- | --- | --- |
| Experiment no.[b] | Control | CM - treated[e] |
| 1 | 24.5 ± 2.0 | 13 ± 1.5 |
| 2 | 57 ± 16 | 30 ± 3.5 |
| 3 | 36 ± 8.0 | 26 ± 12 |
| 4 | 24 ± 4.0 | 19 ± 4.0 |
| 5 | 19 ± 3.0 | 3.5 ± 2.5 |
| 6 | 13.5 ± 0.6 | 4.5 ± 0.6 |
| 7 | 15 ± 3.5 | 7 ± 5.0 |

[a]Optic nerves were excised and organ cultured for two days. The optic nerves were then dissociated and plated. At this stage the conditioned media of the regenerating fish optic nerves (CM) was added to the appropriate wells.
[b]Because of the small cell number, the experiment was repeated several times.
[c]Each experiment was done in triplicate, the mean of which is given.
[d]Standard deviation of the triplicates.
[e]The CM was added to give a final concentration of 40 $\mu$g/ml. The Friedmann Rank Test used to statistically analyze the results gave a value of p = 0.0001 for the significant difference between the control and CM-treated coverslips.

The Friedman block rank test, which was used to analyze the results, showed that the significant difference between the control (untreated) and CM treated coverslips was equal to 0.01% (p=0.0001). When medium conditioned by non-regenerating (normal) goldfish optic nerves (CMN) was similarly added to the cultures, no effect was seen on the number of oligodendrocytes, as shown in Table V.

TABLE V

The effect of medium conditioned by normal fish optic nerves (CMN) on the number of fish oligodendrocytes, compared to medium conditioned by regenerating fish optic nerves (CM)[a].
Number of oligodendrocytes (±S.D.)[b]

| Control | CM - treated[e] | CMN - treated[e] |
| --- | --- | --- |
| 92 ± 22[c] | 50 ± 6[c] | 103 ± 15[c] |
| 46[d] | ND | 45[d] |

[a]The experiment was carried out as described in table I.
[b]Standard deviation of triplicates.
[c]Each experiment was done in triplicate, the mean of which is given.
[d]Experiment was carried out in duplicates. Therefore, no SD is given.
[e]The CM and CMN were added to give a final concentration of 40 $\mu$g/ml.

Example 7

This experiment shows the sensitivity of the OCF of the invention to treatment at 56° C.

Determination of Galc positive cells in cultures of newborn rat brain cells enriched for oligodendrocytes is carried out by ELISA as described in Experimental Procedures. As can be seen from Table VI, at 56° C. there is a reduction in the number of Galc positive cells as evidenced by the reduction in the measured optical density.

TABLE VI

Temperature sensitivity of the OCF comprised in the conditioned medium (CM) as measured by ELISA

| | Average optical density ± SD | |
| --- | --- | --- |
| Concentration a | Room Temperature | 56° C. b |
| — | 0.752 ± 0.076 c | — |
| CM(200 $\mu$g/ml) | 0.556 ± 0.008 | 0.738 ± 0.040 |
| CM(20 $\mu$g/ml) | 0.646 ± 0.029 | 0.709 ± 0.016 | a Final concentration of the CM
b The culture is heated at 56° C for 30 min.
c Experiment done in 4 trials, the mean of which is given.

Example 8

This experiment shows the effect of conditioned medium of fish blood macrophage on oligodendrocytes.

A macrophage-rich culture was prepared as follows. Blood was collected from fish into PBS containing heparin, and then layered over Hypaque-Ficoll gradient made by mixing 70.6 ml of 12% w/v Ficoll (Sigma) with 29.4 ml of 32.8 w/v sodium diatriozate (Sigma). Ten ml of blood were layered over 5 ml of Hypaque-Ficoll in a 15 ml polystyrene tube. The tubes were centrifuged at 1000 g for 25 min at 10° C. The buffy coat containing lymphocytes and monocytes were removed and washed once with PBS. Cells were collected and adjusted to 20×106 cells/ml. After 1 h at 16° C., the cells were washed 3 times with PBS to remove loosely adherent and non-adherent cells. Then L-15 medium was added to the cells.

Medium conditioned by macrophage-rich culture was prepared by incubating the cells in a serum-free medium for 8 h or in medium containing lipopolysaccharide. This conditioned medium was added to oligodendrocyte cultures and the number of oligodendrocytes was determined by counting immunofluorescent Galc positive cells, as described in Experimental Procedures. In the first experiment, the number of Galc-positive cells counted in the presence of the conditioned medium of the macrophage-rich culture was 420 in comparison to 839 in the control. In the second experiment, there were 24 Galc-positive cells in comparison to 62 in the control.

Example 9

This example shows that cytotoxicity of medium conditioned by regenerating fish optic nerves on oligodendrocytes can be neutralized by anti-IL-2 antibodies.

Medium conditioned by regenerating fish optic nerves was treated with antibodies against IL-2 to examine whether this would result in a loss of cytotoxic activity. It was found that antibodies directed against IL-2 neutralized the cytotoxic effect of the conditioned medium.

Figure 10:
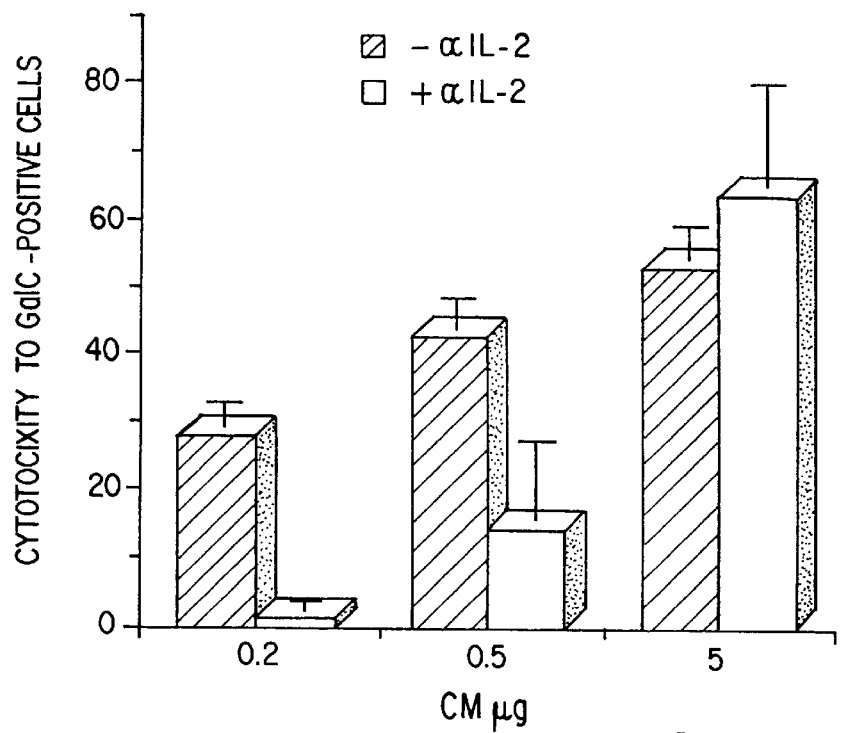
FIG. 10 shows neutralization of the cytotoxic effect of fish soluble substances on oligodendrocytes by rabbit polyclonal antibodies directed against recombinant human IL-2 antibodies: assessment by immunofluorescence. The highest concentration of the soluble substances derived from regenerating fish optic nerves (5 $\mu$g protein) resulted in about 60% cytotoxicity and no neutralization with anti-IL-2 antibodies; 0.5 $\mu$g of conditioned medium caused 42% cytotoxicity, half of which could be neutralized by the antibodies; complete neutralization with the same amount of antibodies could be obtained when only 0.2 $\mu$g of the conditioned medium were applied. Results are expressed as percent cytotoxicity, in relation to cytotoxicity-free control cultures treated with the antibodies only (100% survival, no cytotoxicity). All experiments were repeated 3 times and were carried out using 0.1 $\mu$g of anti-IL-2 antibodies (IgG). The results of one experiment are given in this figure; CM designates conditioned medium. The absolute total number of GalC positive cells counted in each coverslip ranged from 300 to 500 in the various experiments.
Figure 10A:
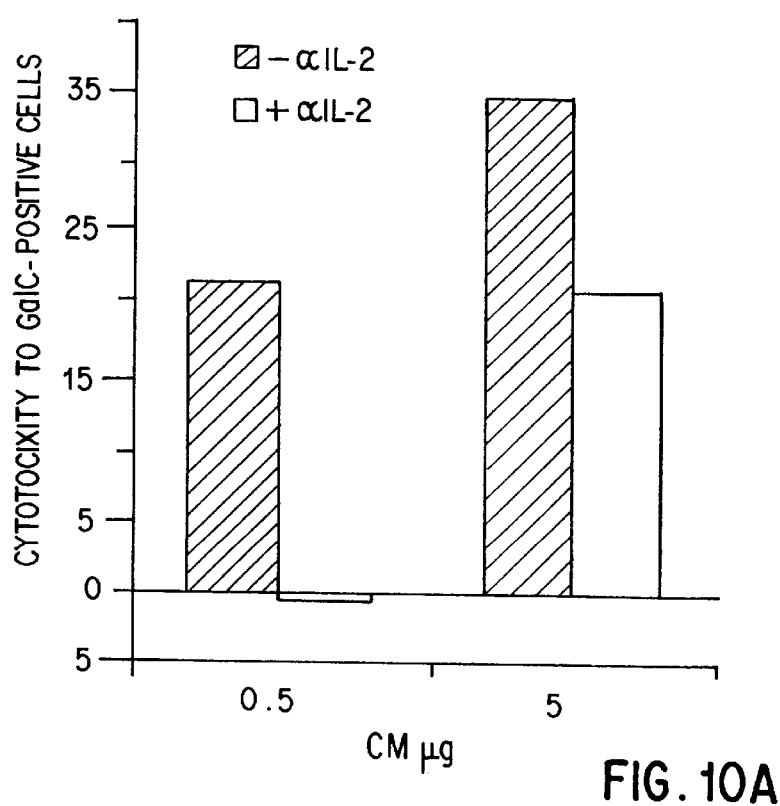
FIG. 10A shows the experiments carried out in FIG. 10 with 10-fold more anti-IL-2 antibodies, i.e., 1 $\mu$g IgG.

The neutralization of the cytotoxic effect of fish soluble substances on oligodendrocytes by rabbit polyclonal antibodies directed against recombinant human IL-2 antibodies was assessed. The results are shown in FIG. 10. After 48 h conditioned medium, either alone or preincubated with rabbit polyclonal antibodies against recombinant human IL-2, was added to the oligodendrocyte cultures and incubated for a further 48 h. Antibodies directed against neurofilaments were used as control. Oligodendrocytes were identified by immunofluorescence.

As can be seen in FIG. 10, antibodies against recombinant mouse IL-2 neutralized the cytotoxic activity of the conditioned medium. When the amount of antibodies was kept constant (0.1 μg IgG fraction; 1 μg neutralizes 1 U of IL-2) the neutralization achieved was a function of the concentration of conditioned medium applied, with complete neutralization at the lowest concentration tested, i.e., 0.2 μg/ml total protein. A 10-fold higher amount of antibodies (1 μg IgG fraction) resulted in neutralization of higher concentrations of conditioned medium (i.e., 0.5 and 5 μg/ml) (FIG. 10, inset). According to these results, and based on the potency of the IL-2 antibodies used for neutralization in the present assay, 1 μg of the conditioned medium is estimated to contain 0.5–2 U of biologically active IL-2-like molecules, i.e., OCF.

Example 10

This example shows the characterization of OCF from fish conditioned medium.

In order to determine the size of the IL-2-like molecule, the fish optic nerve conditioned medium containing soluble substances was subjected to Western blot analysis using mouse monoclonal antibodies directed against human IL-2.

Figure 11:
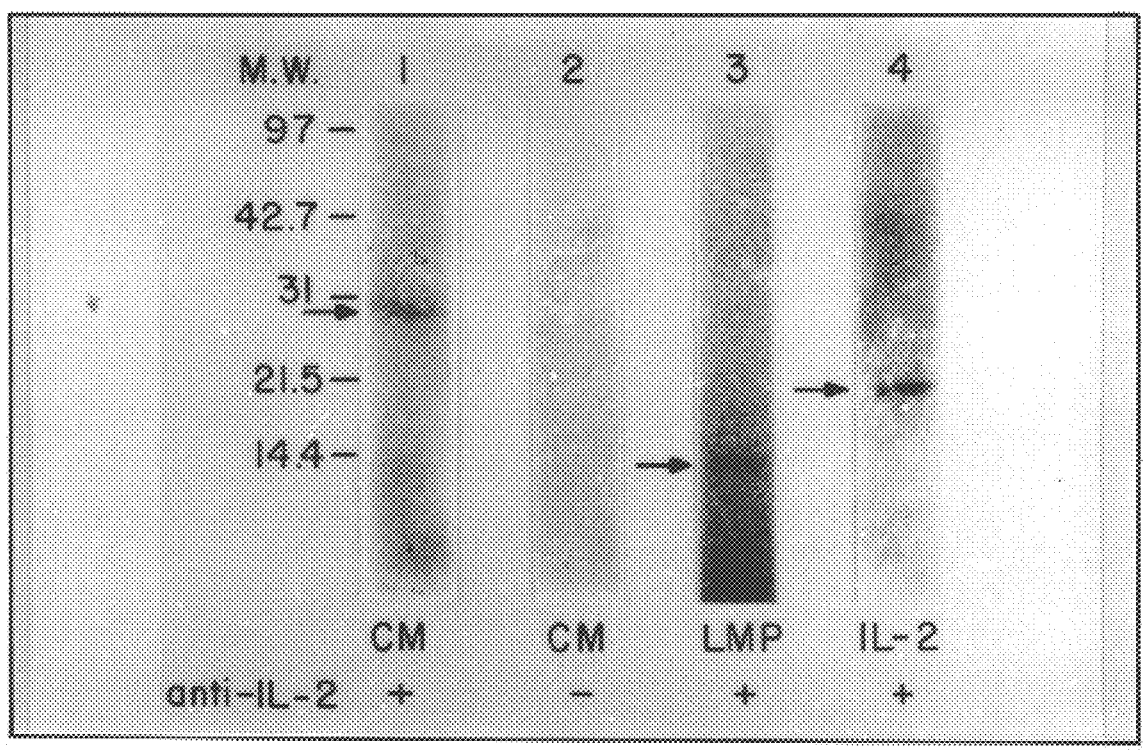
FIG. 11 shows Western blot analysis of the fish optic nerve soluble substances using mouse anti-human IL-2 monoclonal antibodies. Optic nerve conditioned media (CM, 400 $\mu$g), media conditioned by fish blood lymphocytes (LMP, 16 $\mu$g), and mouse IL-2 (75 ng) were electrophoresed on SDS-PAGE. Lane 1 contains conditioned medium (CM) incubated with anti-IL-2 antibodies. Lane 2 is the control slot containing conditioned medium (CM) reacted with second antibodies only. Lane 3 is a slot containing medium conditioned by fish lymphocytes (LMP) incubated with the anti-IL-2 antibodies. Lane 4 is a slot containing recombinant mouse IL-2 incubated with the same antibodies. The arrows at the left of each lane (excluding lane 2) point to the IL-2 immunoreactive bands in each slot. Molecular weight markers were electrophoresed on the same gel and are marked on the gel.

FIG. 11 shows the presence of a single IL-2 immunoreactive band at a molecular weight of 28 kDa. Since lymphocytes are known to produce IL-2, the interaction of the same antibodies was compared with fish lymphocytes, under the same experimental conditions. As shown in FIG. 11, a single IL-2 immunoreactive band of approximately 14 kDa was observed. These results indicate that the molecule responsible for the cytotoxic effect on oligodendrocytes cross reacts with anti-IL-2 antibodies.

Example 11

This example shows affinity purification of OCF from fish conditioned medium.

Purification of the cytotoxic substances was carried out by the use of an IL-2 affinity column as follows.

Mouse monoclonal antibodies against recombinant human IL-2 antibodies were coupled to polyacrylhydrazide agarose (BioMakor, Israel). Using the procedure of Wilchek and Miron (Meth.Enzymol. (1974) 34, 72–76), 0.1 ml of packed resin was coupled to 0.5 mg of antibodies. Purification was carried out as follows: Conditioned medium (50 μl) was added to the antibody-coupled packed resin, to which anti-IL-2 antibodies were coupled and incubated for 2 h at 37° C. The supernatant was then collected and the remaining resin washed 3 times, each time with 1 ml of PBS. Elution was carried out with 50 μl of glycine (0.2 M, pH 2.7) with shaking for 10 min, at room temperature. The eluted material (ELU) was collected into 10 μl Tris buffer (1 M, pH 8.0). The fractions containing the IL-2-bound substances were tested for their cytotoxic effects on oligodendrocytes by the use of the colorimetric MTT (3-(4,5 dimethylthiazol-2-yl)-2,5-diphenyl tetrazolium bromide) assay (Sigma) for assessment of the number of oligodendrocytes and hence of the cytotoxicity (Mosmann, T. (1983) J.Immunol.Meth. 65, 55–63).

The assay was carried out as follows: Cells were treated with the conditioned medium alone or with the bound substances eluted from the column of anti-IL-2 antibodies (ELU). The final dilutions of the eluted substances (ELU) used in the assay corresponded to those of the crude conditioned medium. Following incubation for 48 h, 10 μl of MTT was added for 3 h; the medium was then removed and 100 μl of 0.04 N HCl in isopropanol was added. The cells were gently shaken until all crystals had dissolved, and their absorbance was recorded at 550 nm against 600 nm as a reference wavelength.

Figure 12:
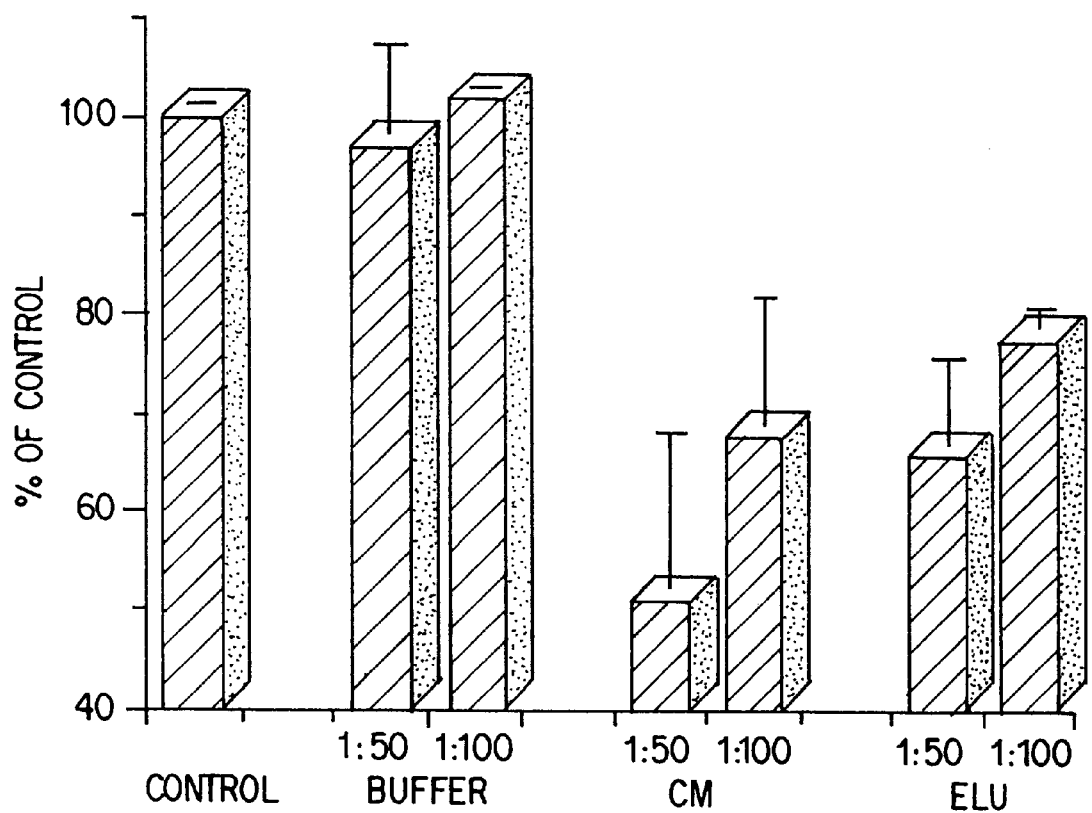
FIG. 12 shows affinity purification of the IL-2-like factor from fish optic nerve conditioned medium. Cytotoxic activity on oligodendrocytes, assessed by the colorimetric MTT assay, was recovered from the fish optic nerves by elution of the substances bound to the anti-IL-2 antibodies, which had been coupled to the column. Controls were untreated cultures or cultures treated with medium containing the elution buffer (Buffer), thus ruling out the possibility that any cytotoxicity in the eluate might have resulted from the buffer used for elution of the bound material from the column. The experiment, which was repeated 3 times, was performed in triplicate and the results are presented as means±SD of the untreated culture values, representing 100% survival. Analyses by the repeated measures method revealed that the effects of the eluted substances (ELU) differed significantly (P<0.05) from those of the two corresponding control cultures.

As shown in FIG. 12, the IL-2-bound substances eluted from the column were cytotoxic to oligodendrocytes. The small scale of the purification did not permit calculation of the specific activity of the eluate. However, in view of the known limits of the protein detection we could estimate that the specific activity of the eluate was at least 103-fold higher than that of the conditioned medium. The eluate, which was found to retain the cytotoxic activity, was also subjected to Western blot analysis using anti-IL-2 antibodies which revealed the presence of the original 28-kDa immunoreactive polypeptide (data not shown). These results thus identify the IL-2 immunoreactive 28-kDa protein as the OCF.

Example 12

Conditioned Medium of Insured Fish Optic Nerve can modify IL-2 with respect to its molecular weight Since oligodendrocyte cytotoxic factor is present in media conditioned by injured fish optic nerve, and oligodendrocyte cytotoxic factor was found to be an IL-2-like molecule of molecular weight of about 28 Kd, whose cytotoxic activity is neutralized by anti-IL-2 antibodies, it was then examined whether the fish injured nerve carries a substances probably an enzyme, that can modify mammalian IL-2 of low molecular weight to a high molecular weight form of IL-2. Media conditioned by regenerating fish optic nerves were examined for the presence of a mechanism for the posttranslational modification of exogenously added IL-2. Accordingly, human recombinant IL-2 (hIL-2) was incubated with the conditioned media (CM) in the presence of 5 mM $Ca^{2+}$ or in its absence, and the resulting products were subjected to Western blot analysis with the aid of antibodies directed against IL-2.

For this purpose, CM of regenerating fish optic nerves was prepared as previously described by Eitan et al., 1992. Briefly, carp were anesthetized with 0.05% 3-aminobenzoic acid ethyl ester (Sigma) and the right optic nerves were crushed with forceps (for 30 sec), excised 6–7 days later and incubated in serum-free medium (1.5 hours at 25° C., 4 nerve segments in 300 μl medium). The resulting media (CM) were collected and their protein content determined by the Bradford method.

Aliquots of 6 μg CM were incubated overnight with hIL-2, while being gently shaken with 5 mM $CaCl_2$. The mixture was subjected to SDS-PAGE (12% acrylamide). The gel was blotted onto nitrocellulose for 2 hours at 200 mA, and the nitrocellulose incubated overnight at 4° C. with phosphate-buffered saline (PBS) containing 5% (wt/vol) milk, and then washed in PBS. The blot was incubated with IL-2 antibodies for 2 hours at 37° C., then washed three times for 5 min in PBS containing 0.05% Tween-20, and finally with horseradish peroxidase (HRP)-conjugated goat anti-rabbit IgG for 2 hours at room temperature. Visualization of the immunoreactive bands was accomplished by ECL (Amersham).

Figure 13:
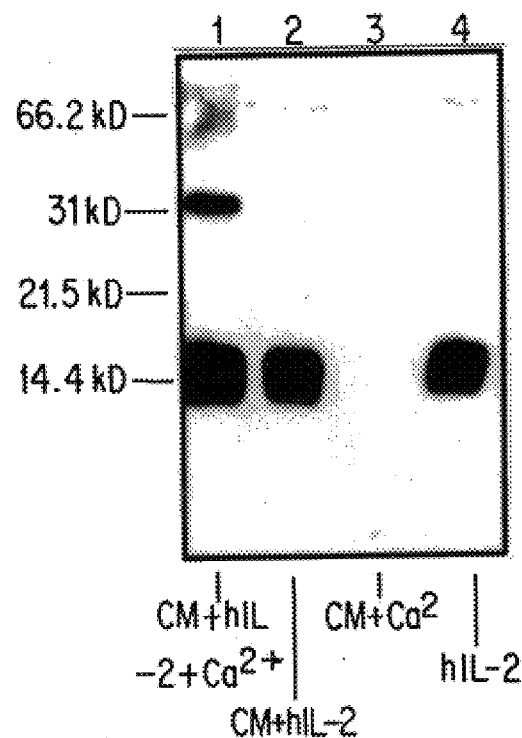
FIG. 13 shows the ability of conditioned medium (CM) of regenerating fish optic nerves to dimerize human IL-2 (hIL-2). Aliquots of CM were incubated overnight with hIL-2, and the mixture was subjected to SDS-PAGE (12% acrylamide), followed by Western blot using IL-2 antibodies. Visualization of the immunoreactive bands was accomplished by ECL (Amersham). Lanes: 1, CM incubated with hIL-2 in the presence of $Ca^{2+}$; 2, CM incubated with hIL-2 in the absence of $Ca^{2+}$; 3, CM only in the presence of $Ca^{2+}$; 4, hIL-2 only. Molecular weight markers were electrophoresed on the same gel and their positions are indicated.

The results are shown in FIG. 13, wherein: Lane 1, CM incubated with hIL-2 in the presence of $Ca^{2+}$; Lane 2, CM incubated with hIL-2 in the absence of $Ca^{2+}$; Lane 3, CM only in the presence of $Ca^{2+}$; Lane 4, hIL-2 only in the absence of $Ca^{2+}$. Molecular weight markers were electrophoresed on the same gel and their positions are indicated. In the slot containing only hIL-2, one immunoreactive band of 15 kDa was found. Following incubation with CM, an additional IL-2 immunoreactive band having a molecular weight twice as high as that of the original IL-2 compound could be detected. These results raised the possibility that the regenerating nerve possesses the machinery to dimerize IL-2. The high molecular weight IL-2 immunoreactive band was not observed when $Ca^{2+}$ was omitted from the incubation mixture (FIG. 13, lane 2), suggesting that the dimerization process is mediated by a $Ca^{2+}$-dependent enzyme.

Example 13
Transglutaminase Immunoreactivity in Fish Optic Nerves is Elevated after Injury In view of these findings, we considered the possibility that the agent responsible for modifying the IL-2 is an enzyme that is selectively elevated after injury, and that the effect of the enzyme is to achieve dimerization of the IL-2 molecule. The enzyme transglutaminase was considered as a potential candidate, as it is known to be involved in cross-linking of proteins (Greenberg et al., 1991); moreover, in the regenerating fish optic nerve it was proposed that an activity reminiscent of transglutaminase is elevated (Chakrabarty et al., 1987).

Antitransglutaminase antibodies were elicited in rabbits against each of a synthetic peptide of 10 and 14 amino acids bound to bovine serum albumin. The peptides, of the sequence Asn-Ser-Lys-Leu-Thr-Lys-Lys-Lys-Lys-Lys, or Lys-Lys-Val-Lys-Tyr-Gly-Gln-Cys-Trp-Val-Phe-Ala-Gly-Val, correspond to known sequences of transglutaminases of other species and tissues. The 14-mer peptide represents the active site of transglutaminases.

Western blot analysis confirmed the presence of a 55-kDa transglutaminase-immunoreactive band in the regenerating fish optic nerve. The gel was blotted as described in Example 1. CM (20 μg) and high speed supernatant of regenerating optic nerves (HSS-C; 16 μg) and high speed supernatant of normal non-injured nerves (HSS-N; 20 μg) were electrophoresed on SDS-PAGE (10% acrylamide). The blot was incubated with antibodies prepared against the above-mentioned conserved 14-mer peptide for 2 hours at room temperature, and then washed three times for 5 min in PBS containing 0.05% Tween-20. Finally, the blot was incubated for 2 hours at 37° C. with HRP-conjugated goat anti-rabbit antibodies. Visualization was accomplished by ECL (Amersham).

Figure 14:
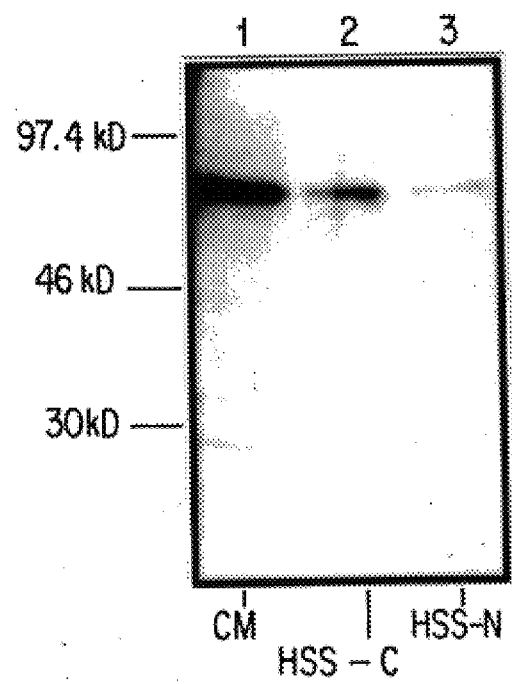
FIG. 14 shows Western blot analysis revealing the presence of a transglutaminase immunoreactive protein of 55 kDa in regenerating fish optic nerves. CM, high speed supernatant of regenerating optic nerves (HSS-C) and high speed supernatant of normal non-injured nerves (HSS-N) were electrophoresed on SDS-PAGE (10% acrylamide). The blot was incubated with antibodies prepared against the conserved 14-amino acid sequence of the transglutaminase enzyme family. Visualization was accomplished by ECL (Amersham). Lanes: 1, CM; 2, HSS-C; 3, HSS-N.

The results are shown in FIG. 14 wherein : Lanes: 1, CM; 2, HSS-C; 3, HSS-N. The 55-kDa immunoreactive band was observed in CM and in HSS. Densitometric analysis revealed that the intensity of the 55-kDa immunoreactive band is 3-fold higher in HSS-C than in HSS-N.

Example 14
Purification of Fish Optic Nerve Transglutaminase

In order to verify that this transglutaminase-immunoreactive protein is responsible for the observed modification of IL-2, it was purified as follows: Carp (Cyprinus carpio) optic nerves (n=60) were excised 6–7 days after crush injury and homogenized in a buffer of 10 mM Tris-HCl, pH 7.4, containing 1.5 mM $CaCl_2$, 1 mM spermidine, 25 μg/ml aprotinin, 25 μg/ml leupeptide and 5 μg/ml pepstatin. Sucrose was added to the homogenate to obtain a final concentration of 0.25 M. The high speed supernatant (HSS) was collected after centrifugation for 1h at 4° C. at 150,000 g, and its protein content was determined by the Bradford method. The HSS was then eluted through an affinity column of poly-L-lysine (PLL) coupled to agarose, and the resultant eluate (Eluate PLL) was subjected to an additional affinity column of the affinity-purified rabbit antibodies prepared as described above against the conserved 14-mer peptide of transglutaminase. Bound substances were eluted from the column with 0.2M glycine, pH 2.7, neutralized with 1M Tris, pH 8.0, and their protein content determined (Eluate TG Ab). The purification steps are summarized in Table VII.

TABLE VII

| Purification of fish optic nerve transglutaminase | | |
|---|---|---|
| Purification Steps | Yield/mg | Purification degree |
| Crude homogenate | 14 | 1 |
| Eluate PLL | 1.8 | 7.8 |
| Eluate TG Ab | 0.004 | 3500 |

Figure 15:
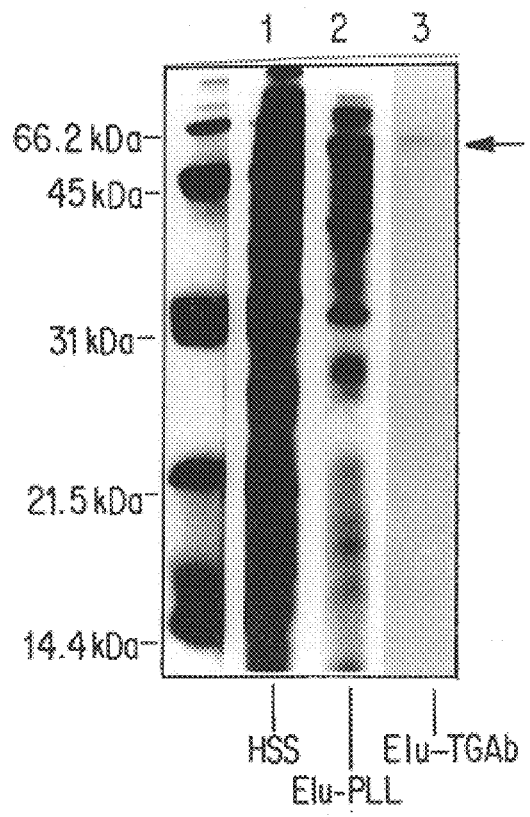
FIG. 15 depicts SDS-PAGE showing the stepwise purification of fish optic nerve transglutaminase ($TG_N$). Lanes: 1, HSS; 2, Elu-PLL (eluate from PLL-agarose column); 3, Elu-TG Ab (eluate from anti-transglutaminase affinity column)

The proteins eluted from the transglutaminase affinity column were subjected to 10% SDS-PAGE to verify their purity. FIG. 15 is SDS-PAGE showing the stepwise purification of fish optic nerve transglutaminase ($TG_N$). Following each step, the resulting preparation was subjected to SDS-PAGE, and the gel was stained for visualization of the analyzed proteins by silver staining. Lanes: 1, HSS; 2, Elu-PLL; 3, Elu-TG Ab. As shown, a single band of 55 kDa is obtained after the last step of purification.

The enzyme $TG_N$ can be purified also from the conditioned medium of regenerating fish optic nerve by applying it to an affinity column of PLL coupled to agarose, followed by subjecting the eluate to an additional affinity column of the antibodies and elution, as described above for the homogenate.

Example 15
Incorporation of Putrescine to Casein Mediated by $TG_N$

The incorporation of radioactive putrescine to a carrier protein is an assay characteristic of enzymes of the transglutaminase family. Any carrier protein that has lysine residues may be used in the assay, such as casein, bovine serum albumin, etc.

In this example, activity characteristic of the nerve-derived transglutaminase was measured by incorporation of [$^{14}$C]putrescine into N,N-dimethylcasein (Chakrabarty et al., 1987). The purified $TG_N$ enzyme eluted from the TG-Ab affinity column with glycine in Example 14 was dialyzed for 2 hours in the presence of N,N-dimethylcasein (1 mg/ml), before being added to the reaction mixture. The reaction was initiated by addition of crude $TG_N$ (07–10 ng), followed by incubation for 20 min at 37° C. and terminated by the addition of ice-cold trichloroacetic acid (TCA; final concentration, 5%). Specific activity value of $TG_N$ is 502000±115000 ([$^{14}$C]putrescine/μg protein; cpm) (n=3, two purifications, three assays).

Figure 17A:
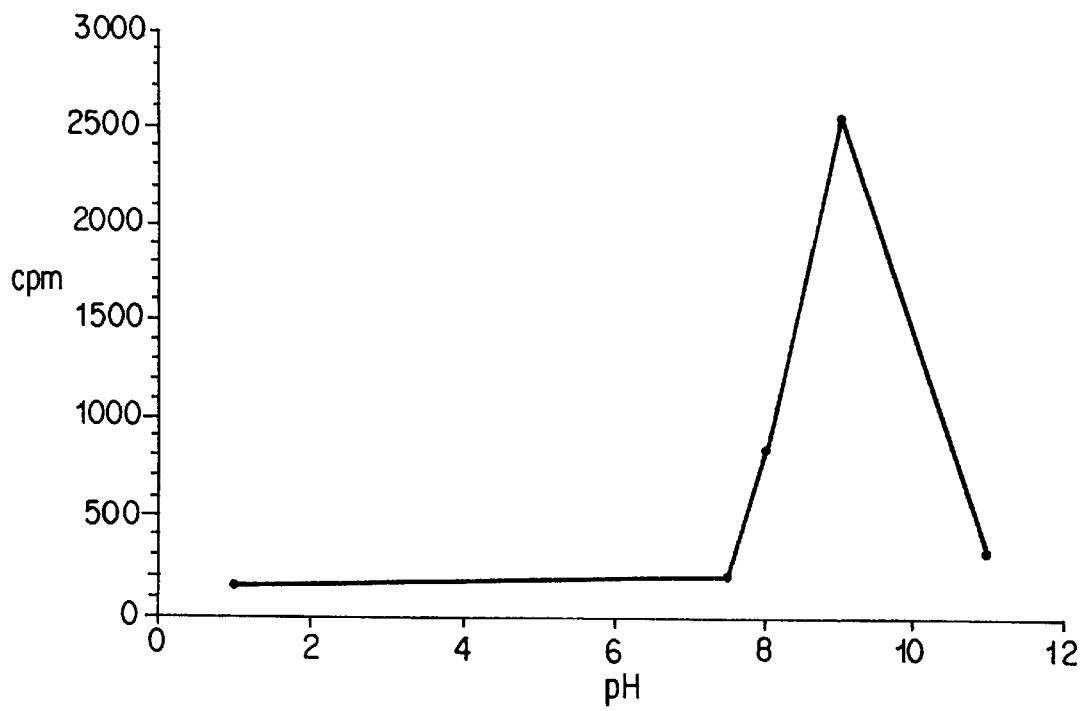
FIG. 17A illustrates biochemical characterization of the enzyme $TG_N$. The Figure shows putrescine incorporation to casein mediated by $TG_N$ as a function of pH.
Figure 17B:
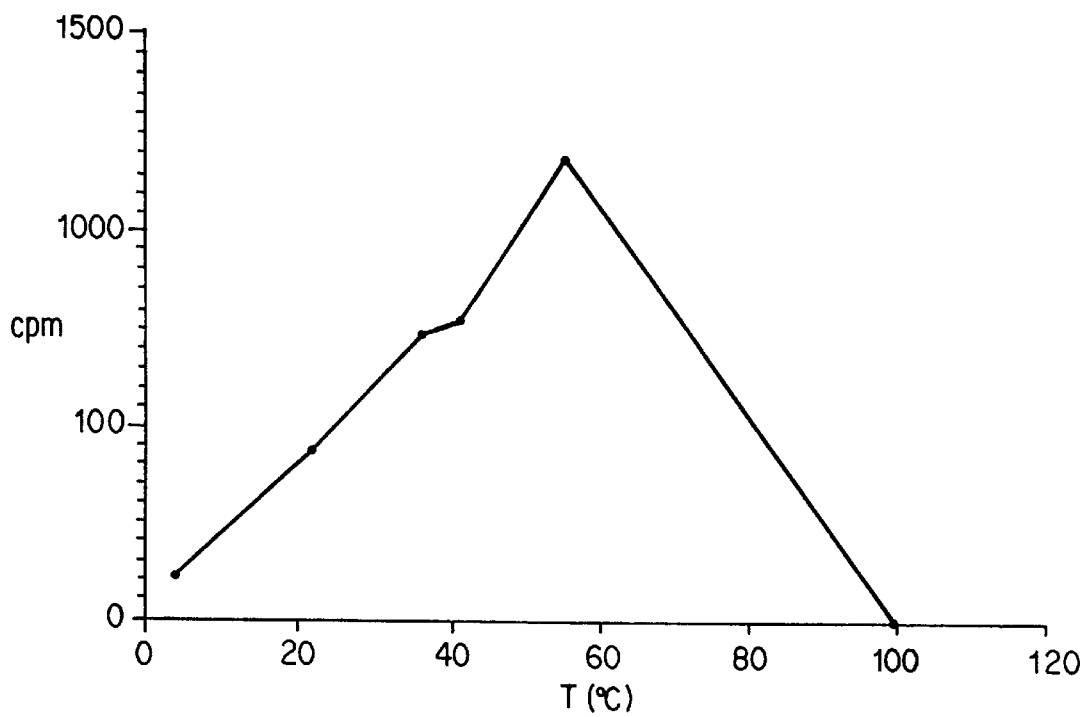
FIG. 17B illustrates biochemical characterization of the enzyme $TG_N$. The Figure shows putrescine incorporation to casein mediated by $TG_N$ as a function of temperature.
Figure 17C:
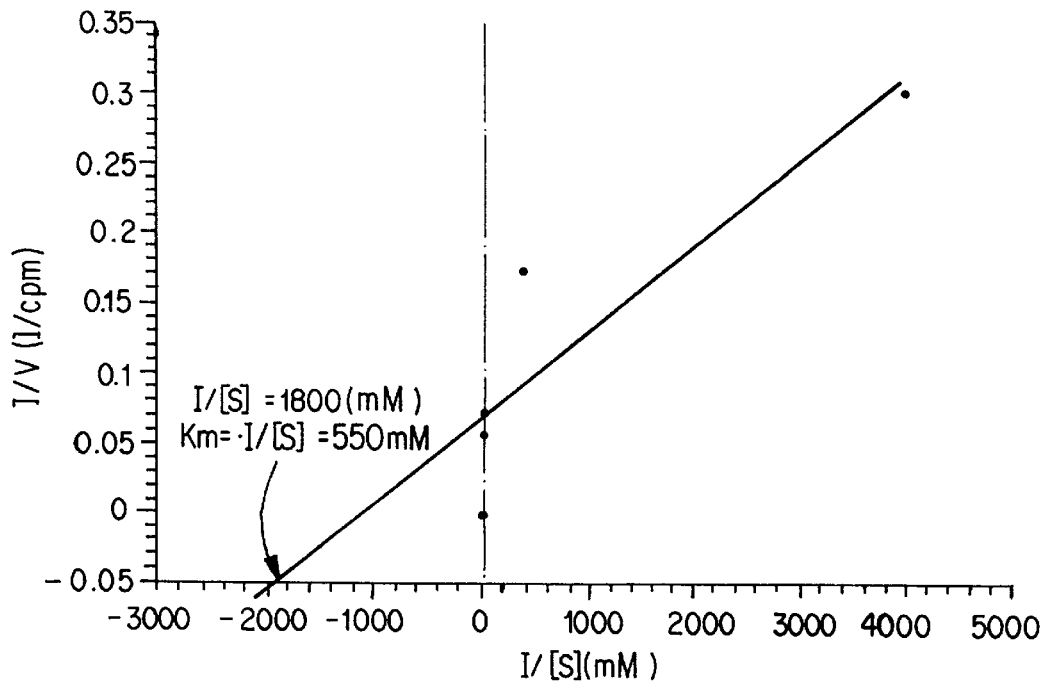
FIG. 17C illustrates biochemical characterization of the enzyme $TG_N$. The Figure illustrates determination of $K_m$ of $TG_N$ by Scatchard plot analysis.

The enzyme activity was titrated with respect to temperature and pH and substrate concentration. As shown in FIG. 17A and 17B, respectively, the optimal activity of $TG_N$ was found at pH around 9 and at 56° C. The $K_m$ was calculated from the titration of activity as a function of substrate concentration and was found to be $5.5 \times 10^{-7}$M. Titration was carried out by measuring incorporation of [$^{14}$C]putrescine to caseine in the presence of $TG_N$.

Example 16
Purified Fish Optic Nerve Transglutaminase Dimerizes Human IL-2

The ability of the purified enzyme of Example 14 to dimerize IL-2 was examined. Human recombinant IL-2

(hIL-2) was incubated as described in Example 1, except that in this experiment purified $TG_N$ was used rather than the crude CM. As controls, hIL-2 or the purified enzyme $TG_N$ were incubated separately in the same buffer. All incubations were carried out in the presence of 5 mM $Ca^{2+}$ and 0.3% heat-inactivated fetal calf serum (FCS).

Figure 16:
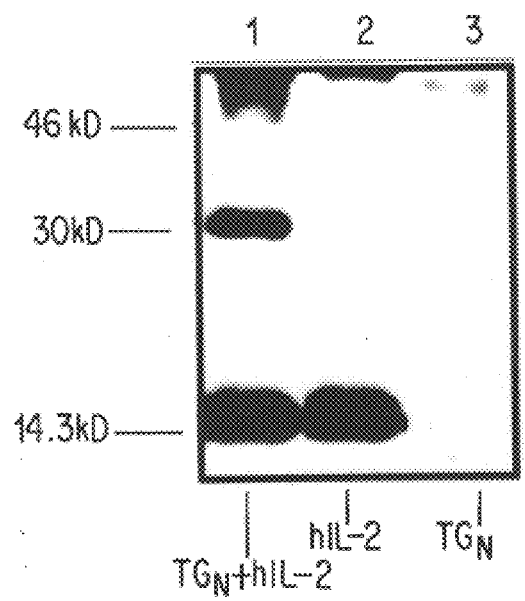
FIG. 16 shows that purified $TG_N$ dimerizes hIL-2. Lanes: 1, purified $TG_N$ incubated with hIL-2; 2, hIL-2 only; 3, $TG_N$ only. The experiment was carried out as described in FIG. 1, except that purified $TG_N$ was substituted for the CM. All incubations were carried out in the presence of 5 mM $Ca^{2+}$.

Following the incubation the mixture was applied to analysis by Western blot. Separation was carried out on SDS-PAGE (12% acrylamide) followed by blotting onto nitrocellulose for 2h at 200 mA. The nitrocellulose was then washed in PBS, first incubated overnight at 4° C. in PBS containing 5% milk, and then further incubated for 2h at 37° C. with rabbit antibodies directed against human IL-2, followed by 3 washes in PBS containing 0.05% Tween-20. After the last wash, further incubation for 1 ½h was carried out at room temperature with goat anti-rabbit antibodies conjugated to horseradish peroxidase (HRP-GaRb), followed by three washes with PBS containing Tween-20 and incubation for 1 min in the Western blotting detection reagent (ECL, Amersham), air drying and exposure to film. The results are shown in FIG. 16, wherein: Lanes: 1, purified $TG_N$ plus hIL-2; 2, hIL-2 only; 3, $TG_N$ only.

As shown in FIG. 16, in addition to the original IL-2, a high molecular weight IL-2 immunoreactive band of 30 kD was obtained. Densitometric analysis revealed that about 25% of the IL-2 was dimerized under these conditions.

Example 17

Enzymatically-produced Dimeric IL-2 is Cytotoxic to Olicodendrocytes

To ascertain the biological significance of the dimerization, we examined whether the resulting dimeric IL-2 possessed cytotoxic activity against oligodendrocytes. hIL-2 (at 100 U/ml or 10 U/ml) was incubated with the purified $TG_N$ enzyme and the reaction mixture was then applied to enriched cultures of rat brain oligodendrocytes. Control cultures consisted of untreated oligodendrocytes as well as oligodendrocytes exposed separately to hIL-2 at 100 U/ml of 10 U/ml and to the purified enzyme.

Enriched oligodendrocyte cultures derived from neonatal rat brains were prepared as described by Bottenstein and Sato, 1979, and seeded in wells coated with PLL (20 μg/μl) (Sigma). After 72 hours, the seeded cells were treated with various preparations containing either $TG_N$ alone, hIL-2 preincubated with $TG_N$, or hIL-2 alone. hIL-2 at two different concentrations, 10 U/ml and 100 U/ml, were incubated with a constant amount of $TG_N$. Cytotoxic activity (in terms of the number of surviving cells) was assessed by the colorimetric MTT assay (Sigma) (T. Mosmann, 1983, J. Immunol. Meth. 65:55–63). After incubation for 48 hours with the various preparations, MTT (10 μl, 5 mg/ml) was added for 3 hours; the medium was then removed, and 100 μl of 0.04M HCl in isopropanol was added. The cells were gently shaken until all crystals had dissolved. Their absorbance was recorded at 540 nm against absorbance at 630 nm as reference.

Figure 18A:
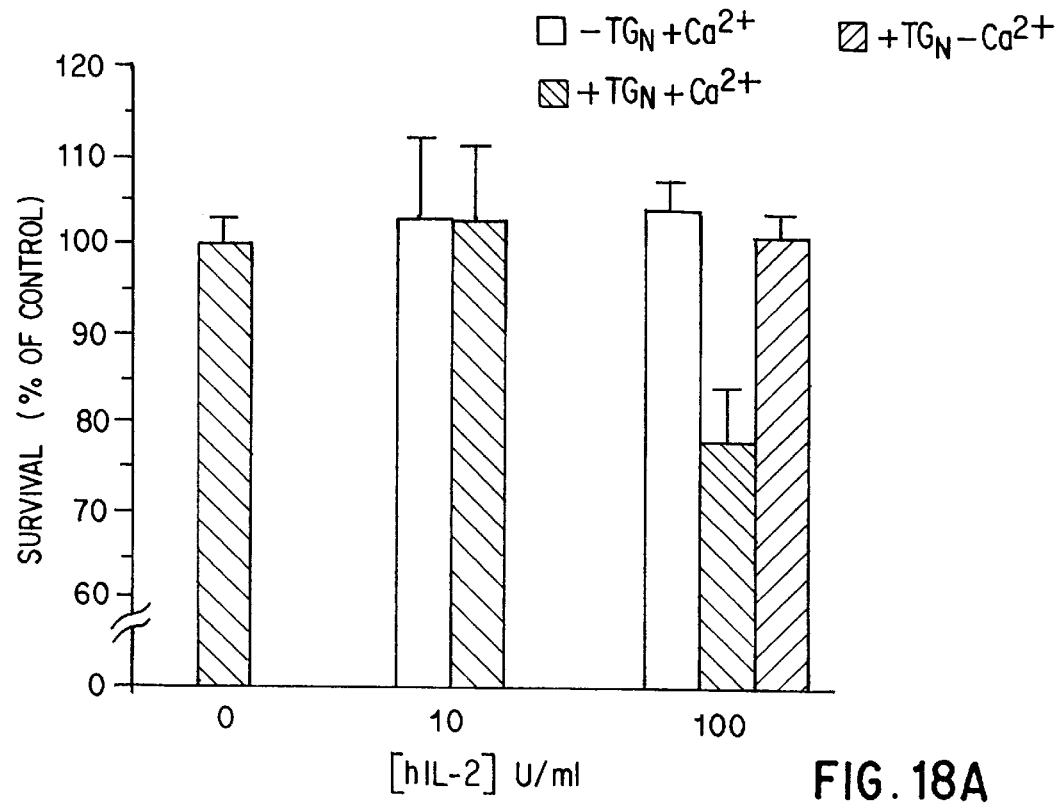
FIG. 18A shows that IL-2 activity shifts toward cytotoxicity against oligodendrocytes following dimerization mediated by $TG_N$. Enriched oligodendrocyte cultures were treated with various preparations containing either $TG_N$ alone, hIL-2 preincubated with $TG_N$, or hIL-2 alone. Cytotoxic activity (in terms of the number of surviving cells) was assessed by the colorimetric MTT[3-(4,5-dimethylthiazol-2-yl)-2,5-diphenyltetrazolium bromide] assay. The figure shows the quantitative analysis (absorbance at 540 nm against absorbance at 630 nm) of various cultures treated with 10 or 100 U/ml of hIL-2 in the presence or absence of $TG_N$, after MTT staining.
Figure 18:
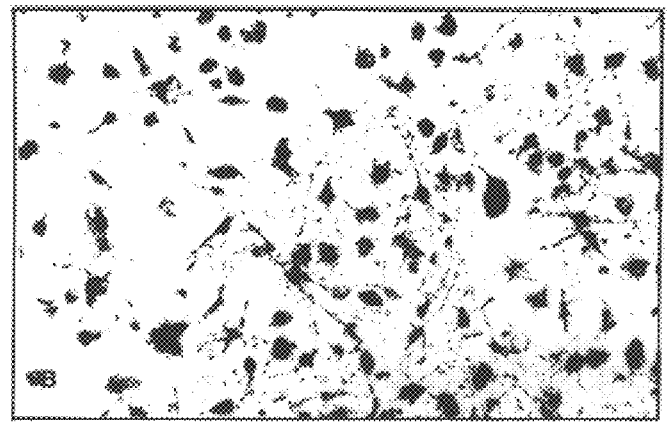
FIG. 18B shows a micrograph of cultures treated with hIL-2 only (100 U/ml) according to the protocol of FIG. 18A.
FIG. 18C shows a micrograph of cultures treated with $TG_N$ only according to the protocol of FIG. 18A.
FIG. 18D shows a micrograph of cultures treated with a mixture of hIL-2 (100 U/ml) and $TG_N$ (containing the enzymatically-produced dimeric hIL-2)
Figure 18:
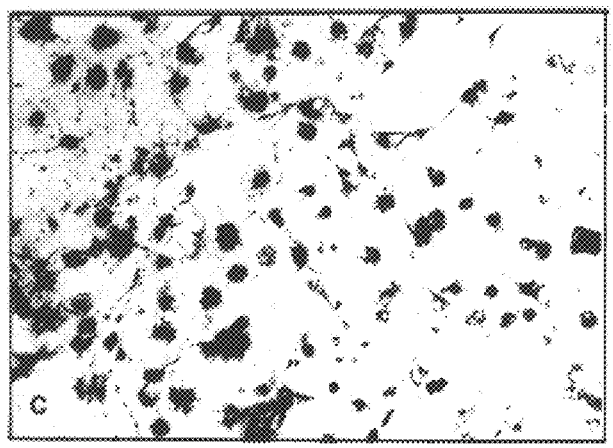
Figure 18:
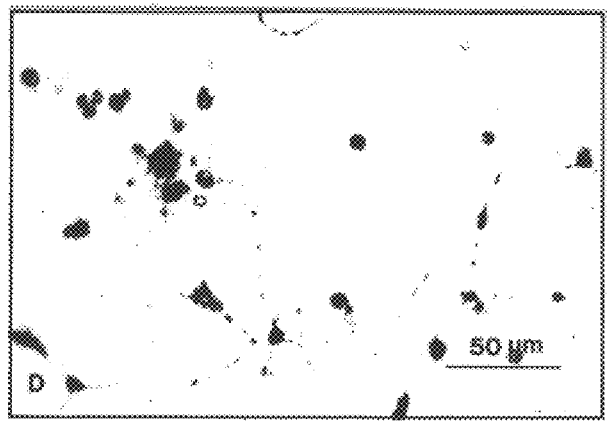

The results are shown in FIG. 18A–D. The micrographs show the various treated cultures after MTT staining. B, Cultures treated with hIL-2 only (100 U/ml); C, cultures treated with $TG_N$ only; D, cultures treated with the mixture of hIL-2 (100 U/ml) and $TG_N$ containing the enzymatically-produced dimeric hIL-2. As can be seen in FIG. 18, only those oligodendrocyte cultures that were treated with the reaction mixture containing the enzymatically-produced dimeric IL-2 exhibited cytotoxicity. From the results shown in FIG. 16 it appears that in the reaction mixture containing dimeric IL-2, 25% of the IL-2 is dimeric and the rest is in a monomeric form. It thus seems that 25 U/ml of IL-2 in the dimeric form is sufficient to exert cytotoxicity under conditions where 100 U/ml of monomeric IL-2 are not cytotoxic.

For the preparation of enriched oligodendrocyte cultures, neonatal rat brains (2 days old) were excised [2 brains in 2 ml of Leibowitz medium (L-15); Gibco] and chemically dissociated by $3\times10^4$ U/ml trypsin (Sigma) in DMEM ($Ca^{2+}$ and $Mg^{2+}$ free) containing 1 mM ethylenediaminetetraacetic acid (EDTA). Mechanical dissociation was carried out prior to 10 min incubation at 37° C. with the trypsin solution. The cells were then transferred into 15 ml conical tubes containing 1 ml of solution of 74 U/ml DNase (Sigma), 5200 U/ml soybean trypsin (Sigma) and 3 mg BSA, incubated for 1 min at room temperature, added to 10 ml of medium, and subsequently washed 3 times in DMEM. After the last wash, the cells were suspended in 10 ml DMEM containing 5–10% fetal bovine serum (FBS; Sigma-heat inactivated at 56° C. for 30 min), passed through mesh and seeded in 85 $mm^2$ flasks (Nunc), previously coated overnight at 37° C. with 20 μg/ml poly-L-lysine (PLL, MW 100000; Sigma). The medium was changed first twenty-four hours after cell seeding and then once every 2–3 days thereafter. On the 8th day after seeding, the cells were incubated with shaking for 4–6 h, the supernatant was removed and the remaining cells further incubated in 10 ml medium (DMEM plus 5–10% FBS) for several hours followed by an overnight shaking. The cells that were removed by the shaking were collected and centrifuged, and the pelleted cells were then resuspended in 1–2 ml of serum-free medium. The thus obtained enriched oligodendrocyte cultures recovered cells were seeded on 96-well plates previously coated with PLL (20 μg/ml). Cells were seeded with 100 μl of defined medium (Raff's modification to Bottenstein's and Sato's defined medium). After 48–72h, the seeded cells were treated as described above.

Example 18

$TG_N$ Treatment can cause Functional Recovery of Transected Adult Rat Optic Nerves Electrodes were implanted in the visual cortex of 30 adult (12–14 week old) Sprague-Dawley (SPD) rats for on-line monitoring of changes in the visual pathway, before and after injury. Anesthetized rats (Rumpon, Vetalar) were placed in a small animal stereotaxic instrument, and two holes were drilled in the exposed skull, with the dura kept intact to minimize cortical damage. One hole, drilled above the nasal bone, was used as reference point. The second hole was in area OC1, with coordinates Bregma −8mm and lateral 3 mm. The electrodes were gold contact pins (Wire-Pro, Inc.) connected to screws, which were screwed into the holes and cemented to the skull with acrylic cement. The field potential, recorded first in intact nerves and then after injury was evoked by stroboscopic stimulation (Xenon flash tube 4W/sec, 1–2 msec duration, 0.3 Hz), amplified 1000 times (AM Systems, Microelectrode AC amplifier, Model 1800) and digitized (12 bits, 500 samples/sec) (National Instruments, Board MIO16-9 and LabView 2.2.1 Data Acquisition and Management System). During recording of the visual evoked potential (VEP) response, the contralateral eye was always covered. One week after the electrodes were implanted, the left optic nerve was exposed by opening of the perineural sheath. The nerve fibers were dissected 2 mm from the globe, without damaging the nerve vascularization, with the aid of a specially designed glass probe with a 200-μm tip and a smooth blunt edge. The nerve was completely transected, and 2 μl of a buffer solution without or with $TG_N$ (designated control and $TG_N$-treated, respectively) was injected into the injury site via a glass pipet. For surgery, treatment and recording, a double-blind protocol was followed. The $TG_N$ employed was purified $TG_N$ prepared from CM according to Example 14.

One week after injury eight out of the 30 animals exhibiting residual VEP activity, probably reflecting incomplete transection, were withdrawn from the experiment and 10 $TG_N$-treated and 12 control animals were left for the rest of the experiment. Six weeks after injury, the VEP response was again recorded from the remaining 22 animals. The VEP response is characterized by two parameters: latency and amplitude of the first negative peak response. In this on-line experiment seven of the 10 $TG_N$-treated injured nerves, which remained for the follow-up as they had no response at 1 week, showed functional recovery (Table VIII). In the 12 control animals which were left after 1 week, no recovery was detected 5 weeks later (Table VIII).

Peaks of activity in most cases in $TG_N$-treated injured nerves seemed to be shifted, relative to those of uninjured nerves with significant difference between them in terms of both amplitude and latency (Table IX). The amplitude in $TG_N$- treated injured nerves, while always smaller than in intact nerves, was higher than expected, possibly because of arborization to vacant sites in the primary target (the lateral geniculate nucleus) or changes in the nature and amount of neurotransmitters involved in the evoked response.

Figure 19A:
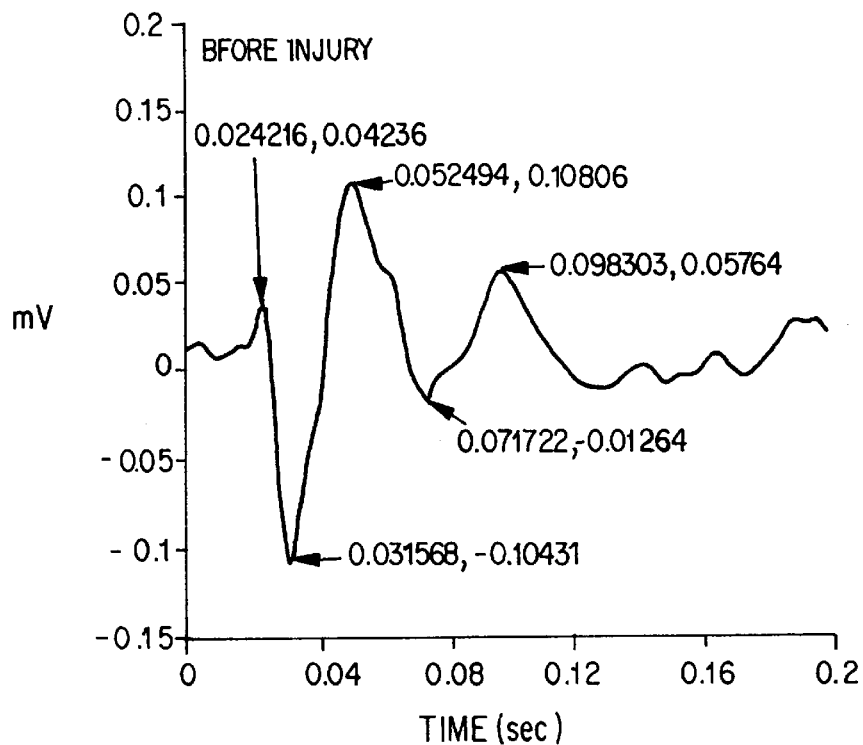
FIG. 19A depicts on-line recording of functional activity in a $TG_N$-treated injured nerve. The figure presents the results obtained from one representative animal (rat) treated with $TG_N$. Visual evoked potential (VEP) responses were recorded before the injury as described in the specification. Values are means obtained from four recordings at each time point (solid lines)±SE (grey line)
Figure 19B:
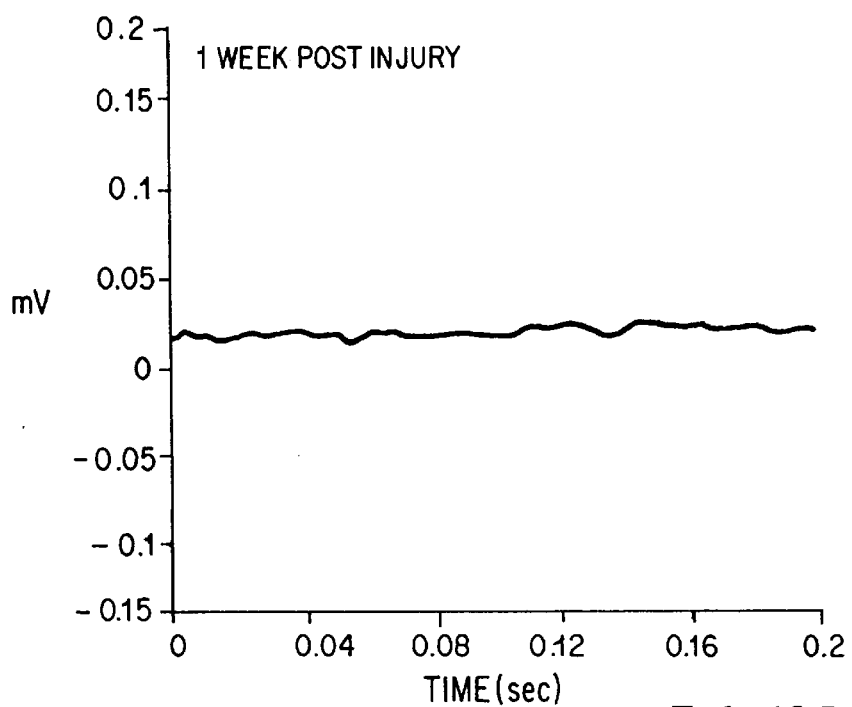
FIG. 19B displays the results obtained from the protocol in FIG. 19A with VEP potentials recorded 1 week after injury. Values are means obtained from four recordings at each time point (solid lines)±SE (grey line)
Figure 19C:
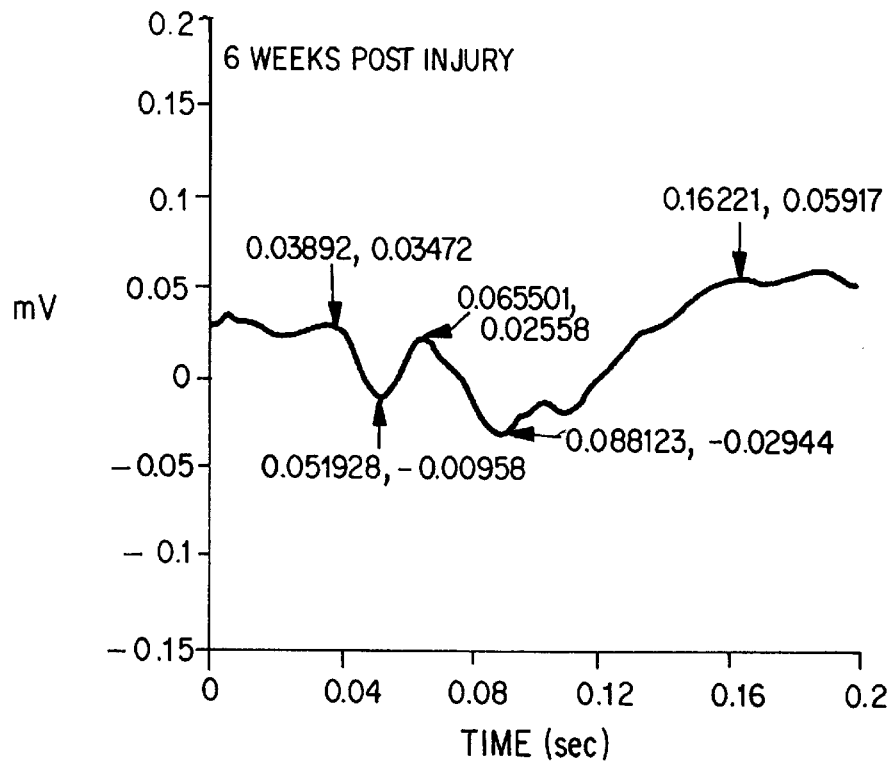
FIG. 19C displays the results obtained from the protocol in FIG. 19A with VEP potentials recorded 6 weeks after injury. Note that 6 weeks after injury the recovery is manifested by small peaks, all shifted relative to those in the uninjured nerve. Values are means obtained from four recordings at each time point (solid lines)±SE (grey line)
Figure 20A:
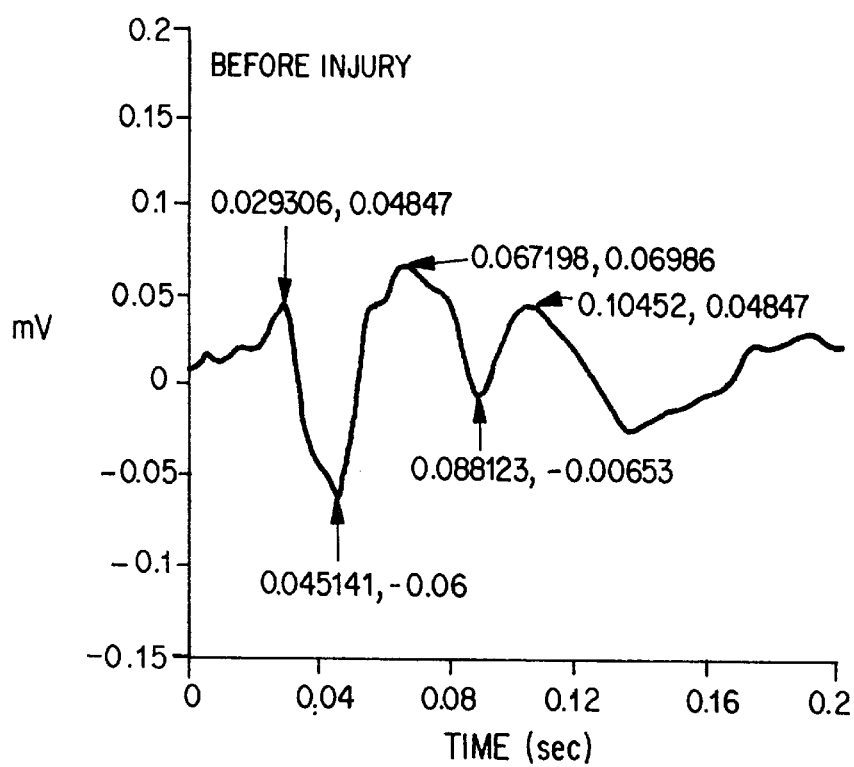
FIG. 20A depicts on-line VEP response in control (buffer-treated) injured nerves. A representative animal (rat) was treated with buffer and VEP responses were recorded before the injury, as described in the specification. Values are means (solid lines)±SE (grey line)
Figure 20B:
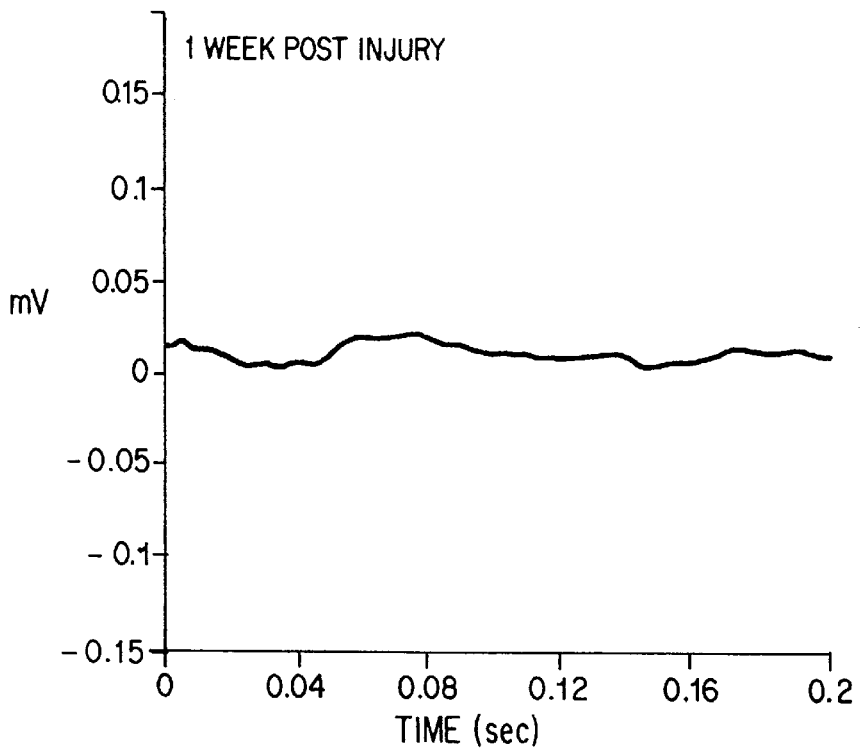
FIG. 20B depicts VEP responses according to the protocol of FIG. 20A 1 week after injury. Values are means (solid lines)±SE (grey line)
Figure 20C:
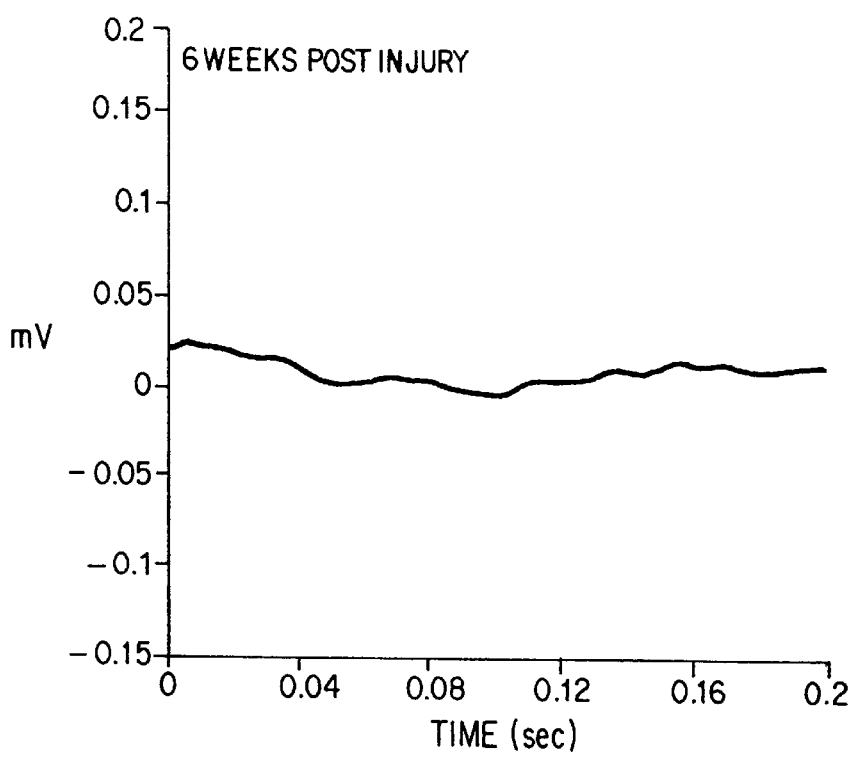
FIG. 20C depicts VEP responses according to the protocol of FIG. 20A 6 weeks after injury. Values are means (solid lines)±SE (grey line)

FIG. 19A–C show typical results of on-line recording of functional activity in a $TG_N$-treated injured nerve of a SPD rat. VEP responses were recorded before the injury (panel A) and 1 and 6 weeks after injury (panels B and C, respectively). One week after injury, no VEP response was detectable. Six weeks later, however, positive VEP activity was recorded. The peaks are shifted relative to the preinjured state, thus having longer latencies and smaller amplitudes. FIG. 20A–C present a typical recording from a control (buffer-treated) animal. The figure shows VEP response acivities in a representative animal recorded before the injury (panel A) and 1 and 6 weeks after injury (panels B and C, respectively). No VEP response could be detected 6 weeks after injury.

TABLE VIII

VEP response of individual $TG_N$-treated injured and control animals. The VEP response of each animal was recorded 6 weeks after injury. The latency and amplitude of the first negative peak response are presented. All of these animals showed a complete absence of VEP activity 1 week after injury.

| Treatment | Latency (msec) | Amplitude ($\mu V$) |
|---|---|---|
| $TG_N$ | 0 | 0 |
| $TG_N$ | 56 | 28 |
| $TG_N$ | 0 | 0 |
| $TG_N$ | 78 | 44 |
| $TG_N$ | 57 | 46 |
| $TG_N$ | 0 | 0 |
| $TG_N$ | 51 | 24 |
| $TG_N$ | 53 | 38 |
| $TG_N$ | 57 | 42 |
| $TG_N$ | 79 | 27 |
| Control (n = 12) | 0 | 0 |

TABLE IX

Characteristics of VEP response in $TG_N$-treated injured and intact nerves. The mean latency and amplitude of the first negative peak of activity are presented. ANOVA, one-factor analysis yielded. *DF = 1, F = 34.018, P = 0.0001. **DF = 1, F = 93.101, P = 0.0001. Comparison according to Fisher revealed significance at 95%.

| Group | Latency* (msec) (mean ± SE) | Amplitude** ($\mu V$) (mean ± SE) | Number of animals |
|---|---|---|---|
| $TG_N$-treated injured nerve | 61.6 ± 4.5 | 35.6 ± 3.4 | 7 |
| Intact nerve | 39.7 ± 1.4 | 131.8 ± 8.7 | 13 |

This experiment demonstrates recovery of function in adult transected mammalian CNS nerves after treatment that presumably facilitates growth within their own degenerative environment (Lavie et al., 1990). Other studies have achieved growth of CNS axons within their own environment, so far without physiological recovery. Thus, for example, it was shown that the use of hybridoma cells producing antibodies against myelin-associated inhibitors of mammals promotes regrowth within the spinal cord (Schnell and Schwab, 1990). Likewise, Millipore implants coated with embryonic astrocytes promoted growth of crushed dorsal root axons into the grey matter of the adult mammalian spinal cord (Rudge et al., 1990). Physiological activity of newly growing mammalian axons has been demonstrated, not as a result of a growth within the nerve's own environment, but after the nerve's own growth-hostile environment was replaced by an implanted peripheral nerve bridge; this resulted in a growth of axons along the length of the implant, all the way to the brain. Superior colliculus synapses were found but the axons penetrated only to a limited distance within the target CNS tissue (Kirstead et al., 1990; Aguayo et al., 1990a and 1990b).

In this experiment, functional recovery followed local application of the $TG_N$ enzyme, which is elevated after injury in a spontaneously regenerating nervous system. This enzyme, which was isolated from regenerating fish optic nerves, dimerizes IL-2 in vitro, thus altering its properties in such a way as to render it cytotoxic to oligodendrocytes. In the present experiment, $TG_N$ was applied in vivo, on the assumption that the active IL-2 dimer is formed in vivo, and that elimination of mature oligodendrocytes by the enzymatically-produced dimeric IL-2 soon after injury, at least in the immediate vicinity of the injury site, might facilitate growth, but other mechanisms of activity of the enzyme $TG_N$ should not be eliminated.

The VEP response is an objective physiological parameter indicative of the integrity of the visual system from the retina to the cortex. In view of our finding that no VEP activity was detectable 1 week after injury but significant activity was recorded 5 weeks later, it is reasonable to assume that the VEP response is the result of axonal growth and reconnection. Moreover, in most of the $TG_N$-treated nerves the latency was prolonged relative to intact nerves, further supporting the notion that the response might be the result of newly growing (unmyelinated) axons which reinnervate the target.

Example 19

Preparation of Linear Dimeric IL-2

A linear dimeric IL-2 protein was constructed by the use of a viral expression vector, thus enabling large amounts of the linear IL-2 dimer to be expressed in the medium of the infected cells.

In this example, the following experimental procedures were used.

19.1 Lymphocytes and RNA Preparation

Human lymphocytes were isolated and stimulated to maximize the amount of IL-2 mRNA. Peripheral venous blood was collected in 60-ml heparinized syringes and diluted with an equal volume of phosphate-buffered saline (PBS). The mixture was then layered on top of a 1.077 g/ml Percoll solution (49.2% Percoll, 150 mM NaCl) and centrifuged at 400×g for 25 min at 4° C. Lymphocyte-rich buffy coats were collected with a glass Pasteur pipette and washed twice in PBS. Lymphocytes were plated at $2 \times 10^6$ cells/ml and incubated for 3 days in the presence of 1 $\mu$g/ml peanut hemagglutinin (PHA; Sigma) in complete medium consisting of RPMI-1640 (Gibco), 2% heat-inactivated fetal calf serum (IFCS), 100 U/ml penicillin and 0.1 mg/ml streptomycin (Sigma), and $5 \times 10^{-5}$ M p-mercaptoethanol. Cells were then washed and plated onto new flasks at $2 \times 10^6$ cells/ml in complete medium and stimulated with 1 μg/ml PHA and 10 ng/ml phorbol 12-myristate 13-acetate (PMA) for 3 hr. Total cellular RNA was isolated by the RNAzol B method (Chomczynski and Sacchi, 1987) with the aid of the Biotec Laboratories kit, and quantified by absorbance at 260/280 nm.

19.2 Polymerase Chain Reaction (PCR) and Sequence Analysis

PCRs were carried out with the aid of the GeneAmp kit (Cetus, USA). Total human lymphocyte RNA (1 μg) was subjected to a reverse transcriptase reaction at 42° C. for 15 min with PCR buffer (1×, final), 5 mM MgCl$_2$, 1 U/μl RNase inhibitor, 50 pmol specific downstream primer and 1 mM of each dNTP in a total reaction volume of 20 μl. Following heat inactivation of the reverse transcriptase, the reaction mixture was made up to 100 μl by the addition of 50 pmol downstream primer, 100 pmol upstream primer, PCR buffer (1×, final), 2 mM MgCl$_2$ solution and 2.5 U taq DNA polymerase. The first PCR cycle was carried out for 1 min at 45° C., 1 min at 72° C., and 1 min at 94° C. This was followed by 30 cycles each of 30 sec at 55° C., 1 min at 72° C. and 1 min at 94° C. An extra 5 min at 72° C. was added at the end of the 30 cycles to ensure that the ends of the cDNAs were completely filled in, thus promoting proper digestion with restriction enzymes (if reactions were started from an amplified DNA, each of 30 cycles lasted for 1 min at 94° C. and 1.5 min at 72° C., so that nonspecific amplified bands could be eliminated). The PCR products were ligated to an appropriately digested bluescript KS-vector. Each of the DNAs to be ligated (10 ng) was heated to 65° C. for 5 min, and then incubated for 15 min at room temperature with ligation buffer (1×, final; Stratagene) and 5 U of T4 DNA ligase (Stratagene) in a total reaction volume of 10 μl. Ligation took place during overnight incubation at 15° C. The recombinants were cloned (to Epicurian coli, Sure competent cells; Stratagene) and plated for overnight growth on plates containing ampicillin. Positive clones were defined according to the alkali method for miniscale DNA preparations (Sambrook et al., 1989), followed by restriction enzyme analysis and gel electrophoresis. Positive clones were sequenced by the Sanger dideoxy chain termination technique with the aid of the Sequenase kit (USB).

19.3 Transfection of Cells, Generation of Viral Vector and Protein Extraction

Rabbit skin (RS) cells and African green monkey kidney (Vero) cells were grown in Dulbecco's modified Eagle's medium (DMEM) supplemented with 10% IFCS, 1% glutamine, and 1% penicillin-streptomycin. RS cells were transfected with 20 μg of pCB-IL-2 dimer (described hereinafter) by the calcium phosphate method (Graham and van der Eb, 1973) with subsequent glycerol shock (Parker and Stark, 1979). Transfection efficiencies, ranging between 10 and 20%, were determined on the basis of the number of blue cells/total cells per plate, by histochemical detection of bacterial β-galactosidase (Sanes et al., 1986), in cells cotransfected with 10 μg of the pCB-IL-2 dimer and 10 μg of x-gal plasmid DNA. Following overnight incubation at 37° C. and 5% CO$_2$, the medium was removed and cells were superinfected with the temperature-sensitive HSV1 (Graham and van der Eb, 1973) tsK strain (Davison et al., 1984), at a multiplicity of infection (moi) of 0.1 plaque-forming units (pfu)/cells. Following incubation for 1.5 hr at 31.5° C., cells were washed twice with PBS supplemented with 1% IFCS and incubated at the same temperature in DMEM/1% IFCS/1% penicillin-streptomycin/1% glutamine.

Viral stocks were harvested when all of the cells exhibited a cytopathic effect, usually 2 days after superinfection. Rounded cells in the medium were pelleted at 1000 g for 5 min, and the pellets were resuspended in 1 ml of virus buffer (150 mM NaCl/20 mM Tris, pH 7.5). Suspensions were rapidly frozen at −70° C. and thawed to 37° C. (repeated three times), and were then used to infect Vero cells at different dilutions of the defective virus. Following overnight incubation at 37° C. (a nonpermissive temperature for tsK), the medium containing the released synthesized protein was collected and the cells were extracted by incubation for 2 hr at 4° C. in 10 mM Tris, pH 7.5, 150 mM NaCl, 1% Triton, 1 mM EDTA, 1 mM spermidine, and protease inhibitors (25 μg/ml leupeptine and 5 μg/ml pepstatin), after which the supernatants were collected. The resulting products were subjected to Western blot analysis (Eitan et al., 1992) to verify the expression of IL-2 dimeric protein in the medium/extracts of the infected cells.

19.4 Construction of human IL-2 cDNA products by PCR

Figure 21B:
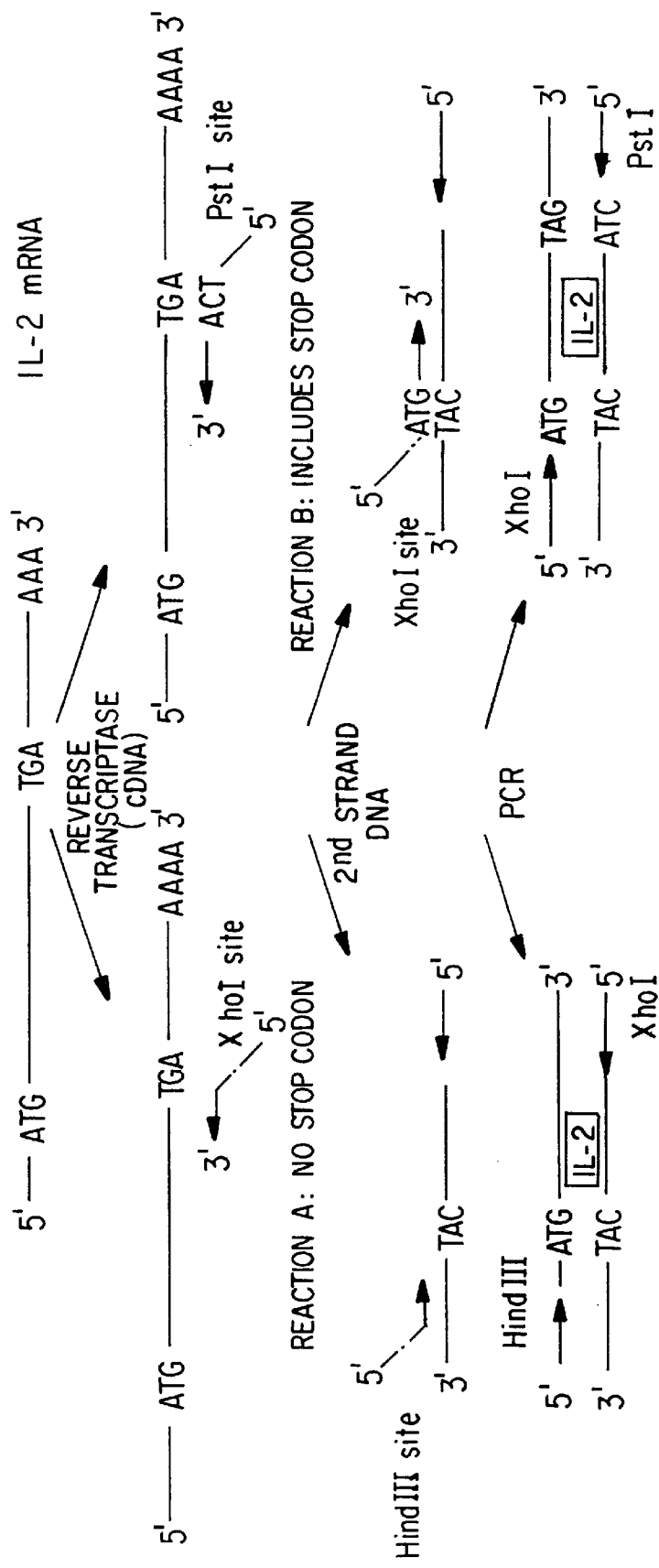
FIG. 21B shows the two PCRs employed to produce copies of the two different monomeric IL-2 cDNAs used to construct the linear dimeric IL-2 according to FIG. 21A.

The IL-2 cDNA sequence derived from human lymphocytes (Taniguchi et al., 1983) was run through a primer designer program which assists in the choice of optimal primers for PCR. In parallel, the sequence was run through a clone manager program, which yielded a restriction map that allowed us to detect restriction sites not present in the IL-2 gene. These sites were added to the ends of the primers. We then ran two PCRs: reaction A produced a copy of the IL-2 cDNA that included all translated codons, but stopped immediately before the last translated codon, so that there was no stop codon; the product of reaction B started with the first translated codon but ended beyond the stop site, so that the stop codon was included. The two sets of primers and PCRs are illustrated in FIG. 21. The restriction sites engineered on the downstream primer for reaction A and the upstream primer for reaction B. were the same, thus allowing the construction of a dimerized cDNA by fusion of the products of A and B in frame and in the appropriate orientation. Since a restriction site was added, there were six bases between the last codon of product A and the first codon of product B. which resulted in the addition of two amino acids at the junction. We anticipated that the contribution of the two extra amino acids to each of the IL-2 monomeric molecules in the dimer would be minimal.

19.5 Sequence analysis of the PCR products

Since the PCR products were used in expression experiments, it was important to verify that no mutations had been introduced during the PCR process. Three positive appropriately digested clones (as described in 19.2 above) of each PCR type were chosen for sequence analysis in which one of each set of clones was found to express the right sequence, with no mutations. These two clones were chosen for construction of the linear IL-2 dimer.

19.6 Construction of the linear IL-2 dimer in the defective viral vector

Figure 22:
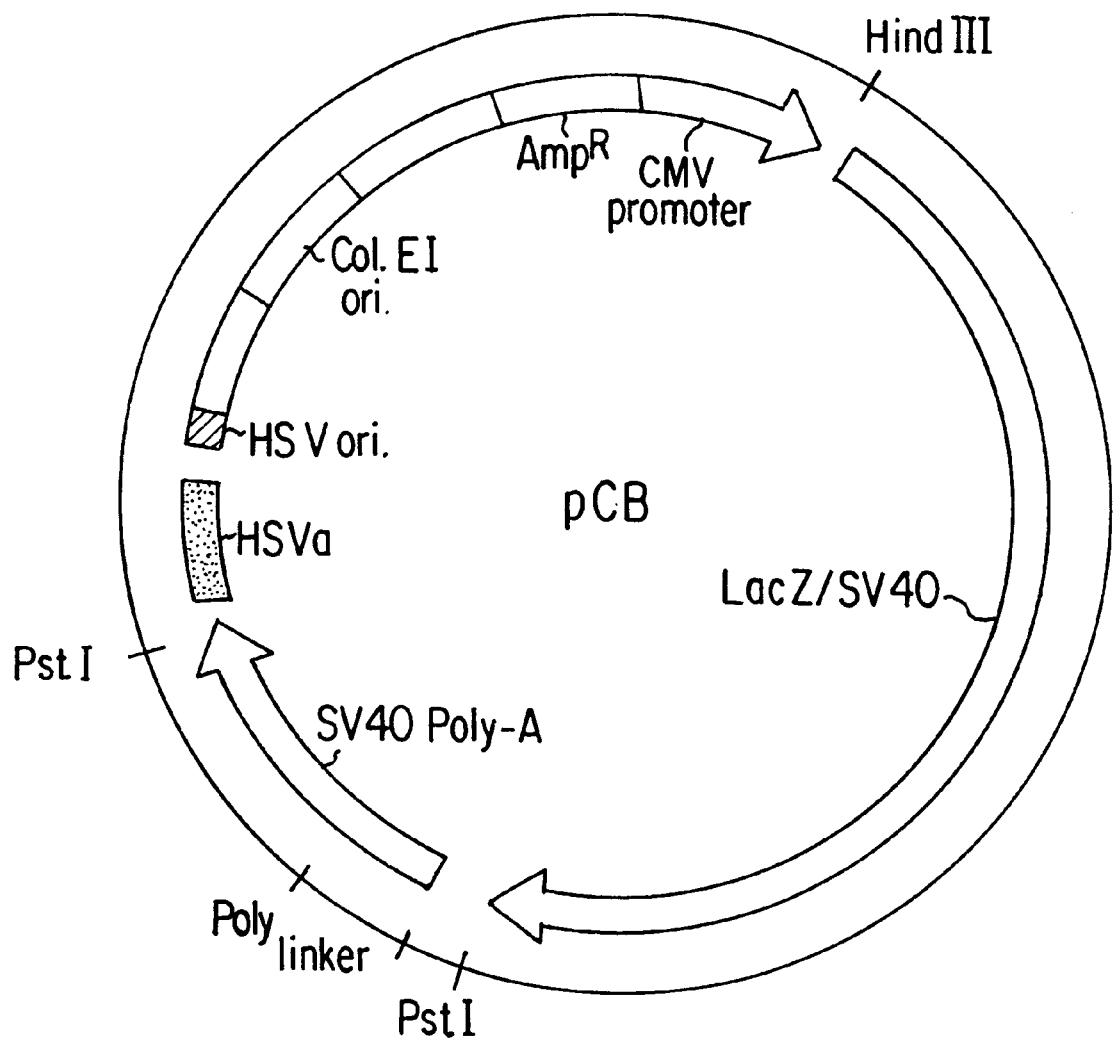
FIG. 22 depicts the defective viral vector amplicon plasmid pCB. The amplicon includes a fragment from pRB3119 containing the HSV1 cleavage/packaging signal (HSVa), a fragment containing an HSV origin of DNA replication (HSV ori), and a fragment from pcDNAlac containing the CMV promoter, lacZ gene, and simian virus 40 polyadenylation signal [poly(A)+signal]. These sequences were inserted into the ampicillin-resistant plasmid pT7-3, containing a β-lactamase gene ($Amp^R$) and a bacterial origin of DNA replication (Col E1 ori). This amplicon served as the basis for the defective viral vector genome used in the application.
Figure 23A:
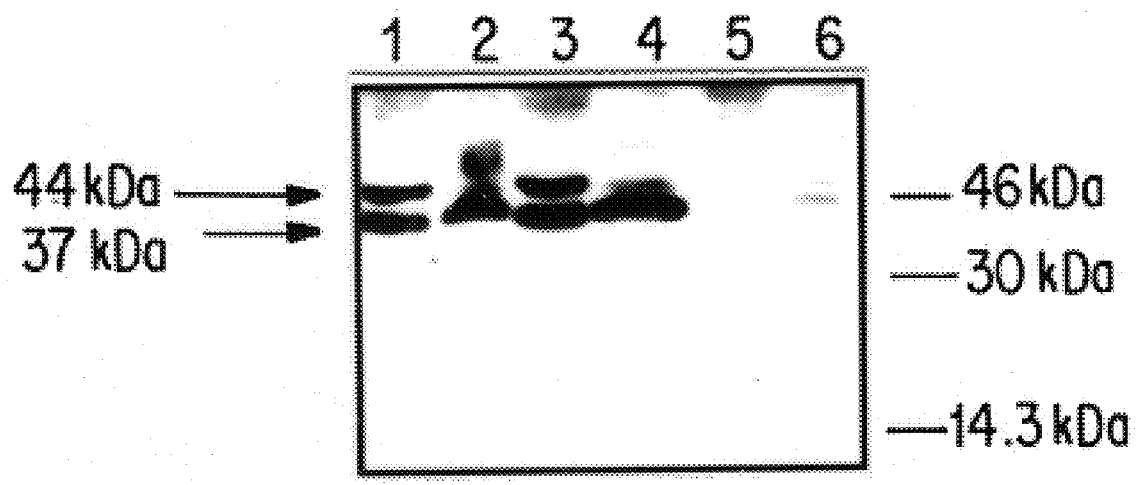
FIG. 23A shows Western blot analysis of the linear IL-2 dimer with mouse antihuman IL-2 monoclonal antibodies. The figure shows two dilutions (1:3, lanes 1, 3, 5, and 1:9, lanes 2, 4, 6) of medium collected from infected Vero cells (lanes 1, 3). Infected Vero cell extracts (lanes 2,4) and medium and cell extracts obtained from cells infected by the defective virus only (lanes 5 and 6, respectively) were electrophoresed on sodium dodecyl sulfate-polyacrylamide gel electrophoresis (SDS/PAGE). Arrows point to the IL-2 immunoreactive bands in each slot.
Figure 23B:
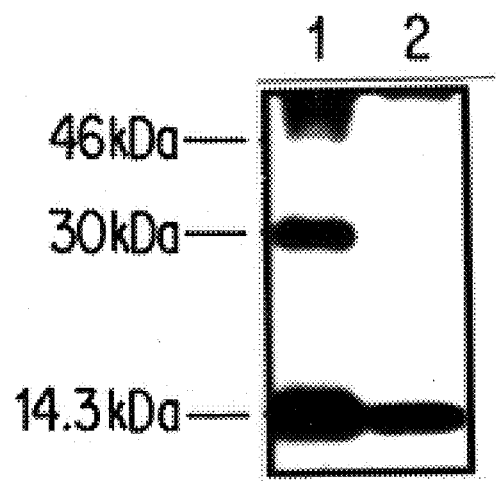
FIG. 23B shows a Western performed according to the protocol of FIG. 23A of the commercial monomeric IL-2 (lane 2) and the dimeric IL-2 (lane 1), synthesized by the nerve-derived transglutaminase and used as size controls. Molecular markers were electrophoresed on the same gels and their positions are indicated.
Figure 24:
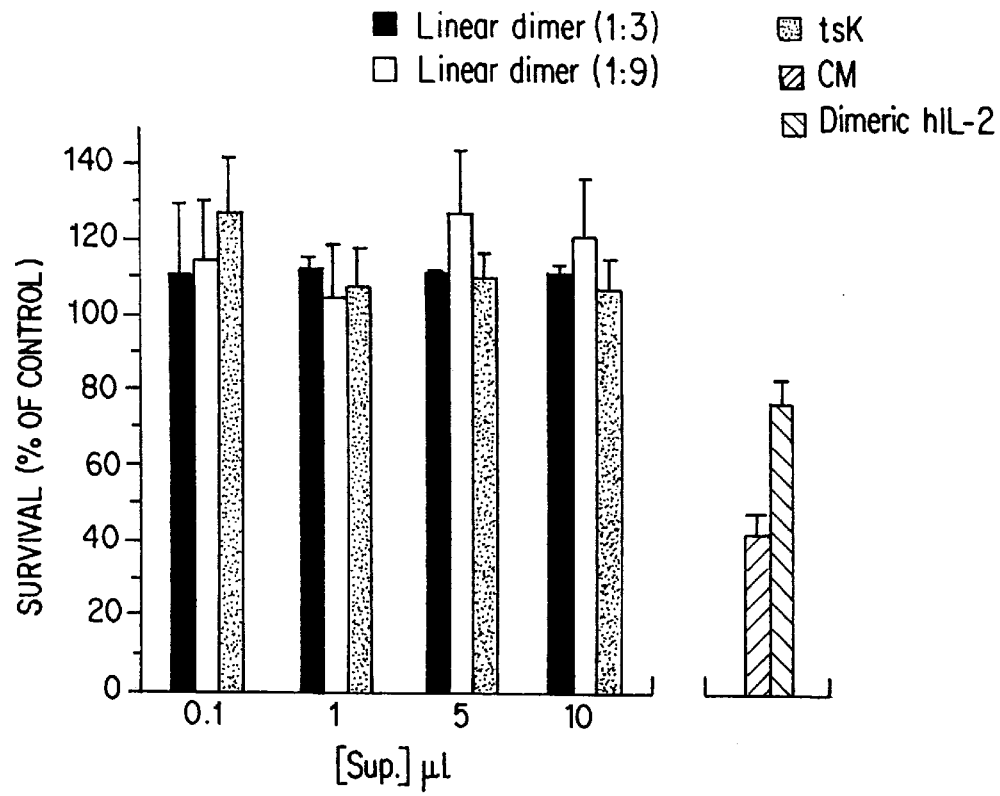
FIG. 24 shows that linear dimeric IL-2 is not cytotoxic to oligodendrocytes. Cytotoxic activity against oligodendrocytes, assessed by the colorimetric MTT assay, was examined by application of aliquots from the samples described in FIG. 11, at different dilutions (left panel). The results were compared to parallel experiments (right panel) in which oligodendrocytes were treated either with soluble substances derived from regenerating optic nerves (CM) in which the cytotoxic IL-2-like factor was identified with enzymatically-synthesized human dimeric IL-2. Both of these treatments caused a significant reduction (by ANOVA: dimeric IL-2, F=7.833; CM, F=104.976; P=0.02 and P=0.0001, respectively, according to Fisher comparison) in the number of mature oligodendrocytes. The experiment, which was repeated three times, was performed in triplicate. Results are presented as means±SD of the untreated culture values, representing 100% survival.
Figure 25:
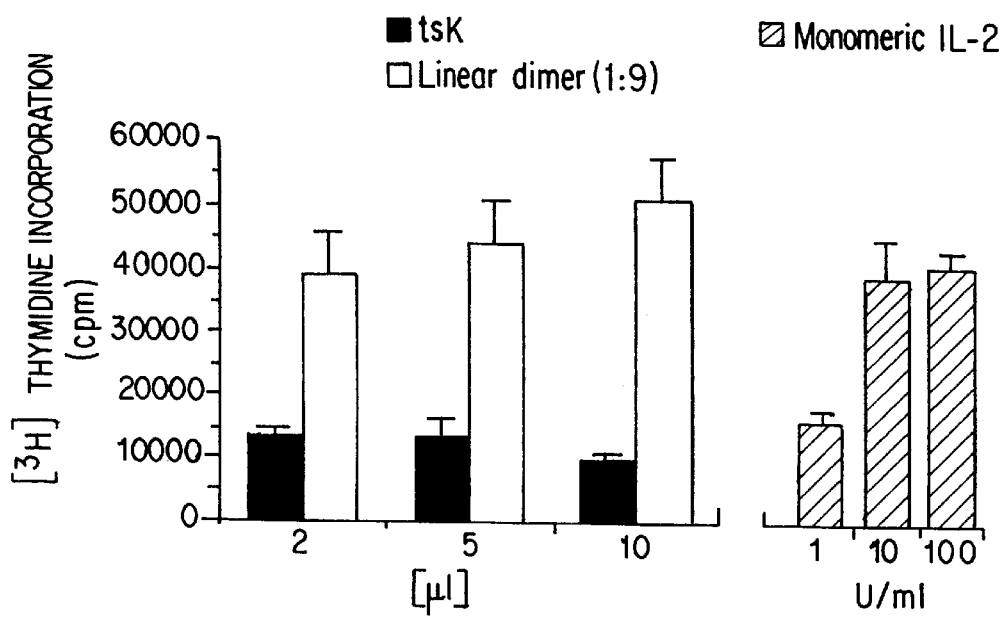
FIG. 25 shows that linear dimeric IL-2 causes proliferation of CTLL-2 cells. Biological activity on CTLL-2 cells, assayed by thymidine incorporation, was examined by application of aliquots from the samples described in FIG. 11 (left panel). The results were compared with those of a parallel experiment (right panel) in which CTLL-2 were treated with commercial monomeric human IL-2 as a control. The experiment was performed in triplicate. Results are presented in cpm.

The prototype of the defective viral vector used herein (pCB; FIG. 22) includes a fragment from pRB3119 containing the HSV1 cleavage/packaging signal (HSVa), a fragment containing an HSV origin of DNA replication (HSV ori), and a fragment from pcDNAlac containing the cytomegalovirus (CMV) promoter, lacZ gene, and simian virus 40 polyadenylation signal [poly(A)+signal]. These sequences were inserted into the ampicillin-resistant plasmid pT7–3, which contains a β-lactamase gene (Amp$^R$) and a bacterial origin of DNA replication (Col El ori). As a first step, the lacZ gene was cut out of the vector. This was done by linearization of the vector with HindIII, followed by its partial digestion with PstI and extraction of the right vector band from an agarose gel with the aid of the Geneclean II kit (BIO 101). The two PCR products were ligated, in a triple ligation, into the resulting vector (their correct direction, A followed by B, was determined by the previously designed complementary restriction sites of the two products, as discussed in 19.4 above). The resulting construct, pCB-IL-2 dimer, was double-checked by restriction enzyme analysis, followed by large-scale DNA preparation (CsCl) (Sambrook et al., 1989), and transfected into the rabbit skin (RS) cells. Harvested viral stocks were used to infect-African green monkey kidney (Vero) cells, as discussed in 19.3 above.

Example 20
Analysis of the linear dimeric IL-2 protein product

Since IL-2 protein is known to be released into the medium of growing cells, the medium of the infected Vero cells obtained in Example 19.6 above was collected and used as a source of the linear dimeric IL-2 protein. In parallel, cell extracts were prepared and examined under the same conditions in order to determine whether the synthetic protein was retained in the infected cells. The two suspensions were subjected to Western blot analysis by the use of monoclonal antibodies directed against human IL-2 (FIG. 23, left panel). Two dilutions (1:3, lanes 1,3,5, and 1:9, lanes 2,4,6) of cell supernatants (lanes 1,3) and extracts (lanes 2,4), and of supernatant (lane 5) and cell extract (lane 6), obtained from cells infected by the defective virus only, were analyzed. In contrast to the cells infected only with the defective virus (lanes 5,6), where no IL-2 immunoreactive band could be detected, all four lanes (1–4) containing either supernatants (1,3) or cell extracts (2,4) expressed bands of about 37 kd that inLmmunoreacted with the specific IL-2 monoclonal antibodies. The commercial human monomeric IL-2 protein has a molecular weight of 14 kd and the dimeric protein synthesized from the commercial monomeric IL-2 by the nerve-derived transglutaminase as described hereinbefore, has a molecular weight of 28 kd (FIG. 23, right panel, lanes 2 and 1, respectively). The difference in size between the dimeric IL-2 produced by the two different procedures may be explained by posttranslational modifications of the linear dimerized protein in the infected cells, in contrast to the dimer synthesized in vitro by transglutaminase and monomeric IL-2. The supernatants (lanes 1,3) contained an extra band of about 44 kd. This extra band can also be explained in terms of posttranslational modifications, such as glycosylation or phosphorylation, which may have occurred during the release of the protein into the medium.

Example 21

Linear dimeric IL-2 is not cytotoxic to oligodendrocytes

We then attempted to find out whether this linear human IL-2 dimer could mimic the transglutaminase-dimerized human IL-2 of the invention with respect to in vitro cytotoxicity. To investigate this possibility, aliquots from the same samples and the same dilutions of the supernatants as those used in Example 20 for Western blot analysis were applied to cultures of rat oligodendrocytes.

Enriched oligodendrocyte cultures derived from neonatal rat brain were prepared as described (Bottenstein and Sato, 1979 and seeded on glass coverslips previously coated with poly-L-lysine (PLL)(Eitan et al. 1992). After 48 hr, the seeded cells were treated with the aliquots of the linear dimeric IL-2 protein and the extent of cytotoxicity was determined by the number of surviving cells assessed calorimetrically (Eitan et al.,1992). The numbers of mature oligodendrocytes, asssayed by the calorimetric method, were not reduced relative to untreated cells used as control (100%) in any of the dilutions of the linear dimer or tsK used as a control (FIG. 24, left panel). No reduction could be detected even at high protein concentrations (FIG. 24, left panel). On the other hand, soluble substances derived from regenerating fish optic nerves in which the IL-2 -like cytotoxic factor was identified (Eitan et al. , 1992), as well as human dimeric IL-2 enzymatically synthesized in vitro, caused significant reductions in the numbers of mature oligodendrocytes (FIG. 24, right panel).

Example 22

Detection of IL-2 biological activity in the linear dimeric IL-2 using an IL-2 -dependent T cell line To exclude the possibility that lack of cytotoxicity of the linear dimer on oligodendrocytes is not caused by loss of activity of the IL-2 protein as a result of expression via the HSV1 vector, we assayed the activity of the linear dimer and assessed its ability to mimic the monomeric IL-2 as a mitogen on T cell line (CTLL-2). Thus CTLL-2 cells were seeded in multiwell culture plates ($2\times10^3$ cells/100 $\mu$l of RPMI containing 10% IFCS, 2 mM glutamine and 0.05 mM β-mercaptoethanol). After 2–3 hr, aliquots from the same samples and the same dilution (1:9) of the supernatant as those used for Western blot analysis and for the cytotoxicity assay were applied to the cells for an overnight incubation at 37° C. One $\mu$Ci of [$^3$H] thymidine was added to each well, for an additional 4-h incubation. At the end of the incubation, cells were harvested and thymidine incorporation was detected by cpm. Measurement of thymidine incorporation (cpm) showed that, in contrast to tsK used as a control, the addition of different concentrations of the linear dimer caused cell proliferation in a dose-dependent manner (FIG. 25, left panel). The observed proliferation was even higher than that caused by the commercial monomeric IL-2 used as a control (FIG. 25, right panel).

This experiment shows that the resulting linear dimeric IL-2, being a translational product, differs from the enzymatically produced dimer, which is a posttranslational modification of IL-2, with respect to citotoxicity to oligodendrocytes. The linear dimer, while retaining the known IL-2 activity of monomeric IL-2 with respect to mitogenicity on T cells, was not cytotoxic to oligodendrocytes, suggesting that the lack of oligodendrocyte cytotoxicity of the linear dimeric IL-2 is not caused by a loss of biological activity during its preparation, but is related to its conformational structure, which evidently does not meet the requirements for oligodendrocyte cytotoxicity.

REFERENCES

Aguayo, A. J., G. M. Bray, M. Rasminsky, T. Zwimpfer, D. A. Carter and M. Vidal-Sanz (1990a) J. Exp. Biol. 153:199.

Aguayo, A. J., G. M. Bray, D. A. Carter, M. P. Villegas-Perez, M. Vidal-Sanz and M. Rasminsky (1990b) Acta Neurobiol. Exp. 50:381.

Araujo, D. M., Lapchak, P. A., Collier, B. and Quirion, R., Brain Res., 498 (1989) 257–266.

Benveniste, E. N. and Merrill, J. E., Nature, 321 (1986) 610–613.

Bignami, A., Eng, L. F., Dahl, D. and Uyeda, C. T., Localization of glial fibrillary acidic protein in astrocytes by immunofluorescence, Brain Research, 43 (1972) 429–433.

Bottenstein, J. E. and Sato, G. H., Growth of a rat neuroblastoma cell line in serum-free supplemented medium, Proc.Natl.Acad.Sci.U.S.A., 76 (1978) 514–517

Bradford, M., A rapid sensitive method for quantitation of microgram quantities of protein utilizing the principle of protein-dye binding, Anal.Biochem. 72 (1976) 248–256.

Caspi, R. R. and Avtalion, R. R., Dev. Comp. Immunol., 8 (1984) 51–60.

Chakrabarty, G. et al.(1987) J. Neurochem. 48:669.

Chomczynski, P., and N. Sacchi (1987) Anal. Biochem. 162:156–159.

Cohen, A. and Schwartz, M., Conditioned media of regenerating fish optic nerves modulate laminin levels in glial cells, J. Neurosci.Res., 22 (1989) 269–273.

Cohen, A., Sivron, T., Duvdevani, R. and Schwartz, M., Brain Res., 537 (1990) 24–32.

Davison, M. J., V. G. Preston and D. J. McGeoch (1984) J. Gen. Virol. 65:859–863.

Devos, R. (1983) Nucleic Acids Research 11:4307–4323.

Eisenbarth, G. S., Walsh, F. S. and Nirenberg, M., Monoclonal antibody to a plasma membrane antigen of neurons, Proc.Natl.Acad.Sci.U.S.A., 76 (1979) 4913–4917.

Eitan, S., R. Zisling, A. Cohen, M. Belkin, D. L. Hirschberg, M. Lotan and M. Schwartz (1992) Proc. Natl. Acad. Sci. U.S.A. 89:5442–5446.

ffrench-Constant, C. and Raff, M. C., Proliferating bipotential glial progenitor cells in adult rat optic Graham, F. L. and A. J. van der Eb (1973) Virology 52:456–467.

Greenberg, C. S., P. J. Birckbichler and R. H. Rice (1991) FASEB J. 5:3071.

Hadani, M., Harel, A., Solomon, A., Belkin, M., Lavie, V. and Schwartz, M., Substances originating from optic nerves of neonatal rabbit induce regeneration-associated response in injured nerves of adult rabbit, Proc.Natl.Acad.Sci.U.S.A., 81 (1984) 7965–7969.

Jeserich, G. and Romen, T., Glia 3 (1) (1989) 65–74.

Kierstead, S. A., M. Rasminsky, J. Fukuda, D. A. Carter, A. J. Aguayo and M. Vidal-Sanz (1990) Science 246:255.

Lavie, V Harel, A., Doron, A., Solomon, A., Lobel, D., Belkin, M., Ben-Bassat, S., Sharma, S. and Schwartz, M., Morphological response of injured adult rabbit optic nerves to implants containing media conditioned by growing optic nerves, Brain Research, 419 (1987) 166–172.

Lavie, V., Murray, M., Solomon, A., Ben-Bassat, S., Belkin, M., Rumelt, S. and Schwartz, M., J. Comp. Neurol., 298 (1990) 293–314.

Liang, S. M., Liang, C. M. and Chiueh, C. C., Biochem. Biophys. Res. Commun., 165 (1989) 1312–1318.

Lillien, L. E., Sendtner, M., Rohrer, H., Hughes, S. M. and Raff, M. C., Type-2 astrocyte development in rat brain cultures is initiated by a CNTF-like protein produced by type-1 astrocytes, Neuron, 1 (1988) 485–494.

McCarthy, K. D. and DeVellis, J., Preparation of separate astroglial and oligodendroglial cell cultures from rat cerebral tissue, J.Cell.Biol. 851 (1980) 890–902.

Miller, R. H. and Raff, M. C., J. Neurosci. 4 (1984) 585–592.

Nieto-Sampedro, M. and Chandy, K. G., Neurochem. Res., 12 (1987) 723–727.

Noble, M. Murray, K., Stroobant, P., Waterfield, M. D. and Riddle, P., Platelet-derived growth factor promotes division and motility and inhibits premature differentiation of the oligodendrocyte/type 2 astrocyte progenitor cell, Nataure(Lond.) 333 (1988) 560–562.

Parker, B. A. and G. R. Stark (1979) J. Virol. 31:360–369.

Raff, M. C., Lillien, L. E., Richardson, W. D., Burne, J. F. and Noble, M. D., Platelet-derived growth factor from astrocytes drives the clock that times oligodendrocyte development in culture, Nature(Lond.) 333 (1988) 562–565.

Raff, M. C. and Miller, R. H., T.I.N.S. 7 (1984) 469–472.

Raff, M. C., Miller, R. H. and Noble, M., A glail progenitor cell that develops in vitro into an astrocyte or an oligodendrocyte depending on the culture medium, Nature (Lond.), 303 (1983) 390–396.

Raff, M. C., Mirsky, R., Fields, K. L., Lisak, R. P., Dorfman, S. H., Silberberg, D. H., Grenson, N. A. Leibowitz, S. and Kennedy, M. C., Galcctocerebroside is a specific cell-surface antigenic marker for oligodendrocytes in culture, Nature(London), 274 (1978) 813–816.

Robb, R. J. et al. (1983), Proc. Natl. Acad. Sci. U.S.A. 80:5990.

Robbins, D. S., Shirazi, Y., Drysdale, B., Liberman, A., Shin, H. S. and Shin, M. L., Production of cytotoxic factor for oligodendrocytes by stimulated astrocytes, J.Immunol., 139 (1987) 2593–2597.

Rosen, C. L., Bunge, R. P., Ard, M. D. and Wood, P. M., Type 1 astrocytes inhibit myelination by adult rat oligodendrocytes in vitro, J.Neurosci., 9 (1988) 3371–3379.

Richardson, W. D., Pringle, N. , Mosley, M. J. Westermark, B. and Dubois-Dalcq, M., A role for platelet-derived growth factor in normal gliogenesis in the central nervous system, Cell, 53 (1988) 309–319.

Rudge, J. S. and J. Silver (1990) J. Neurosci. 10:3594.

Sanes, J. R., J. L. R. Rubenstein and J. F. Nicolas (1986) EMBO J. 5:3133–3142

Saneto, R. P., Altman, A., Knobler, R. L., Johnson, J. and De Vellis, J., Proc. Natl. Acad. Sci. U.S.A., 83 (1986) 9221–9225.

Saneto, R. P., Chiappelli, F. and De Vellis, J., J. Neurosci. Res., 18 (1987) 147–154.

Schnell, L. and Schwab, M. E., Nature, 343 (1990) 269–272.

Schwartz, M., Belkin, M., Harel, A., Solomon ,A., Lavie, V., Hadani, M., Rachailovich, I. and Stein-Izsak, C., Regenerating fish optic nerves and regeneration-like response in injured optic nerve of adult rabbits, Science, 228 (1985) 600–603.

Schwartz, M., Solomon, A., Lavie, V., Ben-Bassat, S., Belkin, M. and Cohen, A., Brain Res., 545 (1991) 334–338.

Selmaj, K. W. and Ramie, C. S., Tumor necrosis factor mediates myelin and oligodendrocytes damage in vitro, Ann.Neurol., 23 (1988) 339–340.

Sivron, T., Cohen, A., Duvdevani, R., Jeserich, G. and Schwartz. M., Glia, 3 (1990) 267–276.

T. Sivron. et al.(1991) Glia 4:591–601.

Smith, K. A., Science, 240 (1988) 1169–1176.

Sommer, I. and Schachner, M., Monoclonal antibodies (01 to 04) to oligodendrocyte cell surfaces: An immunocytological study in the central nervous system, Dev.Biol., 83 (1981) 311–327.

Taniguchi, T., H. Matsui, T. Fujita, C. Takaoka, N. Kashima, R. Yoshimoto and J. Hamuro (1983) Nature 302:305–310.

We claim:

1. A human enzymatically-producible dimeric IL-2 being water-soluble, being a covalent dimer of human IL-2, being selectively toxic to the oligodendrocyte lineage, which toxicity is neutralized by antibodies directed against IL-2, being obtainable from human IL-2 by incubation with transglutaminase, and having a molecular weight of about 30 kDa as determined by Western blot analysis.

2. The human dimeric IL-2 according to claim 1, wherein the transglutaminase is nerve-derived transglutaminase.

3. A pharmaceutical composition for inducing and facilitating regeneration of injured nerves of the central nervous system in mammals comprising a pharmaceutically effective amount of an enzymatically-producible dimeric IL-2 having oligodendrocyte cytotoxic activity and a pharmaceutically acceptable carrier.

4. A pharmaceutical composition according to claim 3 wherein said dimeric IL-2 is a mammalian dimeric IL-2.

5. A pharmaceutical composition according to claim 4 wherein said mammalian dimeric IL-2 is human dimeric IL-2.

* * * * *